US012799117B2

(12) United States Patent
Mulvihill et al.

(10) Patent No.: US 12,799,117 B2
(45) Date of Patent: Nov. 17, 2026

(54) PERK INHIBITING PYRROLOPYRIMIDINE COMPOUNDS

(71) Applicant: HiberCell, Inc., New York, NY (US)

(72) Inventors: Mark J. Mulvihill, New York, NY (US); An-Hu Li, New York, NY (US); Matthew David Surman, Albany, NY (US)

(73) Assignee: HIBERCELL, INC., New York, NY (US)

( * ) Notice: Subject to any disclaimer, the term of this patent is extended or adjusted under 35 U.S.C. 154(b) by 1239 days.

(21) Appl. No.: 17/639,279

(22) PCT Filed: Aug. 28, 2020

(86) PCT No.: PCT/US2020/048621

§ 371 (c)(1),
(2) Date: Feb. 28, 2022

(87) PCT Pub. No.: WO2021/041975

PCT Pub. Date: Mar. 4, 2021

(65) Prior Publication Data

US 2022/0356186 A1 Nov. 10, 2022

Related U.S. Application Data

(60) Provisional application No. 62/893,528, filed on Aug. 29, 2019.

(51) Int. Cl.
*C07D 487/04* (2006.01)

(52) U.S. Cl.
CPC .................................. *C07D 487/04* (2013.01)

(58) Field of Classification Search
CPC .................................................... C07D 487/04
See application file for complete search history.

(56) References Cited

U.S. PATENT DOCUMENTS

2003/0187001 A1 10/2003 Calderwood et al.
2010/0167945 A1 7/2010 Singh et al.
(Continued)

FOREIGN PATENT DOCUMENTS

CN 106748989 A 5/2017
EP 3067356 A1 9/2016
(Continued)

OTHER PUBLICATIONS

Adrian L. Smith: "Discovery of 1H-Pyrazolo-3(2H)-ones as Potent and Selective Inhibitors of Protein Kinase R-like Endoplasmic Reticulum Kinase (PERK)", Journal of Medicinal Chemistry, vol. 58, No. 3, Feb. 12, 2015, pp. 1426-1441.
(Continued)

*Primary Examiner* — Andrew D Kosar
*Assistant Examiner* — John D McAnany
(74) *Attorney, Agent, or Firm* — Scully, Scott, Murphy & Presser, P.C.

(57) ABSTRACT

The present application relates to compounds of the formula:

(I)

(Continued)

or its pharmaceutically acceptable salts thereof and to pharmaceutical compositions comprising same useful for inhibiting PERK and for treating related conditions and disorders, such as cancer.

20 Claims, 3 Drawing Sheets

(56) References Cited

U.S. PATENT DOCUMENTS

| | | | |
|---|---|---|---|
| 2013/0018038 A1 | 1/2013 | Axten et al. | |
| 2017/0022206 A1 | 1/2017 | Hodous et al. | |
| 2019/0241573 A1 | 8/2019 | Axten et al. | |
| 2019/0388426 A1 | 12/2019 | Nguyen et al. | |
| 2020/0031834 A1 | 1/2020 | Bartlett et al. | |
| 2022/0332722 A1 | 10/2022 | Mulvihill et al. | |
| 2022/0348583 A1 | 11/2022 | Mulvihill et al. | |
| 2022/0348584 A1 | 11/2022 | Mulvihill et al. | |
| 2022/0356186 A1 | 11/2022 | Mulvihill et al. | |

FOREIGN PATENT DOCUMENTS

| | | | | |
|---|---|---|---|---|
| EP | 3492454 A1 | | 6/2019 | |
| WO | WO-98/41525 A1 | | 9/1998 | |
| WO | WO-2003064397 A1 | | 8/2003 | |
| WO | WO-03/093297 A2 | | 11/2003 | |
| WO | WO-2005009961 A2 | | 2/2005 | |
| WO | WO-2007026920 A2 | | 3/2007 | |
| WO | WO-2007030377 A1 | | 3/2007 | |
| WO | WO-2010/080992 A1 | | 7/2010 | |
| WO | WO-2014/170706 A1 | | 10/2014 | |
| WO | WO-2015/056180 A1 | | 4/2015 | |
| WO | WO-2015136463 A1 | | 9/2015 | |
| WO | WO-2016/004254 A1 | | 1/2016 | |
| WO | WO-2016/075224 A1 | | 5/2016 | |
| WO | WO-2016/185160 A1 | | 11/2016 | |
| WO | WO-2017046737 A1 | * | 3/2017 | ................ A61P 3/10 |
| WO | WO-2018/009017 A1 | | 1/2018 | |
| WO | WO-2018/138358 A1 | | 8/2018 | |
| WO | WO-2018/194885 A1 | | 10/2018 | |
| WO | WO-2019/099564 A1 | | 5/2019 | |
| WO | WO-2019/191115 A1 | | 10/2019 | |
| WO | WO-2020/070053 A1 | | 4/2020 | |

OTHER PUBLICATIONS

Aguirre-Ghiso et al: "Targeting dormant cancer", Nature Medicine, vol. 19, No. 3, Mar. 6, 2013, pp. 276-277 (4 pages).
Atkins et al. Characterization of a novel PERK kinase inhibitor with antitumor and antiangiogenic activity. Cancer Res. 2013;73:1993-2002.
Avivar-Valderas et al. Regulation of autophagy during ECM detachment is linked to a selective inhibition of mTORC1 by PERK. Oncogene. 2012;32(41):4932-4940.
Avivar-Valderas et al. PERK integrates autophagy and oxidative stress responses to promote survival during extracellular matrix detachment. Mol Cell Biol. 2011;31(17):3616-3629.
Belikov, V.G., Pharmaceutical Chemistry, 4th Ed., Medpress-inform, 622:11 (2007) with English translation (8 pages).
Bi et al. ER stress-regulated translation increases tolerance to extreme hypoxia and promotes tumor growth. EMBO J. 2005;24(19):3470-3481.
Bibha Dahal et al: "PERK is Critical for Alphavirus Nonstructural Protein Translation", Viruses, vol. 13, No. 5, May 12, 2021, p. 892 (17 pages).
Blais JD, Filipenko V, Bi M, et al. Activating transcription factor 4 is translationally regulated by hypoxic stress. Mol Cell Biol. 2004;24(17):7469-7482.
Cella, D. Quality of life in patients with metastatic renal cell carcinoma: The importance of patient-reported outcomes. Cancer Treat Rev. 2009;35(8):733-737.
Chapman E et al: "A small molecule inhibitor selective for a variant ATP-binding site of the chaperonin Gro-EL", Bioorganic & Medicinal Chemistry Letters, vol. 19, No. 3, Feb. 1, 2009, pp. 811-813 (7 pages).
Chen X, Iliopoulos D, Zhang Q, et al. XBP1 promotes triple-negative breast cancer by controlling the HIF1a pathway. Nature. 2014;508(7494):103-107 (29 pages).
Chevet E, Hetz C, Samali A. Endoplasmic reticulum stress-activated cell reprogramming in oncogenesis. Cancer Discov. 2015;5(6):586-597 (29 pages).
Choueiri TK, Motzer RJ. Systemic Therapy for Metastatic Renal-Cell Carcinoma. N Engl J Med. 2017;376(4):354-366.
Chow W.H., Devesa S.S., Warren J.L., Fraumeni J.F. Rising incidence of renal cell cancer in the United States. JAMA. 1999;281(17):1628-1631.
De Groot S, Redekop Wek, Verstegh MM, et al. Health-related quality of life and its determinants in patients with metastatic renal cell carcinoma. Qual Life Res. 2018;27(1):115-124.
Dey S, Sayers CM, Verginadis II, et al. ATF4-dependent induction of heme oxygenase 1 prevents anoikis and promotes metastasis. J Clin Invest. 2015; 125(7):2592-2608.
Diamond E, Molina AM, Carbonaro M, et al. Cytotoxic chemotherapy in the treatment of advanced renal cell carcinoma in the era of targeted therapy. Critical Review Oncol Hematol. 2015;96(3):518-526.
Escudier B, Eisen T, Porta C, et al. Renal cell carcinoma: ESMO Clinical Practice Guidelines for diagnosis, treatment and follow-up. Ann Oncol. 2012, 23(7), vii65-vii75 (7 pages).
Escudier B, Eisen T, Stadler WM, et al. Sorafenib in advanced clear-cell renal-cell carcinoma. N Engl J Med. 2007;356(2):125-134.
Feng YX, Jin DX, Sokol ES, et al. Cancer-specific PERK signaling drives invasion and metastasis through CREB3L1. Nat Commun. 2017;8(1):1079 (10 pages).
Feng YX, Sokol ES, Del Vecchio CA, et al. Epithelial-to-mesenchymal transition activates PERK-elF2α and sensitizes cells to endoplasmic reticulum stress. Cancer Discov. 2014;4(6):702-715.
Ferlay J, Ervik M, Lam F, et al. Global Cancer Observatory: Cancer Today. Lyon: International Agency for Research on Cancer; 2020 (10 pages).
Fusco V, Parisi S, d'Andrea B, et al. Role of radiotherapy in the treatment of renal cell cancer: updated and critical review. 2017; 103(6):504-510.
Guidance for Industry, Estimating the Maximum Safe Starting Dose in Initial Clinical Trials for Therapeutics in Adult Healthy Volunteers. U.S. Department of Health and Human Services, Food and Drug Administration, Center for Drug Evaluation and Research (CDER), Jul. 2005 (30 pages).
Han KS, Li N, Raven PA, et al. Inhibition of endoplasmic reticulum chaperone protein glucose-regulated protein 78 potentiates anti-angiogenic therapy in renal cell carcinoma through inactivation of the PERK/elF2α pathway. Oncotarget. 2015;6(33):34818-34830.
Harding HP, Zhang Y, Ron D. Protein translation and folding are coupled by an endoplasmic reticulum-resident kinase. Nature. 1999;397(6716):271-274 (5 pages).
Hart LS, Cunningham JT, Datta T, et al. ER stress-mediated autophagy promotes Myc-dependent transformation and tumor growth. J Clin Invest. 2012;122(12):4621-4634.
Hsieh JJ, Purdue MP, Signoretti S, et al. Renal cell carcinoma. Nat Rev Dis Primers. 2017; 3:17009 (42 pages).
International Search Report and Written Opinion in PCT/US2020/048621, dated May 11, 2020 (12 pages).
Iriyama N, Hino H, Moriya S, et al. The cyclin-dependent kinase 4/6 inhibitor, abemaciclib, exerts dose-dependent cytostatic and cytocidal effects and induces autophagy in multiple myeloma cells. Leuk Lymphoma. 2018;59(6):1439-1450 (13 pages).
Janowitz T, Welsh SJ, Zaki K, et al. Adjuvant therapy in renal cell carcinoma-past, present, and future. Semin Oncol. 2013;40(4):482-491.
Jeffrey M. Axten et al: "Discovery of 7-Methyl-5-(1-{[3-(trifluoromethyl)phenyl]acetyl}-2,3-dihydro-1H-indol-5-yl)-7H-pyrrolo92,3-d]pyrimidin-4-amine (GSK2606414), a Potent and Selective First-in-Class Inhibitor of Protein Kinase R (PKR)-like Endoplasmic

(56) References Cited

OTHER PUBLICATIONS

Reticulum Kinase (PERK)", Journal of Medicinal Chemistry, vol. 55, No. 16, Aug. 23, 2012, pp. 7193-7207.
Jeffrey M. Axten et al: "Discovery of GSK2656157: An Optimized PERK Inhibitor Selected for Preclinical Development", ACS Medicinal Chemistry Letters, vol. 4, No. 10, Aug. 23, 2013, pp. 964-968.
Jeffrey M. Axten: "Protein kinase R (PKR)-like endoplasmic reticulum kinase (PERK) inhibitors: a patent review (2010-2015)", Expert Opinion on Therapeutic Patents, vol. 27, No. 1, Jan. 2, 2017, pp. 37-48.
Kamli H, Li L, Gobe GC. Limitations to the Therapeutic Potential of Tyrosine Kinase Inhibitors and Alternative Therapies for Kidney Cancer. Ochsner J. 2019;19(2):138-151.
Ko JJ, Choueiri TK, Rini BI, et al. First-, second-, third-line therapy for mRCC: benchmarks for trial design from the IMDC. Br J Cancer. 2014;110(8):1917-1922.
Kotecha RR, Motzer RJ, Voss MH. Towards individualized therapy for metastatic renal cell carcinoma Nat Rev Clin Oncol. 2019;16(10):621-633.
Kummerer, K., "Pharmaceuticals in the Environment," Ann. Rev. Environ. Res., 2010;35:57-75 (25 pages).
Kuo CY, Lin CH, Hsu T, et al. VHL inactivation in precancerous kidney cells induces an inflammatory response via ER stress-activated IRE1a signaling. Cancer Res. 2017;77(13):3406-3416.
Lane et al. Growth kinetics and active surveillance for small renal masses. Curr Opin Urol. 2012;22(5):353-359.
Li Chuansheng et al: "Discovery of novel anti-angiogenesis agents. Part 7: Multitarget inhibitors of VEGFR-2 TIE-2 and EphB4", European Journal of Medicinal Chemistry, vol. 141, Oct. 12, 2017, 506-518.
Li et al. CCT020312 inhibits triple-negative breast cancer through PERK pathway-mediated G1 phase cell cycle arrest and apoptosis. Front Pharmacol. 2020;11:737 (12 pages).
Ljungberg B, Bensalah K, Canfield St, et al. EAU guidelines on renal cell carcinoma: 2014 update. Eur Urol. 2015;67(5):913-924.
Low et al. Review of renal cell carcinoma and its common subtypes in radiology. World J Radiol. 2016;8(5):484-500 (18 pages).
Lydia P. Liew et al: "Hypoxia-Activated Prodrugs of PERK Inhibitors", Chemistry—An Asian Journal, vol. 14, No. 8, Jan. 29, 2019, pp. 1238-1248.
Makhov et al. The convergent roles of NF-κB and ER stress in sunitinib-mediated expression of pro-tumorigenic cytokines and refractory phenotype in renal cell carcinoma. Cell Death Dis. 2018;9(3):374 (9 pages).
Martín-Pérez et al. Activated ERBB2/HER2 licenses sensitivity to apoptosis upon endoplasmic reticulum stress through a PERK-dependent pathway. Cancer Res. 2014;74(6):1766-1777.
Moch et al. The 2016 WHO Classification of Tumours of the Urinary System and Male Genital Organs—Part A: Renal, Penile, and Testicular Tumours. Eur Urol. 2016; 70(1):93-105.
Mollica et al. Pembrolizumab plus axitinib: a new treatment option for patients with metastatic renal cell carcinoma. Chin Clin Oncol 2019;8(S1):S21 (4 pages).
Motzer RJ, Hutson TE, Tomczak P, et al. Sunitinib versus interferon alpha in metastatic renal-cell carcinoma. N Engl J Med. 2007;356(2):115-124.
Motzer RJ, Jonasch E, et al. Kidney Cancer, Version 2.2017, NCCN Clinical Practice Guidelines in Oncology. J Natl Compr Canc Netw. 2017;15(6):804-834.
Motzer RJ, Jonasch E, Agarwal N, et al. Kidney cancer, version 3.2015. J Natl Compr Canc Netw. 2015;13(2):151-159.
Motzer RJ, Jonasch E, Boyle S, et al. Kidney Cancer, Version 1.2021 Featured Updates to the NCCN Guidelines. J Natl Compr Can Netw. 2020;18(9):1160-1170.
Motzer RJ, Jonasch E, Michaelson MD, et al. NCCN Guidelines Insights: Kidney Cancer, Version 2.2020. J Natl Compr Canc Netw. 2019; 17(11):1278-1285.
Nabi S, Kessler E, Bernard B, et al. Renal cell carcinoma: a review of biology and pathophysiology. F1000 Res. 2018;7:307 (10 pages).
Nagelkerke A, Bussink J, Mujcic H, et al. Hypoxia stimulates migration of breast cancer cells via the PERK/ATF4/LAMP3-arm of the unfolded protein response. Breast Cancer Research 2013, 15:R2, 1-13.
Novoa I, Zhang Y, Zeng H, et al. Stress-induced gene expression requires programmed recovery from translational repression. EMBO J. 2003;22(5):1180-1187.
Ojha R, Amaravadi RK. Targeting the unfolded protein response in cancer. Pharmacol Res. 2017;120:258-266 (21 pages).
Ozcan U, Ozcan L, Yilmaz E, et al. Loss of the tuberous sclerosis complex tumor suppressors triggers the unfolded protein response to regulate insulin signaling and apoptosis. Mol Cell. 2008;29(5):541-551.
Pommier A, Anaparthy N, Memos N, Kelley ZL, Gouronnec A, Yan R, Auffray C, Albregues J, Egeblad M, lacobuzio-Doonahue CA, Lyons SK, Feron DT. Unresolved endoplasmic reticulum stress engenders immune-resistant, latent pancreatic cancer metastases. Science. 2018;360(6394) (26 pages).
Rajasekhar VK, Holland EC. Postgenomic global analysis of translational control induced by oncogenic signaling. Oncogene. 2004;23(18):3248-3264.
Rajasekhar VK, Viale A, Socci ND, et al. Oncogenic Ras and Akt signaling contribute to glioblastoma formation by differential recruitment of existing mRNAs to polysomes. Mol Cell. 2003;12(4):889-901.
Ranganathan AC, Ojha S, Kourtidis A, Conklin DS, Aguirre-Ghiso JA. Dual function of pancreatic endoplasmic reticulum kinase in tumor cell growth arrest and survival. Cancer Res 2008; 68(9):3260-3268.
Rodler S, Schott M, Tamalunas A, et al. Safety and Efficacy of Robotic Radiosurgery for Visceral and Lymph Node Metastases of Renal Cell Carcinoma: A Retrospective, Single Center Analysis. Cancers (Basel). 2021;13(4):680 (9 pages).
Rojo F, Najera L, Lirola J, etc. 4E-binding protein 1, a cell signaling hallmark in breast cancer that correlates with pathologic grade and prognosis. Clin Cancer Res. 2007;13(1):81-89.
Romero-Ramirez L, Cao H, Regalado MP, et al. X box-binding protein 1 regulates angiogenesis in human pancreatic adenocarcinomas. Transl Oncol. 2009;2(1):31-38 (10 pages).
Rouschop KM, Dubois LJ, Keulers TG, et al. PERK/elF2a signaling protects therapy resistant hypoxic cells through induction of glutathione synthesis and protection against ROS. Proc Natl Acad Sci USA. 2013;110(12):4622-4627.
Rouschop KM, Van Den Beucken T, Dubois L, et al. The unfolded protein response protects human tumor cells during hypoxia through regulation of the autophagy genes MAP1LC3B and ATG5. J Clin Invest. 2010;120(1):127-141.
Ryo Kunimoto et al: "Combining Similarity Searching and Network Analysis for the Identification of Active Compounds", ACS Omega, vol. 3, No. 4, Apr. 3, 2018, 3768-3777.
Sanchez-Gastaldo A, Kempf E, Gonzalez del Alba A, Duran I. Systemic treatment of renal cell cancer: A comprehensive review. Cancer Treat Rev. 2017;60:77-89.
Sandoval et al., "Inhibition as a possible therapy for hypoxia-induced solidary dormant tumor cells" Abstract A45, Proceedings of the AACR Special Conference on Tumor Metastasis, vol. 76, No. 7, Nov. 30, 2015 (3 pages).
Schewe DM, Aguirre-Ghiso JA. ATF6alpha-Rheb-mTOR signaling promotes survival of dormant tumor cells in vivo. Proc Nat Acad Sci USA. 2008;105(30):10519-10524.
Sepe P, Mennitto A, Corti F, Procopio G. Immunotherapeutic Targets and Therapy for Renal Cell Carcinoma. Immunotargets Ther. 2020;9:273-288.
Sequeira SJ, Wen HC, Avivar-Valderas A, et al. Inhibition of elF2α dephosphorylation inhibits ErbB2-induced deregulation of mammary acinar morphogenesis. BMC Cell Biol. 2009;10(1):64 (14 pages).
Shan Yuanyuan et al: "Expanding the structural diversity of diarylureas as multi-target tyrosine kinase inhibitors", Bioorganic & Medicinal Chemistry, vol. 24, No. 4, Dec. 23, 2015, pp. 750-758.
Siva S, Kothari G, Muacevic A, et al. Radiotherapy for renal cell carcinoma: renaissance of an overlooked approach. Nat Rev Urol. 2017;14(9):549-563.

(56) References Cited

OTHER PUBLICATIONS

Sosa et al., "Mechanisms of disseminated cancer cell dormancy: an awakening field" Nature Reviews. Cancer, vol. 14, No. 9, Aug. 14, 2014, pp. 611-622 (27 pages).

Sternberg CN, Davis ID, Mardiak J, et al. Pazopanib in locally advanced or metastatic renal cell carcinoma: results of a randomized phase III trial. J Clin Oncol. 2010;28(6):1061-1068.

Sujata Chakraborty et al: "Targeting Dynamic ATP-Binding Site Features Allows Discrimination between Highly Homologous Protein Kinases", ACS Chemical Biology, vol. 14, No. 6, Apr. 30, 2019, 1249-1259 (19 pages).

Surveillance, Epidemiology, and End Results (SEER) Program. Cancer Stat Facts: Kidney and Renal Pelvis Cancer. Available at: https://seer.cancer.gov/statfacts/html/kidrp.html (12 pages).

Tacconi EMC, Tuthill M, Protheroe A. Review of Adjuvant Therapies in Renal Cell Carcinoma: Evidence to Date. Onco Targets Ther. 2020;13:12301-12316.

Tameire F, Verginadis II, Koumenis C. Cell intrinsic and extrinsic activators of the unfolded protein response in cancer: mechanisms and targets for therapy. Semin Cancer Biol. 2015;33:3-15 (31 pages).

Urra H, Dufey E, Avril T, et al. Endoplasmic reticulum stress and the hallmarks of cancer. Trend Cancer. 2016;2(5):252-262 (24 pages).

Vijayaraghavan S, Karakas C, Doostan I, et al. CDK4/6 and autophagy inhibitors synergistically induce senescence in Rb positive cytoplasmic cyclin E negative cancers. Nat Commun. 2017;8(15916):1-17.

Walczak A, Gradzik K, Kabzinski J, et al. The Role of the ER-Induced UPR Pathway and the Efficacy of Its Inhibitors and Inducers in the Inhibition of Tumor Progression. Oxid Med Cell Longev. 2019;5729710 (15 pages).

Walter P, Ron D. The unfolded protein response: from stress pathway to homeostatic regulation. Science. 2011;334(6059):1081-1086 (7 pages).

Wang L, Cai W, Kong W, et al. Plasma fibrinogen as prognostic predictor in patients with metastatic renal cell carcinoma receiving target therapy. Transl Cancer Res 2018;7(6):1384-1392.

Wang X, Zhang H, Chen X. Drug resistance and combating drug resistance in cancer. Cancer Drug Resist. 2019;2(2):141-160 (27 pages).

Weir HK, Thompson TD, Soman A, et al. The Past, Present, and Future of Cancer Incidence in the United States: 1975 Through 2020. Cancer. 2015;121(11):1827-1837.

Xue Yuan et al: "Identification of Pyrrolo[2,3-d]pyrimidine-Based Derivatives as Potent and Orally Effective Fms-like Tyrosine Receptor Kinase 3 (FLT3) Inhibitors for Treating Acute Myelogenous leukemia", Journal of Medicinal Chemistry, vol. 62, No. 8, Apr. 2, 2019, 4158-4173.

Yan Li et al: "AutoT&T v.2: An Efficient and Versatile Tool for Lead Structure Generation and Optimization", Journal of Chemical Information and Modeling, vol. 56, No. 2, Feb. 22, 2016, 435-453.

Yang DC, Chen CH. Potential New Therapeutic Approaches for Renal Cell Carcinoma. Semin Nephrol. 2020;40(1):86-97 (13 pages).

Ye J, Kumanova M, Hart LS, et al. The GCN2-ATF4 pathway is critical for tumour cell survival and proliferation in response to nutrient deprivation. EMBO J. 2010;29(12):2082-2096.

Yoo YS, Han HG, Jeon YJ. Unfolded Protein Response of the Endoplasmic Reticulum in Tumor Progression and Immunogenicity. Oxid Med Cell Longev. 2017;2969271 (18 pages).

Yueshan Li et al: "Identification of 5-(2,3-Dihydro-1H-indol-5-yl)-7H-pyrrolo[2,3-d]pyrimidin-4-amine Derivatives as a New Class of Receptor-Interacting Protein Kinase 1 (RIPK1) Inhibitors, Which Showed Potent Activity in a Tumor Metastasis Model", Journal of Medicinal Chemistry, vol. 61, No. 24, Nov. 27, 2018, 61(24), 11398-11414.

Zhang et al. Immune infiltration in renal cell carcinoma. Cancer Sci. 2019; 110(5):1564-1572.

Siegel RL, Miller KD, Jemal A. CA Cancer J Clin. 2020;70(1):7-30.

Shan Yuan et al: "Expanding the structural diversity of diarylureas as multi-target tyrosine kinase inhibitors", Bioorganic & Medicinal Chemistry, Elsevier, NL, vol. 24, No. 4, Dec. 23, 2015, 750-758.

U.S. Appl. No. 17/639,169 US 2022/0332722, Perk Inhibiting Compounds, filed Feb. 28, 2022, Published.

U.S. Appl. No. 17/639,183 US 2022/0348583, Perk Inhibiting Imidazolopyrazine Compounds, filed Feb. 28, 2022, Published.

U.S. Appl. No. 17/639,269 US 2022/0348584, Perk Inhibiting Indolinyl Compounds, filed Feb. 28, 2022, Published.

* cited by examiner

PERK INHIBITING PYRROLOPYRIMIDINE COMPOUNDS

CROSS-REFERENCE TO RELATED APPLICATIONS

This application is a U.S. national stage patent application under 35 U.S.C. § 371 of International Application No. PCT/US2020/048621, filed on Aug. 28, 2020, which application claims the benefit of and priority to U.S. Provisional Patent Application No. 62/893,528, filed on Aug. 29, 2019, each of which is incorporated herein by reference in its entirety.

BACKGROUND OF THE INVENTION

Embodiments of the present invention relate to novel pyrrolopyrimidine compounds, to pharmaceutical compositions comprising the compounds, to methods of using the compounds to treat physiological disorders, and to intermediates and processes useful in the synthesis of the compounds. The present invention is in the field of treatment of cancer and, other diseases and disorders involving protein kinase R (PKR)-like endoplasmic reticulum kinase (PERK).

PERK, an eIF2 kinase involved in the unfolded protein response (UPR) regulates protein synthesis, aids cells to alleviate the impact of endoplasmic reticulum stress and has been implicated in tumor genesis and cancer cell survival.

Tumor cells thrive in a hostile microenvironment caused mainly by nutrient and oxygen limitation, high metabolic demand, and oxidative stress. These stresses are known to disrupt the protein folding capacity of the endoplasmic reticulum (ER) eliciting a cellular remediation response known as the UPR. The UPR serves as a mechanism for cellular survival whereby cells are able to adapt to cope with ER stress, but under extreme stress the UPR switches the cellular machinery toward apoptosis, contributing to greater tumorigenic potential of cancer cells, tumor metastasis, tumor drug resistance, and the ability of cancer cells to avoid effective immune responses. Tumors are believed to utilize the UPR for survival under stressed conditions such as nutrient deprivation or treatment with chemotherapy. Other stress stimuli that activate UPR include hypoxia, disruption of protein glycosylation, depletion of luminal ER calcium, or changes in ER redox status.

There are three major ER transmembrane sensors of the UPR: 1) inositol requiring enzyme (IREla/IREip, encoded by ERN1 and ERN2, respectively); 2) PKR-like ER kinase (PERK, also known as PEK, encoded by EIF2AK3); and 3) the activating transcription factor 6a (encoded by ATF6). Each of these three sensors is regulated similarly through binding of the ER luminal chaperone protein GRP78 or BiP (encoded by HSPA5). When protein folding demands of the ER exceed capacity, reduced BiP binding results in activation of these ER sensor proteins resulting in the induction of coordinated signaling pathways to increase the folding capacity of the ER and alleviate the underlying stress. Effective responses lead to cell adaptation and survival while irreparable ER stress triggers cell death and apoptosis.

PERK is a type I transmembrane serine/threonine kinase and a member of a family of kinases that phosphorylate the eukaryotic translation initiation factor 2a (eIF2-a) and regulate translation initiation. Other family members include HRI (EIF2AK1), PKR (EIF2AK2), and GCN2 (EIF2AK4). Each eIF2 kinase responds to different cellular stress signals to regulate general translation and gene specific translational control.

PERK is an ER transmembrane protein with a stress-sensing domain inside the ER lumen and a cytosolic kinase domain. Upon sensing misfolded proteins, PERK is activated by autophosphorylation and oligomerization through release of BiP/Grp78 from the stress-sensing domain. Activated PERK phosphorylates and activates its downstream substrate, eukaryotic initiation factor 2a (eIF2a), which inhibits the ribosome translation initiation complex in order to attenuate protein synthesis. This serves to prevent exacerbation of ER stress by preventing the accumulation of additional misfolded proteins. Although it inhibits general protein synthesis, activated eIF2a causes the translation of specific mRNAs involved in restoring ER homeostasis including activating transcription factor 4 (ATF4). ATF4 mediates the transcription of certain UPR target genes including those for the endoplasmic-reticulum-associated protein degradation (ERAD) pathway proteins which target misfolded proteins for ubiquitination and degradation by the proteasome. ATF4 also causes the expression of the transcription factor C/EBP homologous protein (CHoP), which sensitizes cells to ER stress-mediated apoptosis, providing a pathway for regulated removal of severely stressed cells by the organism.

Phosphorylation of eIF2 results in reduced initiation of general translation due to a reduction in eIF2B exchange factor activity decreasing the amount of protein entering the ER (and thus the protein folding burden) and translational demand for ATP.

Phosphorylation of eIF2 also increases translation of some mRNAs in a gene specific manner including the transcription factor ATF4. ATF4 transcriptional targets include numerous genes involved in cell adaptation and survival including several involved in protein folding, nutrient uptake, amino acid metabolism, redox homeostasis, and autophagy. Selective inhibition of the PERK arm of the UPR is expected to profoundly affect tumor cell growth and survival. As such, compounds which inhibit PERK are believed to be useful in treating cancer.

SUMMARY OF THE INVENTION

Figure 1:
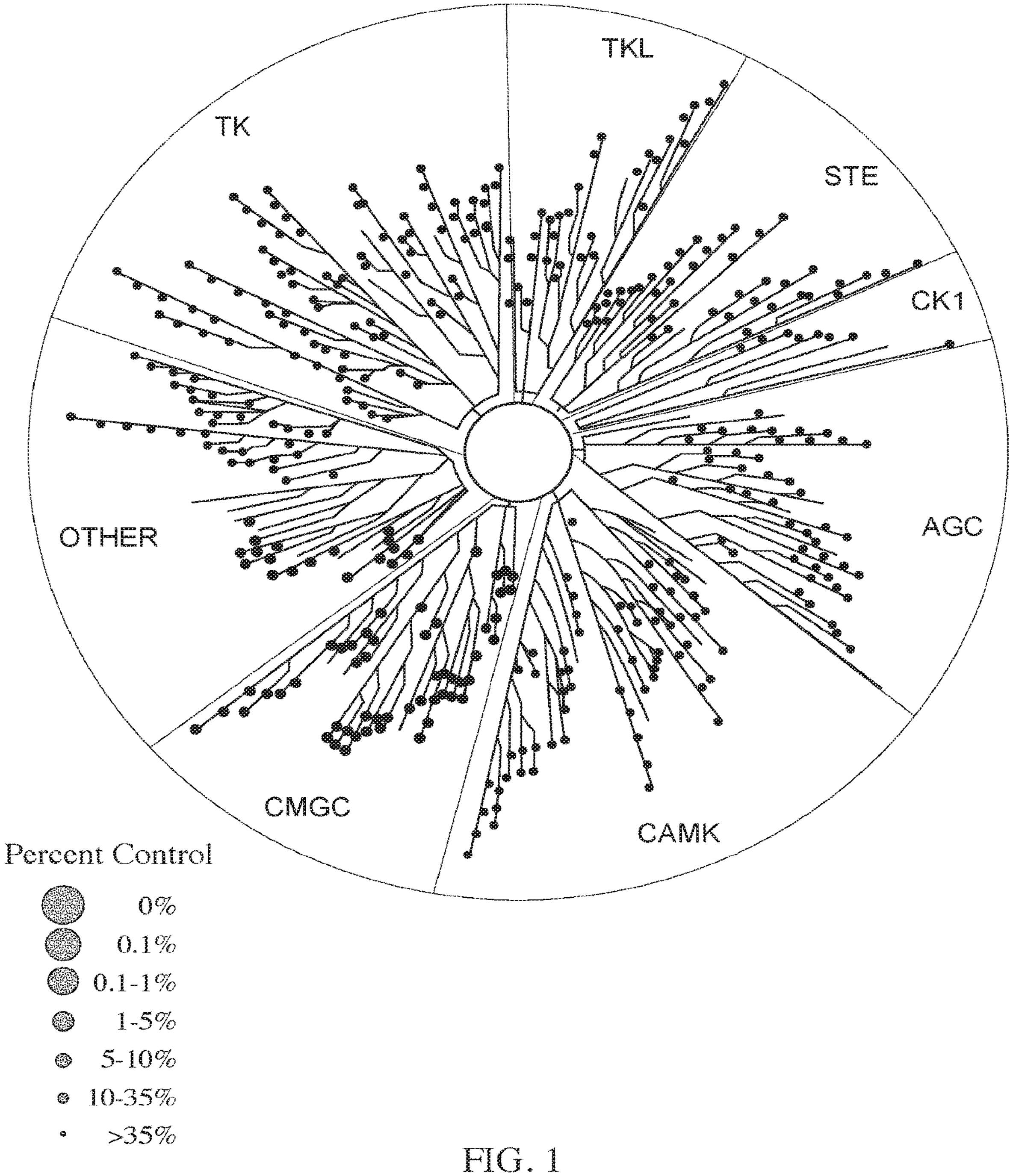
FIG. 1 illustrates a kinase selectivity interaction map for Example 1.

Embodiments of the present invention provide a compound having the structure (I):

(I)

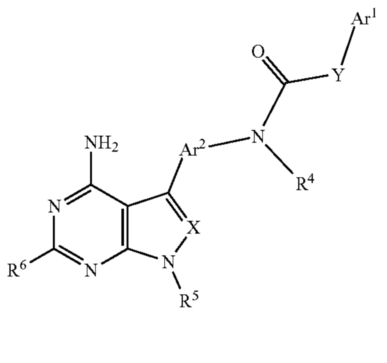

wherein:

$Ar^1$ is aryl, heteroaryl, or cycloalkyl, optionally substituted by one or more independent $R^1$ substituents;

$Ar^2$ is aryl or heteroaryl, optionally substituted by one or more independent $R^2$ substituents;

Y is $C(R^{3a})(R^{3b})C_{0-2}$alkyl, —O—, $NR^{3a}$, C(O), $CF_2$, $CNOR^{3bb}$, or a direct bond to $Ar^1$;

$R^{3a}$ is H, alkyl, or cycloalkyl;

$R^{3b}$ is H, alkyl, $OR^{3c}$, or $NR^{3d}R^{3e}$;

$R^{3bb}$ is H or alkyl;

$R^4$ is H, alkyl, or OH;

X is $CR^7$ or N;

$R^1$ is one or more independent H, deuterium, halo, CN, $NO_2$, alkyl, cycloalkyl, $C_{0-6}$alkyl-O—$C_{1-12}$alkyl, $C_{0-6}$alkyl-OH, $C_{0-6}$alkyl-O—$C_{3-12}$cycloalkyl, or $C_{0-6}$alkyl-O—$C_{3-12}$heterocycloalkyl, optionally substituted by one or more independent $G^1$ substituents;

$R^2$ is one or more independent H, deuterium, halo, CN, $NO_2$, alkyl, $C_{0-6}$alkylcycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^2$ substituents;

$R^{3c}$, $R^{3d}$ and $R^{3e}$ are each independently H, alkyl, or cycloalkyl, optionally substituted by one or more independent $G^3$ substituents;

$R^5$ is H, alkyl, cycloalkyl, or heterocycloalkyl, optionally substituted by one or more independent $G^4$ substituents;

$R^6$ is H, alkyl, $CD_3$, or $CF_3$;

$R^7$ is H, CN, or alkyl, optionally substituted by one or more independent deuterium or halo;

$G^1$, $G^2$, $G^3$, or $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, $C(O)R^8$, $C(O)OR^{B}$, $C(O)NR^8R^9$, $OC(O)R^8$, $OC(O)OR^8$, $OC(O)NR^8R^9$, $N(R^{10})C(O)R^8$, $N(R^{10})C(O)OR^8$, $N(R^{10})C(O)NR^8R^9$, $S(O)_nR^8$, $S(O)_nOR^8$, $S(O)_nNR^8R^9$, $N(R^{10})S(O)_nR^8$, $N(R^{10})S(O)_nOR^8$, or $N(R^{10})S(O)_nNR^8R^9$, optionally substituted by one or more independent H, deuterium, halo, OH, CN, or $NO_2$;

$R^8$, $R^9$, or $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;

n is 0, 1, or 2;

or a pharmaceutically acceptable salt thereof.

DETAILED DESCRIPTION OF THE INVENTION

With the current state of medical treatment, patients developing cancer often have a poor prognosis even if the disease is detected early. As such, there remains a significant need for new and effective therapies to treat cancer. The compounds of the present invention are inhibitors of PERK, and are believed to be useful in treating cancer.

The present invention provides a compound having the structure (I):

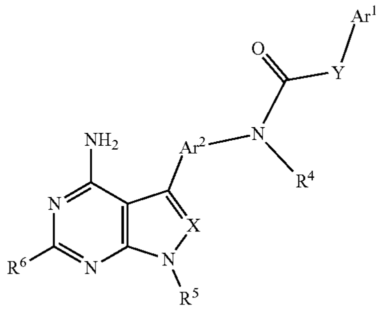

(I)

wherein:

$Ar^1$ is aryl, heteroaryl, or cycloalkyl, optionally substituted by one or more independent $R^1$ substituents;

$Ar^2$ is aryl or heteroaryl, optionally substituted by one or more independent $R^2$ substituents;

Y is $C(R^{3a})(R^{3b})C_{0-2}$alkyl, —O—, $NR^{3a}$, C(O), $CF_2$, $CNOR^{3bb}$, or a direct bond to $Ar^1$;

$R^{3a}$ is H, alkyl, or cycloalkyl;

$R^{3b}$ is H, alkyl, $OR^{3c}$, or $NR^{3d}R^{3e}$;

$R^{3bb}$ is H or alkyl;

$R^4$ is H, alkyl, or OH;

X is $CR^7$ or N;

$R^1$ is one or more independent H, deuterium, halo, CN, $NO_2$, alkyl, cycloalkyl, $C_{0-6}$alkyl-O—$C_{1-12}$alkyl, $C_{0-6}$alkyl-OH, $C_{0-6}$alkyl-O—$C_{3-12}$cycloalkyl, or $C_{0-6}$alkyl-O—$C_{3-12}$heterocycloalkyl, optionally substituted by one or more independent $G^1$ substituents;

$R^2$ is one or more independent H, deuterium, halo, CN, $NO_2$, alkyl, $C_{0-6}$alkylcycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^2$ substituents;

$R^{3c}$, $R^{3d}$ and $R^{3e}$ are each independently H, alkyl, or cycloalkyl, optionally substituted by one or more independent $G^3$ substituents;

$R^5$ is H, alkyl, cycloalkyl, or heterocycloalkyl, optionally substituted by one or more independent $G^4$ substituents;

$R^6$ is H, alkyl, $CD_3$, or $CF_3$;

$R^7$ is H, CN, or alkyl, optionally substituted by one or more independent deuterium or halo;

$G^1$, $G^2$, $G^3$, or $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, $C(O)R^8$, $C(O)OR^8$, $C(O)NR^8R^9$, $OC(O)R^8$, $OC(O)OR^8$, $OC(O)NR^8R^9$, $N(R^{10})C(O)R^8$, $N(R^{10})C(O)OR^8$, $N(R^{10})C(O)NR^8R^9$, $S(O)_nR^8$, $S(O)_nOR^8$, $S(O)_nNR^8R^9$, $N(R^{10})S(O)_nR^8$, $N(R^{10})S(O)_nOR^8$, or $N(R^{10})S(O)_nNR^8R^9$, optionally substituted by one or more independent H, deuterium, halo, OH, CN, or $NO_2$;

$R^8$, $R^9$, or $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;

n is 0, 1, or 2;

or a pharmaceutically acceptable salt thereof.

In some embodiments, a pharmaceutical composition comprising the compound of the present invention and a pharmaceutically acceptable carrier.

In some embodiments, a pharmaceutical composition comprising the compound of the present invention, an anti-cancer agent and a pharmaceutically acceptable carrier.

The present invention provides a method of inhibiting the growth of a tumor comprising contacting a tumor cell with an effective amount of the compound of the present invention or a pharmaceutically acceptable salt, so as to thereby inhibit the growth of the tumor.

The present invention further provides a method of inhibiting the growth of a tumor comprising contacting a tumor cell with an effective amount of the compound of the present invention or a pharmaceutically acceptable salt, in combination with an anti-cancer agent, so as to thereby inhibit the growth and/or metastasis of the tumor.

The present invention also provides a method of inhibiting PERK comprising contacting the tumor cell with an effective amount of the compound of the present invention or a pharmaceutically acceptable salt.

In some embodiments of the method, further comprising contacting the tumor cell with an effective amount of an anti-cancer agent.

In some embodiments of the method, further comprising administering to the mammal an effective amount of an anti-cancer agent.

The present invention yet further provides a compound having the following structure (Ia):

(Ia)

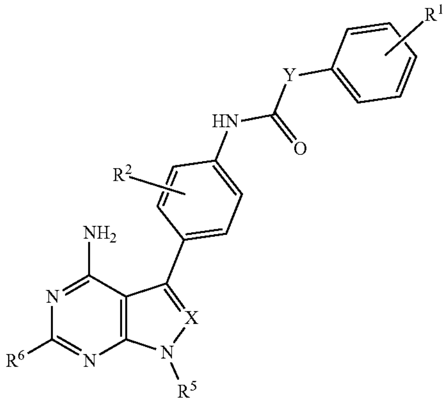

wherein:

Y is $CR^{3a}R^{3b}$;

$R^{3a}$ is H or alkyl;

$R^{3b}$ is $OR^{3c}$ or $NR^{3d}R^{3e}$.

$R^1$ is one or more independent H, deuterium, halo, alkyl, cycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^1$ substituents;

$R^2$ is one or more independent H, deuterium, halo, alkyl, $C_{0-6}$alkylcycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^2$ substituents;

$R^{3c}$, $R^{3d}$ and $R^{3e}$ are each independently H or alkyl, optionally substituted by one or more independent $G^3$ substituents;

X is $CR^7$ or N;

$R^5$ is H, alkyl, cycloalkyl, or heterocycloalkyl, optionally substituted by one or more independent $G^4$ substituents;

$R^6$ is H, alkyl, $CD_3$, or $CF_3$;

$R^7$ is H, CN, or alkyl, optionally substituted by one or more independent deuterium or halo;

$G^1$, $G^2$, $G^3$, or $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, $C(O)R^8$, $C(O)OR^8$, $C(O)NR^8R^9$, $OC(O)R^8$, $OC(O)OR^8$, $OC(O)NR^8R^9$, $N(R^{10})C(O)R^5$, $N(R^{10})C(O)OR^8$, $N(R^{10})C(O)NR^8R^9$, $S(O)_nR^8$, $S(O)_nOR^8$, $S(O)_nNR^8R^9$, $N(R^{10})S(O)_nR^8$, $N(R^{10})S(O)_nOR^8$, or $N(R^{10})S(O)_nNR^8R^9$, optionally substituted by one or more independent H, deuterium, halo, OH, CN, or $NO_2$;

$R^8$, $R^9$, or $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;

n is 0, 1, or 2;

or a pharmaceutically acceptable salt thereof.

The present invention yet further provides a compound having the following structure (Ib):

(Ib)

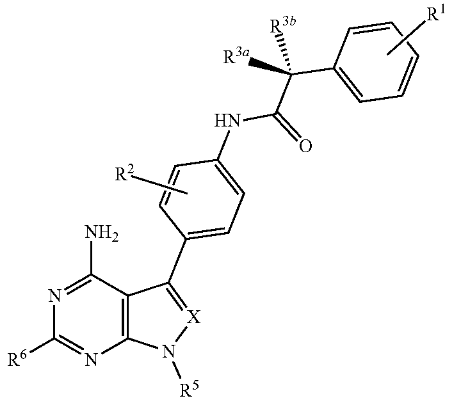

wherein:

X is CH or N;

$R^1$ is one or more independent H, deuterium, halo, alkyl, cycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^1$ substituents;

$R^2$ is one or more independent H, deuterium, halo, alkyl, cycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^2$ substituents;

$R^3$ is H or alkyl;

$R^{3b}$ is $OR^{3c}$ or $NR^{3d}R^{3e}$.

$R^{3c}$, $R^{3d}$ and $R^{3e}$ are each independently H or alkyl, optionally substituted by one or more independent $G^3$ substituents;

$R^5$ is H, alkyl, cycloalkyl, or heterocycloalkyl, optionally substituted by one or more independent $G^4$ substituents;

$R^6$ is H, alkyl, $CD_3$, or $CF_3$;

$G^1$, $G^2$, $G^3$, or $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, $C(O)R^8$, $C(O)OR^8$, $C(O)NR^8R^9$, $OC(O)R^8$, $OC(O)OR^8$, $OC(O)NR^8R^9$, $N(R^{10})C(O)R^8$, $N(R^{10})C(O)OR^8$, $N(R^{10})C(O)NR^8R^9$, $S(O)_nR^8$, $S(O)_nOR^8$, $S(O)_nNR^8R^9$, $N(R^{10})S(O)_nR^8$, $N(R^{10})S(O)_nOR^8$, or $N(R^{10})S(O)_nNR^8R^9$, optionally substituted by one or more independent H, deuterium, halo, OH, CN, or $NO_2$;

$R^8$, $R^9$, or $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;

n is 0, 1, or 2;

or a pharmaceutically acceptable salt thereof.

The present invention yet further provides a compound having the following structure (Ic):

(Ic)

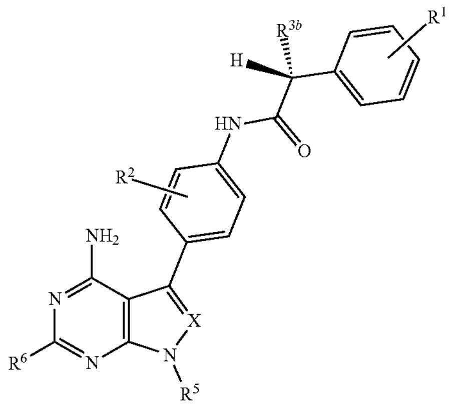

wherein:

X is CH or N;

$R^1$ is one or more independent H, deuterium, halo, alkyl, $C_{0-6}$alkyl-OH, or $C_{0-6}$alkyl-O—$C_{1-12}$alkyl, optionally substituted by one or more independent $G^1$ substituents;

$R^2$ is one or more independent H, deuterium, halo, alkyl, $C_{0-6}$alkyl-OH, or $C_{0-6}$alkyl-O—$C_{1-12}$alkyl, optionally substituted by one or more independent $G^2$ substituents;

$R^{3b}$ is $OR^{3c}$.

$R^{3c}$ is H or alkyl, optionally substituted by one or more independent $G^3$ substituents;

$R^5$ is H, alkyl, cycloalkyl, or heterocycloalkyl, optionally substituted by one or more independent $G^4$ substituents;

$R^6$ is H, alkyl, $CD_3$, or $CF_3$;

$G^1$, $G^2$, $G^3$, or $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, C(O)$R^8$, C(O)$OR^8$, C(O)$NR^8R^9$, OC(O)$R^8$, OC(O)$OR^8$, OC(O)$NR^8R^9$, N($R^{10}$)C(O)$R^8$, N($R^{10}$)C(O)$OR^8$, N($R^{10}$)C(O)$NR^8R^9$, $S(O)_nR^8$, $S(O)_nOR^8$, $S(O)_nNR^8R^9$, N($R^{10}$)$S(O)_nR^8$, N($R^{10}$)$S(O)_nOR^8$, or N($R^{10}$)$S(O)_nNR^8R^9$, optionally substituted by one or more independent H, deuterium, halo, OH, CN, or $NO_2$;

$R^8$, $R^9$, or $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;

n is 0, 1, or 2;

or a pharmaceutically acceptable salt thereof.

The present invention yet further provides a compound having the following structure (Id):

(Id)

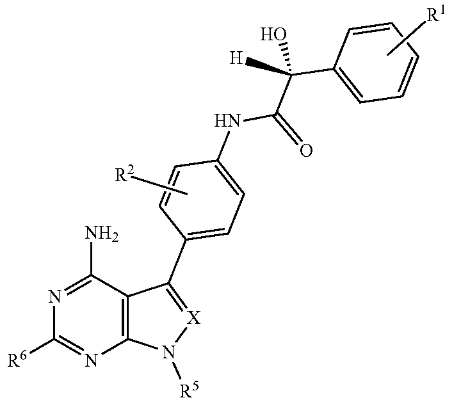

wherein:

X is CH or N;

$R^1$ is one or more independent H, deuterium, halo, alkyl, $C_{0-6}$alkyl-OH, or $C_{0-6}$alkyl-O—$C_{1-12}$alkyl, optionally substituted by one or more independent H, deuterium, or halo;

$R^2$ is one or more independent H, deuterium, halo, alkyl, $C_{0-6}$alkyl-OH, or $C_{0-6}$alkyl-O—$C_{1-12}$alkyl, optionally substituted by one or more independent H, deuterium or halo;

$R^5$ is H, alkyl, cycloalkyl, or heterocycloalkyl, optionally substituted by one or more independent H, deuterium, halo, OH, or CN;

$R^6$ is H, alkyl, $CD_3$, or $CF_3$;

or a pharmaceutically acceptable salt thereof.

The present invention yet further provides a compound having the following structure (Ie):

(Ie)

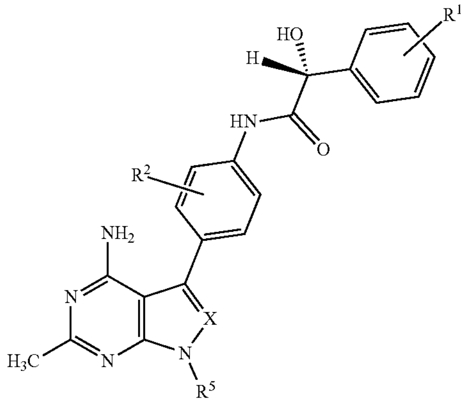

wherein:

X is CH or N;

$R^1$ is one or more independent H, deuterium, halo, alkyl, $C_{0-6}$alkyl-OH, or $C_{0-6}$alkyl-O—$C_{1-12}$alkyl, optionally substituted by one or more independent H, deuterium, or halo;

$R^2$ is one or more independent H, deuterium, halo, alkyl, $C_{0-6}$alkyl-OH, or $C_{0-6}$alkyl-O—$C_{1-12}$alkyl, optionally substituted by one or more independent H, deuterium or halo;

$R^5$ is H, methyl, ethyl, isopropyl,

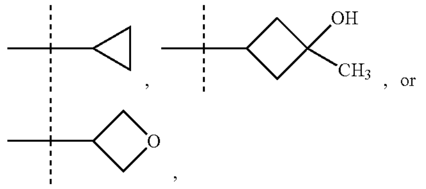

optionally substituted by one or more independent H, deuterium, $C_{1-6}$alkyl, halo, OH, or CN;

or a pharmaceutically acceptable salt thereof.

In some embodiments, X is CH.

In some embodiments, R1, for each occurrence, is H, methyl, ethyl, isopropyl, methoxy, ethoxy, propoxy, isopropoxy, deuterium, OCF3, CF3, fluoro, or chloro.

In some embodiments, R2, for each occurrence, is H, methyl, ethyl, propyl, isopropyl, methoxy, ethoxy, propoxy, isopropoxy, fluoro, chloro, CF3 or OCF3.

In some embodiments, R5 is H, CH3, or CD3.

In some embodiments, R6 is H, methyl, ethyl, isopropyl, CD3, or CF3.

In some embodiments, G1, G2, G3, or G4 are each independently H, deuterium, halo, CN, NO2, C1-6alkyl, C3-8cycloalkyl, C3-8heterocycloalkyl, OR8, NR8R9, C(O)R8, C(O)OR8, C(O)NR8R9, OC(O)R8, OC(O)OR8, OC(O)NR8R9, N(R10)C(O)R8, N(R10)C(O)OR8, N(R10)C(O)NR8R9, S(O)nR8, S(O)nOR8, S(O)nNR8R9, N(R10)S(O)nR8, N(R10)S(O)nOR8, or N(R10)S(O)nNR8R9, optionally substituted by one or more independent H, deuterium, halo, OH, CN, or NO2.

In some embodiments, G1, G2, G3, or G4 are each independently H, deuterium, halo, CN, NO2, C1-3alkyl, C3-6cycloalkyl, C3-6heterocycloalkyl, OR8, NR8R9, C(O)R8, C(O)OR8, C(O)NR8R9, OC(O)R8, OC(O)OR8, OC(O)NR8R9, N(R10)C(O)R8, N(R10)C(O)OR8, N(R10)C(O)NR8R9, S(O)nR8, S(O)nOR8, S(O)nNR8R9, N(R10)S(O)nR8, N(R10)S(O)nOR8, or N(R10)S(O)nNR8R9, optionally substituted by one or more independent H, deuterium, halo, OH, CN, or NO2.

In some embodiments, Ar1 is pyridyl, optionally substituted by one or more independent R1 substituents.

In some embodiments, Ar1 is cyclopropyl, cyclobutyl, cyclopentyl, cyclohexyl, phenyl,

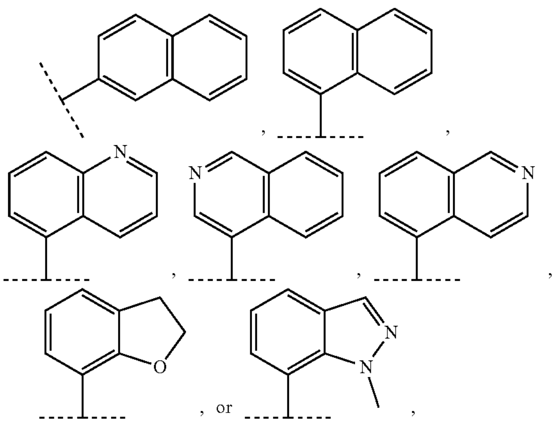

optionally substituted by one or more independent $R^1$ substituents.

In some embodiments, Ar2 is monocyclic-aryl or monocyclic-heteroaryl, optionally substituted by one or more independent $R^2$ substituents.

In some embodiments, Y is a direct bond to Ar1, —CH2-, —C(H)(OH)—, —C(CH3)(OH)—, —C(H)(—OCH3)-, —(CH2)2-, —O—, —NH—, —N(CH3)-, —C(H)(NH2)-, or —CF2-.

The present invention yet further provides a compound having the following structure (If):

(If)

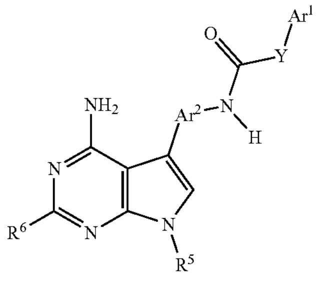

wherein:

$Ar^1$ is aryl, heteroaryl, or cycloalkyl, optionally substituted by one or more independent $R^1$ substituents;

$Ar^2$ is aryl or heteroaryl, optionally substituted by one or more independent $R^2$ substituents;

Y is $C(R^{3a})(R^{3b})C_{0-2}$alkyl, —O—, $NR^{3a}$, $CF_2$, or a direct bond to $Ar^1$;

$R^{3a}$ is H, or alkyl;

$R^{3b}$ is H, $OR^{3c}$, or $NR^{3d}R^{3e}$.

$R^1$ is one or more independent halo, alkyl, or $C_{0-6}$alkyl-O—$C_{1-12}$alkyl, optionally substituted by one or more halogen substituents;

$R^2$ is one or more independent halo, alkyl, $C_{0-6}$alkyl-O—$C_{1-12}$alkyl, optionally substituted by one or more halogen substituents;

$R^{3c}$, $R^{3d}$ and $R^{3e}$ are each independently H or alkyl;

$R^5$ is alkyl; and $R^6$ is H, alkyl, or $CF_3$;

or a pharmaceutically acceptable salt thereof.

In some embodiments, Ar1 is cyclopropyl, cyclobutyl, cyclopentyl, cyclohexyl, phenyl, pyridyl,

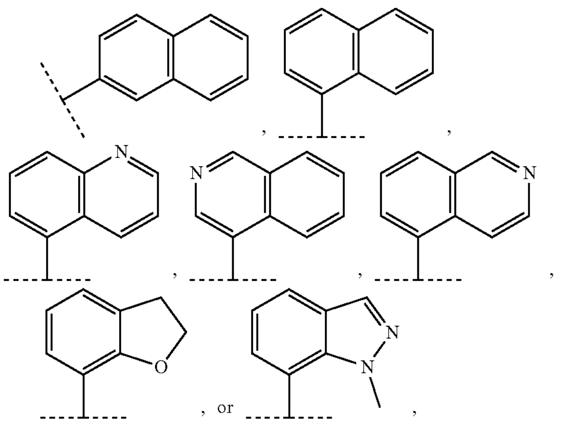

optionally substituted by one or more independent R1 substituents.

In some embodiments, $R^1$, for each occurrence, is chloro, fluoro, ethyl, isopropyl, methyl, methoxy, or CF3.

In some embodiments, Y is a direct bond to Ar1, —CH2-, —C(H)(OH)—, —C(CH3)(OH)—, —C(H)(—OCH3)-, —(CH2)2-, —O—, —NH—, —N(CH3)-, —C(H)(NH2)-, or —CF2-.

In some embodiments, R4 is H.

In some embodiments, Ar2 is phenyl or pyridyl, optionally substituted by one or more independent R2 substituents.

In some embodiments, R2, for each occurrence, is chloro, fluoro, ethyl, methyl, methoxy, CF3, or —O—CF3.

In some embodiments, R5 is methyl.

In some embodiments, R6 is H, ethyl, methyl, isopropyl or CF3.

In some embodiments, the compound is selected from:

N-(4-(4-amino-7-methyl-7H-pyrrolo[2,3-d]pyrimidin-5-yl)-3-methylphenyl)-2-hydroxy-2-phenylacetamide;

(R)—N-(4-(4-amino-7-methyl-7H-pyrrolo[2,3-d]pyrimidin-5-yl)-3-methylphenyl)-2-hydroxy-2-phenylacetamide;

(S)—N-(4-(4-amino-7-methyl-7H-pyrrolo[2,3-d]pyrimidin-5-yl)-3-methylphenyl)-2-hydroxy-2-phenylacetamide;

N-(4-(4-amino-7-methyl-7H-pyrrolo[2,3-d]pyrimidin-5-yl)-3-methylphenyl)-2-hydroxy-2-phenylpropanamide;

(R)—N-(4-(4-amino-7-methyl-7H-pyrrolo[2,3-d]pyrimidin-5-yl)-3-methylphenyl)-2-methoxy-2-phenylacetamide;

(S)—N-(4-(4-amino-7-methyl-7H-pyrrolo[2,3-d]pyrimidin-5-yl)-3-methyl phenyl)-2-methoxy-2-phenylacetamide;

2-amino-N-(4-(4-amino-7-methyl-7H-pyrrolo[2,3-d]pyrimidin-5-yl)-3-methylphenyl)-2-phenylacetamide;

(R)-2-amino-N-(4-(4-amino-7-methyl-7H-pyrrolo[2,3-d]pyrimidin-5-yl)-3-methylphenyl)-2-phenylacetamide;

(S)-2-amino-N-(4-(4-amino-7-methyl-7H-pyrrolo[2,3-d]pyrimidin-5-yl)-3-methylphenyl)-2-phenylacetamide;

N-(4-(4-amino-7-methyl-7H-pyrrolo[2,3-d]pyrimidin-5-yl)-3-methylphenyl)-2-(3-fluorophenyl)-2-hydroxyacetamide;

(R)—N-(4-(4-amino-7-methyl-7H-pyrrolo[2,3-d]pyrimidin-5-yl)-3-methylphenyl)-2-(3-fluorophenyl)-2-hydroxyacetamide;

(S)—N-(4-(4-amino-7-methyl-7H-pyrrolo[2,3-d]pyrimidin-5-yl)-3-methylphenyl)-2-(3-fluorophenyl)-2-hydroxyacetamide;

N-(4-(4-amino-7-methyl-7H-pyrrolo[2,3-d]pyrimidin-5-yl)-3-fluorophenyl)-2-(3-fluorophenyl)-2-hydroxyacetamide;

(R)—N-(4-(4-amino-7-methyl-7H-pyrrolo[2,3-d]pyrimidin-5-yl)-3-fluorophenyl)-2-(3-fluorophenyl)-2-hydroxyacetamide;

(S)—N-(4-(4-amino-7-methyl-7H-pyrrolo[2,3-d]pyrimidin-5-yl)-3-fluorophenyl)-2-(3-fluorophenyl)-2-hydroxyacetamide;

N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;

(R)—N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;

(S)—N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;

N-(4-(4-amino-7-methyl-7H-pyrrolo[2,3-d]pyrimidin-5-yl)-3-fluorophenyl)-2-(3-fluorophenyl)-2-hydroxyacetamide;

(R)—N-(4-(4-amino-7-methyl-7H-pyrrolo[2,3-d]pyrimidin-5-yl)-3-fluorophenyl)-2-(3-fluorophenyl)-2-hydroxyacetamide;

(S)—N-(4-(4-amino-7-methyl-7H-pyrrolo[2,3-d]pyrimidin-5-yl)-3-fluorophenyl)-2-(3-fluorophenyl)-2-hydroxyacetamide;

N-(4-(4-amino-7-methyl-7H-pyrrolo[2,3-d]pyrimidin-5-yl)-3-chlorophenyl)-2-(3-fluorophenyl)-2-hydroxyacetamide;

(R)—N-(4-(4-amino-7-methyl-7H-pyrrolo[2,3-d]pyrimidin-5-yl)-3-chlorophenyl)-2-(3-fluorophenyl)-2-hydroxyacetamide;

(S)—N-(4-(4-amino-7-methyl-7H-pyrrolo[2,3-d]pyrimidin-5-yl)-3-chlorophenyl)-2-(3-fluorophenyl)-2-hydroxyacetamide;

N-(4-(4-amino-7-methyl-7H-pyrrolo[2,3-d]pyrimidin-5-yl)-3-(trifluoromethyl)phenyl)-2-(3-fluorophenyl)-2-hydroxyacetamide;

(R)—N-(4-(4-amino-7-methyl-7H-pyrrolo[2,3-d]pyrimidin-5-yl)-3-(trifluoromethyl)phenyl)-2-(3-fluorophenyl)-2-hydroxyacetamide;

(S)—N-(4-(4-amino-7-methyl-7H-pyrrolo[2,3-d]pyrimidin-5-yl)-3-(trifluoromethyl)phenyl)-2-(3-fluorophenyl)-2-hydroxyacetamide;

N-(4-(4-amino-7-methyl-7H-pyrrolo[2,3-d]pyrimidin-5-yl)-3-ethylphenyl)-2-(3-fluorophenyl)-2-hydroxyacetamide;

(R)—N-(4-(4-amino-7-methyl-7H-pyrrolo[2,3-d]pyrimidin-5-yl)-3-ethylphenyl)-2-(3-fluorophenyl)-2-hydroxyacetamide;

(S)—N-(4-(4-amino-7-methyl-7H-pyrrolo[2,3-d]pyrimidin-5-yl)-3-ethylphenyl)-2-(3-fluorophenyl)-2-hydroxyacetamide;

N-(4-(4-amino-7-methyl-7H-pyrrolo[2,3-d]pyrimidin-5-yl)-3-(trifluoromethoxy)phenyl)-2-(3-fluorophenyl)-2-hydroxyacetamide;

(R)—N-(4-(4-amino-7-methyl-7H-pyrrolo[2,3-d]pyrimidin-5-yl)-3-(trifluoromethoxy)phenyl)-2-(3-fluorophenyl)-2-hydroxyacetamide;

(S)—N-(4-(4-amino-7-methyl-7H-pyrrolo[2,3-d]pyrimidin-5-yl)-3-(trifluoromethoxy)phenyl)-2-(3-fluorophenyl)-2-hydroxyacetamide;

N-(4-(4-amino-7-methyl-7H-pyrrolo[2,3-d]pyrimidin-5-yl)phenyl)-2-(3-fluorophenyl)-2-hydroxyacetamide;

(R)—N-(4-(4-amino-7-methyl-7H-pyrrolo[2,3-d]pyrimidin-5-yl)phenyl)-2-(3-fluorophenyl)-2-hydroxyacetamide;

(S)—N-(4-(4-amino-7-methyl-7H-pyrrolo[2,3-d]pyrimidin-5-yl)phenyl)-2-(3-fluorophenyl)-2-hydroxyacetamide;

N-(4-(4-amino-2,7-dimethyl-7H-pyrrolo[2,3-d]pyrimidin-5-yl)-3-methylphenyl)-2-(3-fluorophenyl)-2-hydroxyacetamide;

(R)—N-(4-(4-amino-2,7-dimethyl-7H-pyrrolo[2,3-d]pyrimidin-5-yl)-3-methylphenyl)-2-(3-fluorophenyl)-2-hydroxyacetamide;

(S)—N-(4-(4-amino-2,7-dimethyl-7H-pyrrolo[2,3-d]pyrimidin-5-yl)-3-methylphenyl)-2-(3-fluorophenyl)-2-hydroxyacetamide;

N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;

(R)—N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;

(S)—N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;

N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;

(R)—N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;
(S)—N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;
N-(4-(4-amino-7-methyl-7H-pyrrolo[2,3-d]pyrimidin-5-yl)-3-chlorophenyl)-2-(3-fluorophenyl)-2-hydroxyacetamide;
(R)—N-(4-(4-amino-7-methyl-7H-pyrrolo[2,3-d]pyrimidin-5-yl)-3-chlorophenyl)-2-(3-fluorophenyl)-2-hydroxyacetamide;
(S)—N-(4-(4-amino-7-methyl-7H-pyrrolo[2,3-d]pyrimidin-5-yl)-3-chlorophenyl)-2-(3-fluorophenyl)-2-hydroxyacetamide;
N-(4-(4-amino-7-methyl-7H-pyrrolo[2,3-d]pyrimidin-5-yl)-3-(trifluoromethyl)phenyl)-2-(3-fluorophenyl)-2-hydroxyacetamide;
(R)—N-(4-(4-amino-7-methyl-7H-pyrrolo[2,3-d]pyrimidin-5-yl)-3-(trifluoromethyl)phenyl)-2-(3-fluorophenyl)-2-hydroxyacetamide;
(S)—N-(4-(4-amino-7-methyl-7H-pyrrolo[2,3-d]pyrimidin-5-yl)-3-(trifluoromethyl)phenyl)-2-(3-fluorophenyl)-2-hydroxyacetamide;
N-(4-(4-amino-7-methyl-7H-pyrrolo[2,3-d]pyrimidin-5-yl)-3-ethylphenyl)-2-(3-fluorophenyl)-2-hydroxyacetamide;
(R)—N-(4-(4-amino-7-methyl-7H-pyrrolo[2,3-d]pyrimidin-5-yl)-3-ethylphenyl)-2-(3-fluorophenyl)-2-hydroxyacetamide;
(S)—N-(4-(4-amino-7-methyl-7H-pyrrolo[2,3-d]pyrimidin-5-yl)-3-ethylphenyl)-2-(3-fluorophenyl)-2-hydroxyacetamide;
N-(4-(4-amino-7-methyl-7H-pyrrolo[2,3-d]pyrimidin-5-yl)-3-(trifluoromethoxy)phenyl)-2-(3-fluorophenyl)-2-hydroxyacetamide;
(R)—N-(4-(4-amino-7-methyl-7H-pyrrolo[2,3-d]pyrimidin-5-yl)-3-(trifluoromethoxy)phenyl)-2-(3-fluorophenyl)-2-hydroxyacetamide;
(S)—N-(4-(4-amino-7-methyl-7H-pyrrolo[2,3-d]pyrimidin-5-yl)-3-(trifluoromethoxy)phenyl)-2-(3-fluorophenyl)-2-hydroxyacetamide;
N-(4-(4-amino-2,7-dimethyl-7H-pyrrolo[2,3-d]pyrimidin-5-yl)-3-(trifluoromethyl)phenyl)-2-(3-fluorophenyl)-2-hydroxyacetamide;
(R)—N-(4-(4-amino-2,7-dimethyl-7H-pyrrolo[2,3-d]pyrimidin-5-yl)-3-(trifluoromethyl)phenyl)-2-(3-fluorophenyl)-2-hydroxyacetamide;
(S)—N-(4-(4-amino-2,7-dimethyl-7H-pyrrolo[2,3-d]pyrimidin-5-yl)-3-(trifluoromethyl)phenyl)-2-(3-fluorophenyl)-2-hydroxyacetamide;
N-(4-(4-amino-2,7-dimethyl-7H-pyrrolo[2,3-d]pyrimidin-5-yl)-3-(trifluoromethoxy)phenyl)-2-(3-fluorophenyl)-2-hydroxyacetamide;
(R)—N-(4-(4-amino-2,7-dimethyl-7H-pyrrolo[2,3-d]pyrimidin-5-yl)-3-(trifluoromethoxy)phenyl)-2-(3-fluorophenyl)-2-hydroxyacetamide;
(S)—N-(4-(4-amino-2,7-dimethyl-7H-pyrrolo[2,3-d]pyrimidin-5-yl)-3-(trifluoromethoxy)phenyl)-2-(3-fluorophenyl)-2-hydroxyacetamide;
N-(4-(4-amino-2,7-dimethyl-7H-pyrrolo[2,3-d]pyrimidin-5-yl)phenyl)-2-(3-fluorophenyl)-2-hydroxyacetamide;
(R)—N-(4-(4-amino-2,7-dimethyl-7H-pyrrolo[2,3-d]pyrimidin-5-yl)phenyl)-2-(3-fluorophenyl)-2-hydroxyacetamide;
(S)—N-(4-(4-amino-2,7-dimethyl-7H-pyrrolo[2,3-d]pyrimidin-5-yl)phenyl)-2-(3-fluorophenyl)-2-hydroxyacetamide;
N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;
(R)—N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;
(S)—N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;
N-(4-(4-amino-2,7-dimethyl-7H-pyrrolo[2,3-d]pyrimidin-5-yl)-3-methylphenyl)-2-(6-methylpyridin-2-yl)acetamide;
N-(4-(4-amino-7-methyl-7H-pyrrolo[2,3-d]pyrimidin-5-yl)-3-methylphenyl)-2-(6-methylpyridin-2-yl)acetamide;
N-(4-(4-amino-7-methyl-7H-pyrrolo[2,3-d]pyrimidin-5-yl)-3-methylphenyl)-2-phenylacetamide;
N-(4-(4-amino-7-methyl-7H-pyrrolo[2,3-d]pyrimidin-5-yl)-3-methylphenyl)-2-(2-methoxyphenyl)acetamide;
N-(4-(4-amino-7-methyl-7H-pyrrolo[2,3-d]pyrimidin-5-yl)-3-methylphenyl)-2-(3-methoxyphenyl)acetamide;
N-(4-(4-amino-7-methyl-7H-pyrrolo[2,3-d]pyrimidin-5-yl)-3-methylphenyl)-2-(4-fluorophenyl)acetamide;
N-(4-(4-amino-7-methyl-7H-pyrrolo[2,3-d]pyrimidin-5-yl)-3-methylphenyl)-2-(4-methoxyphenyl)acetamide;
N-(4-(4-amino-7-methyl-7H-pyrrolo[2,3-d]pyrimidin-5-yl)-3-methylphenyl)-2-(o-tolyl)acetamide;
N-(4-(4-amino-7-methyl-7H-pyrrolo[2,3-d]pyrimidin-5-yl)-3-methylphenyl)-2-(n-tolyl)acetamide;
N-(4-(4-amino-7-methyl-7H-pyrrolo[2,3-d]pyrimidin-5-yl)-3-methylphenyl)-2-(p-tolyl)acetamide;
N-(4-(4-amino-7-methyl-7H-pyrrolo[2,3-d]pyrimidin-5-yl)-3-methylphenyl)-2-(2-ethylphenyl)acetamide;
N-(4-(4-amino-7-methyl-7H-pyrrolo[2,3-d]pyrimidin-5-yl)-3-methylphenyl)-2-(3-ethylphenyl)acetamide;
N-(4-(4-amino-7-methyl-7H-pyrrolo[2,3-d]pyrimidin-5-yl)-3-methylphenyl)-2-(4-ethylphenyl)acetamide;
N-(4-(4-amino-7-methyl-7H-pyrrolo[2,3-d]pyrimidin-5-yl)-3-methylphenyl)-2-(3-isopropylphenyl)acetamide;
N-(4-(4-amino-7-methyl-7H-pyrrolo[2,3-d]pyrimidin-5-yl)-3-methylphenyl)-2-(2-chlorophenyl)acetamide;
N-(4-(4-amino-7-methyl-7H-pyrrolo[2,3-d]pyrimidin-5-yl)-3-methylphenyl)-2-(3-chlorophenyl)acetamide;
N-(4-(4-amino-7-methyl-7H-pyrrolo[2,3-d]pyrimidin-5-yl)-3-methylphenyl)-2-(4-chlorophenyl)acetamide;
N-(4-(4-amino-7-methyl-7H-pyrrolo[2,3-d]pyrimidin-5-yl)-3-methylphenyl)-2-(naphthalen-2-yl)acetamide;
N-(4-(4-amino-7-methyl-7H-pyrrolo[2,3-d]pyrimidin-5-yl)-3-methylphenyl)-2-(naphthalen-1-yl)acetamide;
N-(4-(4-amino-7-methyl-7H-pyrrolo[2,3-d]pyrimidin-5-yl)-3-methylphenyl)-2-(quinolin-5-yl)acetamide;
N-(4-(4-amino-7-methyl-7H-pyrrolo[2,3-d]pyrimidin-5-yl)-3-methylphenyl)-2-(isoquinolin-4-yl)acetamide;
N-(4-(4-amino-7-methyl-7H-pyrrolo[2,3-d]pyrimidin-5-yl)-3-methylphenyl)-2-(isoquinolin-5-yl)acetamide;
N-(4-(4-amino-7-methyl-7H-pyrrolo[2,3-d]pyrimidin-5-yl)-3-methylphenyl)-2-(2-(trifluoromethyl)phenyl)acetamide;
N-(4-(4-amino-7-methyl-7H-pyrrolo[2,3-d]pyrimidin-5-yl)-3-methylphenyl)-2-(3-(trifluoromethyl)phenyl)acetamide;
N-(4-(4-amino-7-methyl-7H-pyrrolo[2,3-d]pyrimidin-5-yl)-3-methylphenyl)-2-(4-(trifluoromethyl)phenyl)acetamide;
N-(4-(4-amino-7-methyl-7H-pyrrolo[2,3-d]pyrimidin-5-yl)-3-methylphenyl)-2-(2-fluorophenyl)acetamide;
N-(4-(4-amino-7-methyl-7H-pyrrolo[2,3-d]pyrimidin-5-yl)-3-methylphenyl)-2-(3-fluorophenyl)acetamide;

N-(4-(4-amino-7-methyl-7H-pyrrolo[2,3-d]pyrimidin-5-yl)-3-methylphenyl)-2-(2,3-dimethylphenyl)acetamide;

N-(4-(4-amino-7-methyl-7H-pyrrolo[2,3-d]pyrimidin-5-yl)-3-methylphenyl)-2-cyclopropylacetamide;

N-(4-(4-amino-7-methyl-7H-pyrrolo[2,3-d]pyrimidin-5-yl)-3-methylphenyl)-2-cyclobutylacetamide;

N-(4-(4-amino-7-methyl-7H-pyrrolo[2,3-d]pyrimidin-5-yl)-3-methylphenyl)-2-cyclopentylacetamide;

N-(4-(4-amino-7-methyl-7H-pyrrolo[2,3-d]pyrimidin-5-yl)-3-methylphenyl)-2-cyclohexylacetamide;

N-(4-(4-amino-7-methyl-7H-pyrrolo[2,3-d]pyrimidin-5-yl)-3-methylphenyl)benzamide;

N-(4-(4-amino-7-methyl-7H-pyrrolo[2,3-d]pyrimidin-5-yl)-3-methylphenyl)-3-phenylpropanamide;

phenyl (4-(4-amino-7-methyl-7H-pyrrolo[2,3-d]pyrimidin-5-yl)-3-methylphenyl)carbamate;

1-(4-(4-amino-7-methyl-7H-pyrrolo[2,3-d]pyrimidin-5-yl)-3-methylphenyl)-3-phenylurea;

3-(4-(4-amino-7-methyl-7H-pyrrolo[2,3-d]pyrimidin-5-yl)-3-methylphenyl)-1-methyl-1-phenylurea;

or a pharmaceutically acceptable salt thereof.

Embodiments of the present invention further provide a pharmaceutical composition, comprising a compound or a pharmaceutically acceptable salt thereof including one or more pharmaceutically acceptable carriers, diluents, or excipients.

Embodiments of the present invention further provide a method of treating cancer in a patient comprising administering to a patient in need thereof an effective amount of any of the above compounds, or a pharmaceutically acceptable salt thereof.

Embodiments of the present invention further provide a method of treating cancer in a patient comprising administering to a patient in need thereof an effective amount of any of the above compounds in combination with an anti-cancer agent, or pharmaceutically acceptable salts thereof.

Embodiments of the present invention further provide a compound or pharmaceutically acceptable salt thereof for use in therapy.

Embodiments of the present invention further provide a compound or pharmaceutically acceptable salt thereof according to any of the compounds for use in the treatment of cancer.

In some embodiments, the cancer is particularly pancreatic cancer, melanoma, or breast cancer, including BrCa positive breast cancer.

Embodiments of the present invention further provide a method of treating a disease in a patient in need of such treatment, said method comprising administering a PERK kinase modulating compound according to any of the above compounds, or a pharmaceutically acceptable salt thereof, wherein the disease is cancer.

The present invention provides a method of treating cancer in a patient in need of such treatment, comprising administering to the patient an effective amount of a compound of formula I, Ia, Ib, Ic Id, or Je, or a pharmaceutically acceptable salt thereof. The present invention also provides a method of inhibiting PERK activity resulting in antitumor activity in a patient in need of such treatment, comprising administering to the patient an effective amount of a compound of formula I, Ia, Ib, Ic, Id, or Je, or a pharmaceutically acceptable salt thereof.

In some embodiments of any of the above methods or uses, the subject is a human. In some embodiments of any of the above methods or uses, the compound and/or anti-cancer agent is orally administered to the subject. In some embodiments of any of the above methods or uses, the compound and/or anti-cancer agent is administered to the subject.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include multiple myeloma, blood cancers, lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

As used herein, a "symptom" associated with cancer includes any clinical or laboratory manifestation associated with the cancer and is not limited to what the subject can feel or observe.

As used herein, "treating", e.g. of a cancer, encompasses inducing prevention, inhibition, regression, or stasis of the disease or a symptom or condition associated with the cancer.

The contents of International Application Publication No. WO/2018/194885, published Oct. 25, 2018, are hereby incorporated by reference.

If a chiral center or another form of an isomeric center is present in a compound of the present invention, all forms of such isomer or isomers, including racemates, enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention.

The compounds of the present invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is 2H, 3H, 13C, 14C, 15N, and/or 180. Accordingly, in the compounds provided herein hydrogen can be enriched in the deuterium isotope. It is to be understood that the invention encompasses all such isotopic forms.

In an alternative embodiment, compounds described herein may also comprise one or more isotopic substitutions. For example, hydrogen may be 2H (D or deuterium) or 3H (T or tritium); carbon may be, for example, 13C or 14C; oxygen may be, for example, 180; nitrogen may be, for example, 15N, and the like. In other embodiments, a particular isotope (e.g., 3H, 13C, 14C, 180, or 15N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as 12C, 13C, or 14C. Furthermore, any compounds containing 13C or 14C may specifically have the structure of any of the compounds disclosed herein.

It will also be noted that any notation of a hydrogen in structures throughout this application, when used without further notation, are intended to represent all isotopes of hydrogen, such as 1H, 2H, or 3H. Furthermore, any compounds containing 2H or 3H may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure result.

In choosing the compounds used in the method of the present invention, one of ordinary skill in the art will recognize that the various substituents, i.e. $R^1$, $R^2$, etc. are to be chosen in conformity with well-known principles of chemical structure connectivity.

As used herein, "C0-4alkyl" for example is used to mean an alkyl having 0-4 carbons that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

As used herein, "alkyl" is intended to include both branched and straight-chain saturated aliphatic hydrocarbon groups having the specified number of carbon atoms. Thus, C1-Cn as in "C1-Cn alkyl" is defined to include groups having 1, 2 . . . , n−1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on.

"Alkoxy" or "Alkoxyl" represents an alkyl group as described above attached through an oxygen bridge. Thus, an alkoxy group is represented by C0-nalkyl-O—C0-malkyl in which oxygen is a bridge between 0, 1, 2 . . . , n−1, m−1, n or m carbons in a linear or branched arrangement. When n is zero, "—O—C0-malkyl" is attached directly to the preceding moiety. When m is zero, the alkoxy group is "C0-nalkyl-OH." Examples of alkoxy groups include methoxy, ethoxy, isopropoxy, tert-butoxy and so on.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, C2-Cn alkenyl is defined to include groups having 1, 2 . . . , n−1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a C6 alkenyl, respectively.

Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be C2-C12 alkenyl, C3-C12 alkenyl, C4-C12 alkenyl and so on.

The term "alkynyl" refers to a hydrocarbon radical straight or branched, containing at least 1 carbon to carbon triple bond, and up to the maximum possible number of non-aromatic carbon-carbon triple bonds may be present. Thus, C2-Cn alkynyl is defined to include groups having 1, 2 . . . , n−1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a C2-Cn alkynyl. An embodiment can be C2-C12 alkynyl, C3-C12 alkynyl, C4-C12 alkynyl and so on.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As used herein, "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 12 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 12 atoms that is fused to a polyatomic carbon ring of up to 12 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 12 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "arylalkyl" refers to alkyl groups as described above wherein one or more bonds to hydrogen contained therein are replaced by a bond to an aryl group as described above.

It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 12 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "alkylheteroaryl" refers to alkyl groups as described above wherein one or more bonds to hydrogen contained therein are replaced by a bond to an heteroaryl group as described above. It is understood that an "alkylheteroaryl" group is connected to a core molecule through a bond from the alkyl group and that the heteroaryl group acts as a substituent on the alkyl group. Examples of alkylheteroaryl moieties include, but are not limited to, —CH2-(C5H4N), —CH2-CH2-(C5H4N) and the like.

The term "heterocycle" or "heterocyclyl" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise. In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" or "halo" refers to F, Cl, Br, and I.

As used herein, the term "carbonyl" refers to a carbon atom double bonded to oxygen.

A carbonyl group is denoted as RxC(O)Ry where Rx and Ry are bonded to the carbonyl carbon atom.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure result.

In choosing the compounds of the present invention, one of ordinary skill in the art will recognize that the various substituents, i.e. R1, R2, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only methods by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5th Edition (1996), March's Advanced Organic Chemistry: Reactions, Mechanisms, and Structure, Michael B. Smith, Jerry March, (Wiley-Interscience) 5th Edition (2007), and references therein, which are incorporated by reference herein. However, these may not be the only methods by which to synthesize or obtain the desired compounds.

Another aspect of the invention comprises a compound used in the method of the present invention as a pharmaceutical composition.

In some embodiments, a pharmaceutical composition comprises the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30th edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium.

The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously.

These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992);

Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

For instance, for oral administration in the dosage unit form of a tablet or capsule, the active drug component can be combined with an oral, non-toxic, pharmaceutically acceptable, inert carrier.

The compounds used in the method of the present invention may also be administered in the form of liposome delivery systems, such as small unilamellar vesicles, large unilamellar vesicles, and multilamellar vesicles.

The compounds used in the method of the present invention may also be coupled to soluble polymers as targetable drug carriers or as a prodrug. Furthermore, the compounds may be coupled to a class of biodegradable polymers useful in achieving controlled release of a drug.

Gelatin capsules may contain the active ingredient compounds and powdered carriers/diluents. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components can be combined with any oral, non-toxic, pharmaceutically acceptable inert carrier. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. Solutions for parenteral administration preferably contain a water-soluble salt of the active ingredient, suitable stabilizing agents, and if necessary, buffer substances. In addition, parenteral solutions can contain preservatives. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine.

The compounds and compositions of the invention can be coated onto stents for temporary or permanent implantation into the cardiovascular system of a subject.

Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

The following materials and methods are used to test the compounds of the present invention.

PERK In Vitro Activity Assay (Isolated):

In vitro Inhibition of PERK Enzyme Activity (isolated) Recombinant human EIF2AK2 (PKR) catalytic domain (amino acids 252-551), EIF2AK3 (PERK) catalytic domain (amino acids 536-1116), GFP-eIF2a substrate, and Terbium-labelled phospho-eIF2a antibody is obtained (Invitrogen, Carlsbad, CA).

Express and purify HIS-SUMO-GCN2 catalytic domain (amino acids 584-1019) from *E. coli*. Perform TR-FRET kinase assays in the absence or presence of inhibitors in a reaction buffer consisting of 50 mM HEPES, pH 7.5, 10 mM MgCb, 1.0 mM EGTA, and 0.01% Brij-35, and 100-200 nM GFP-eIF2a substrate. PKR assays contain 14 ng/mL enzyme and 2.5 μM ATP (Km, −2.5 μM), PERK assays contain 62.5 ng/mL enzyme and 1.5 μM ATP (Km. app −1.5 uM), and GCN2 assays contain 3 nM enzyme and 90 μM ATP (Kin, −200 uM). Add test compound, initiate the reaction by addition of enzyme, and incubate at room temperature for 45 minutes. Stop the reaction by addition of EDTA to a final concentration of 10 mM, add Terbium-labelled phospho-eIF2a antibody at a final concentration of 2 nM, and incubate for 90 minutes. Monitor the resulting fluorescence in an EnVison® Multilabel reader (PerkinElmer, Waltham, MA). Determine TR-FRET ratios and the resulting IC50 values using a 4-parameter nonlinear logistic equation as shown: Y=(A+((B−A)/(1+((C/x)AD)))) where, Y=% specific inhibition, A=Bottom of the curve, B=Top of the curve, C=absolute IC50 (concentration causing 50% inhibition), and D=hill slope.

The compounds of Examples 1 to 171 were tested essentially as described above and exhibited IC50 values shown in Table 1. These data demonstrate that the compounds of Examples 1 to 171 inhibit isolated PERK enzyme activity in vitro.

PERK Cellular Assay

Stable cell lines were created in HEK293 cells using lentiviral particles harboring an expression vector for GFP-eIF2α. Cells were selected using puromycin and enriched using fluorescence activated cell sorting against GFP. HEK293-EGFP-eIF2a cells were plated at 5000 cells/well in 384-well assay plates and incubated overnight at 37° C., 5% CO2. Inhibitor compounds were added to the wells by Echo acoustic dispensing and incubated for 30 minutes at 37° C., 5% CO2 prior to induction of ER stress by addition of tunicamycin to 1 mM for 2 hours. Cells were lysed and TR-FRET was measured in an EnVision plate reader (PerkinElmer). FRET ratio data was normalized to signal from lysates treated with DMSO vehicle control and plotted as percent inhibition against 10-point; 3-fold dilution series of inhibitors. IC50 values were calculated using 4-parameter logistical fitting in XLFit.

The compounds of Examples 1 to 171 were tested essentially as described above and exhibited cellular IC50 values shown in Table 1. These data demonstrate that the compounds of Examples 1 to 171 inhibit EIF2a in vitro.

The results of exemplary compounds of formula (I) are shown in Table 1. Key: A is 0.001 to 0.025 μM; B is 0.026 to 0.050 μM; C is 0.051 to 0.100 μM; D is 0.101 to 0.250 μM; E is 0.251 to 0.500 μM; F is 0.501 to 1.00 μM; G is 1.001 μM to 2.00 μM; H is 2.001 μM to 3.00 μM; I is 3.001 to 4.00 μM; J is 4.001 to 5.00 μM; K is >5.00 μM; and N/A is "not available".

TABLE 1

Biochemical and cellular $IC_{50}$ data of Compounds of Formula I:

| Example | Biochemical $IC_{50}$ (μM) | Cellular eIF2α $IC_{50}$ (μM) |
|---|---|---|
| 1 | A | B |
| 2 | C | E |
| 3 | A | B |
| 4 | A | A |
| 5 | A | B |
| 6 | A | A |
| 7 | C | D |
| 8 | A | D |
| 9 | A | A |
| 10 | A | C |
| 11 | A | A |
| 12 | A | A |
| 13 | C | G |
| 14 | A | A |
| 15 | B | C |
| 16 | A | D |
| 17 | A | A |
| 18 | A | D |
| 19 | A | D |
| 20 | C | G |
| 21 | A | F |
| 22 | D | K |
| 23 | A | F |
| 24 | B | G |
| 25 | D | K |
| 26 | B | F |
| 27 | D | E |
| 28 | E | F |
| 29 | A | A |
| 30 | A | D |
| 31 | A | B |
| 32 | D | E |
| 33 | A | C |
| 34 | D | F |
| 35 | A | A |
| 36 | A | B |
| 37 | A | A |
| 38 | C | F |
| 39 | A | B |
| 40 | B | D |
| 41 | A | A |
| 42 | A | C |
| 43 | A | A |
| 44 | D | G |
| 45 | A | D |
| 46 | E | H |
| 47 | A | A |
| 48 | A | C |
| 49 | A | B |
| 50 | A | A |
| 51 | D | F |
| 52 | A | A |
| 53 | B | E |
| 54 | A | B |
| 55 | D | E |
| 56 | A | A |
| 57 | B | D |
| 58 | A | C |
| 59 | C | E |
| 60 | A | D |
| 61 | D | F |
| 62 | C | H |
| 63 | D | H |
| 64 | E | H |
| 65 | E | I |
| 66 | N/A | N/A |
| 67 | D | G |
| 68 | A | B |
| 69 | D | H |
| 70 | G | K |
| 71 | N/A | H |
| 72 | N/A | B |
| 73 | B | F |
| 74 | A | A |
| 75 | C | G |

TABLE 1-continued

| Biochemical and cellular $IC_{50}$ data of Compounds of Formula I: | | |
|---|---|---|
| Example | Biochemical $IC_{50}$ (μM) | Cellular eIF2α $IC_{50}$ (μM) |
| 76 | A | A |
| 77 | B | F |
| 78 | A | A |
| 79 | C | F |
| 80 | A | B |
| 81 | C | D |
| 82 | A | A |
| 83 | A | A |
| 84 | C | D |
| 85 | A | A |
| 86 | A | C |
| 87 | A | C |
| 88 | B | E |
| 89 | E | H |
| 90 | A | B |
| 91 | D | F |
| 92 | A | C |
| 93 | F | H |
| 94 | A | C |
| 95 | C | E |
| 96 | A | A |
| 97 | A | A |
| 98 | C | E |
| 99 | A | A |
| 100 | B | D |
| 101 | A | A |
| 102 | D | D |
| 103 | D | H |
| 104 | B | D |
| 105 | K | K |
| 106 | D | G |
| 107 | A | A |
| 108 | D | D |
| 109 | E | G |
| 110 | A | A |
| 111 | A | A |
| 112 | D | F |
| 113 | A | A |
| 114 | E | G |
| 115 | A | A |
| 116 | E | E |
| 117 | A | A |
| 118 | B | E |
| 119 | A | A |
| 120 | C | E |
| 121 | A | B |
| 122 | D | G |
| 123 | A | B |
| 124 | A | A |
| 125 | A | C |
| 126 | A | C |
| 127 | A | D |
| 128 | F | K |
| 129 | A | C |
| 130 | D | G |
| 131 | B | E |
| 132 | A | C |
| 133 | E | J |
| 134 | A | D |
| 135 | B | E |
| 136 | A | A |
| 137 | A | B |
| 138 | A | D |
| 139 | B | E |
| 140 | A | B |
| 141 | C | E |
| 142 | A | B |
| 143 | A | B |
| 144 | A | D |
| 145 | A | B |
| 146 | A | A |
| 147 | A | C |
| 148 | A | D |
| 149 | A | B |
| 150 | A | B |

TABLE 1-continued

| Biochemical and cellular $IC_{50}$ data of Compounds of Formula I: | | |
|---|---|---|
| Example | Biochemical $IC_{50}$ (μM) | Cellular eIF2α $IC_{50}$ (μM) |
| 151 | A | D |
| 152 | A | C |
| 153 | A | B |
| 154 | C | F |
| 155 | B | D |
| 156 | C | E |
| 157 | A | C |
| 158 | A | N/A |
| 159 | C | F |
| 160 | A | N/A |
| 161 | B | N/A |
| 162 | A | C |
| 163 | K | K |
| 164 | C | H |
| 165 | D | F |
| 166 | A | D |
| 167 | D | I |
| 168 | D | G |
| 169 | I | K |
| 170 | A | D |
| 171 | D | G |

HPLC Conditions:

Method A

Column: Polaris C18-A 2.6 μm C18 (100×3.0 mm)

Mobile Phase A: Water containing 0.05% v/v Trifluoroacetic Acid

Mobile Phase B: Acetonitrile containing 0.05% v/v Trifluoroacetic Acid

Detection: 230 nm

Method A Gradient

| Time (min) | Flow (mL/min) | % A | % B |
|---|---|---|---|
| 0.0 | 0.8 | 95.0 | 5.0 |
| 3.0 | 0.8 | 95.0 | 5.0 |
| 6.0 | 0.8 | 10.0 | 90.0 |
| 12.0 | 0.8 | 10.0 | 90.0 |

Method B

Column: Eclipse plus C18 3.5 μm C18 (100×4.6 mm)

Mobile Phase A: Water containing 0.05% v/v Trifluoroacetic Acid

Mobile Phase B: Acetonitrile containing 0.05% v/v Trifluoroacetic Acid

Detection: 254 nm

Method B Gradient

| Time (min) | Flow (mL/min) | % A | % B |
|---|---|---|---|
| 0.0 | 0.8 | 95.0 | 5.0 |
| 3.0 | 0.8 | 95.0 | 5.0 |
| 6.0 | 0.8 | 10.0 | 90.0 |
| 12.0 | 0.8 | 10.0 | 90.0 |

Method C

Column: Eclipse plus C18 3.5 μm C18 (100×4.6 mm)

Mobile Phase A: Water containing 0.05% v/v Trifluoroacetic Acid

Mobile Phase B: Acetonitrile containing 0.05% v/v Trifluoroacetic Acid

Detection: 270 nm
Method C Gradient

| Time (min) | Flow (mL/min) | % A | % B |
|---|---|---|---|
| 0.0 | 0.8 | 95.0 | 5.0 |
| 3.0 | 0.8 | 95.0 | 5.0 |
| 6.0 | 0.8 | 10.0 | 90.0 |
| 12.0 | 0.8 | 10.0 | 90.0 |

Analytical SFC Conditions:
Method A
Column: Chiralcel OX—H
Mobile Phase: 30% Methanol in $CO_2$
Temperature: 40° C.
Run Time: 10.0 min
Detection: 210 nm
Method B
Column: Chiralpak IC
Mobile Phase: 30% Methanol in $CO_2$
Temperature: 40° C.
Run Time: 8.0 min
Detection: 215 nm
Method C
Column: Chiralcel OD-H
Mobile Phase: 25% Methanol in $CO_2$
Temperature: 40° C.
Run Time: 10.0 min
Detection: 215 nm
Method D
Column: Chiralpak IA
Mobile Phase: 40% Methanol in $CO_2$
Temperature: 40° C.
Run Time: 8.0 min
Detection: 210 nm Abbreviations NMR: nuclear magnetic resonance;
mHz: megahertz;
DMSO-$d_6$: dimethyl sulfoxide-$d_6$;
$CDCl_3$: deuterated chloroform;
δ: chemical shift;
MS: mass spectrometry;
HPLC: high performance liquid chromatography;
SFC: Supercritical fluid chromatography
m/z: mass-to-charge ratio;
[M+H]: molecular ion peak in mass spectrum;
ESI: electrospray ionization;
$ESI^+$: electrospray ionization positive mode;
ESI: electrospray ionization negative mode;
rt or RT: room temperature;
min: minute(s);
h: hour(s)
mg: milligram;
g: gram;
kg: kilogram;
mL: milliliter;
L: liter;
mmol: millimole;
μM: micromole;
MTBE: methyl tert-butyl ether;
THF tetrahydrofuran;
HATU: (1-[bis(dimethylamino)methylene]-1H-1,2,3-triazolo[4,5-b]pyridinium 3-oxid hexafluorophosphate;
DIPEA or DIEA: N,N-diisopropylethylamine;
HOBt: hydroxybenzotriazole;
$Pd(dppf)Cl_2$: [1,1'-bis(diphenylphosphino)ferrocene]dichloropalladium(II);
EDC: 1-ethyl-3-(3-dimethylaminopropyl)carbodiimide.

Scheme A

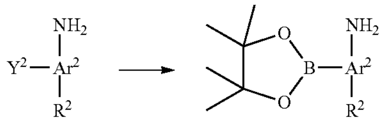

A-1

A-2

Compounds of Formula A-2 where $Ar^2$=phenyl and $R^2$=3-methyl can be synthesized as described below for compound A-2.1:

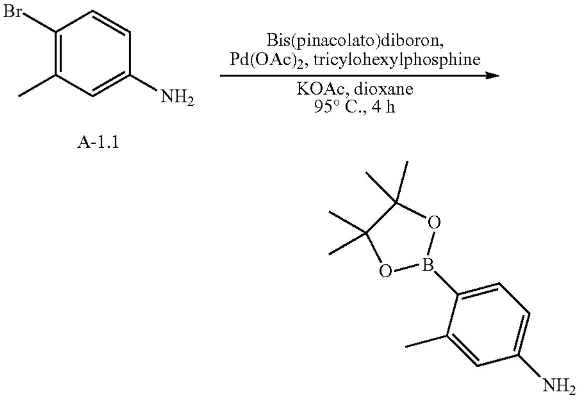

A-1.1

A-2.1

Synthesis of 3-methyl-4-(4,4,5,5-tetramethyl-1,3,2-dioxaborolan-2-yl)aniline (A-2.1)

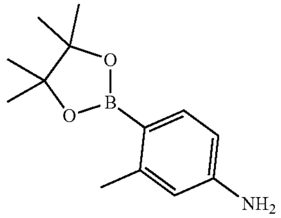 [SMILES: Cc1cc(N)ccc1B1OC(C)(C)C(C)(C)O1]

To a stirred solution of tricyclohexylphosphine (7.18 g, 25.7 mmol) in 1,4-dioxane (1.2 L) under argon atmosphere were added bis(pinacolato)diboron (89.62 g, 352.9 mmol) and potassium acetate (62.98 g, 641.7 mmol), followed by 4-bromo-3-methylaniline (A-1.1, 60.00 g, 320.8 mmol). The reaction mixture was purged with argon for 10 min. Palladium(II) acetate (5.77 g, 25.7 mmol) was added, and the mixture was purged with argon for 10 min. The reaction mixture was heated at 95° C. with stirring for 16 h. After this time, the reaction mixture was allowed to cool to room temperature, passed through a bed of diatomaceous earth, and washed with methyl tert-butyl ether (4×250 mL). The filtrate was washed with water (2×500 mL) and brine (2×250 mL). The organic layer was separated, dried over anhydrous sodium sulfate and concentrated under reduced pressure. The crude product was purified by column chromatography (silica gel, 10% ethyl acetate/hexanes) to afford 3-methyl-4-(4,4,5,5-tetramethyl-1,3,2-dioxaborolan-2-yl)aniline (A-2.1, 44.80 g, yield: 60%) as a pale brown solid: ESI (m/z) 234 $[C_{13}H_{20}BNO_2+H]^+$.

The compounds of formula A-2 (Table A) can be synthesized according to the procedures described for compound A-2.1:

TABLE A

| Compounds A-2: | | | |
|---|---|---|---|
| Compound | | Structure | MS |
| A-2.1 | 3-methyl-4-(4,4,5,5-tetramethyl-1,3,2-dioxaborolan-2-yl)aniline | 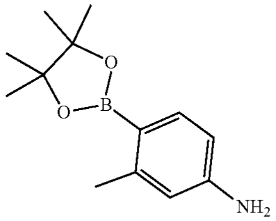 [SMILES: Cc1cc(N)ccc1B1OC(C)(C)C(C)(C)O1] | ESI (m/z) 234 $[C_{13}H_{20}BNO_2 + H]^+$ |
| A-2.2 | 4-(4,4,5,5-tetramethyl-1,3,2-dioxaborolan-2-yl)aniline | 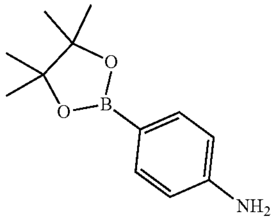 [SMILES: CC1(C)OB(c2ccc(N)cc2)OC1(C)C] | ESI (m/z) 220 $[C_{12}H_{18}BNO_2 + H]^+$ |
| A-2.3 | 3-fluoro-4-(4,4,5,5-tetramethyl-1,3,2-dioxaborolan-2-yl)aniline | 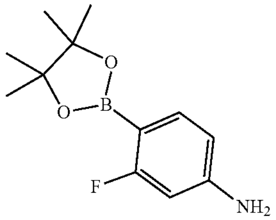 [SMILES: CC1(C)OB(c2ccc(N)cc2F)OC1(C)C] | ESI (m/z) 238 $[C_{12}H_{17}BFNO_2 + H]^+$ |
| A-2.4 | 3-chloro-4-(4,4,5,5-tetramethyl-1,3,2-dioxaborolan-2-yl)aniline | 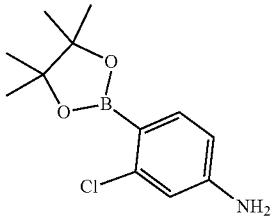 [SMILES: CC1(C)OB(c2ccc(N)cc2Cl)OC1(C)C] | ESI (m/z) 253, 255 $[C_{12}H_{17}BClNO_2 + H]^+$ |
| A-2.5 | 4-(4,4,5,5-tetramethyl-1,3,2-dioxaborolan-2-yl)-3-(trifluoromethoxy) aniline | 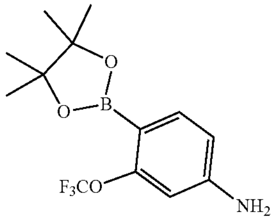 [SMILES: CC1(C)OB(c2ccc(N)cc2OC(F)(F)F)OC1(C)C] | ESI (m/z) 304 $[C_{13}H_{17}BF_3NO_3 + H]^+$ |
| A-2.6 | 4-(4,4,5,5-tetramethyl-1,3,2-dioxaborolan-2-yl)-3-(trifluoromethyl) aniline | 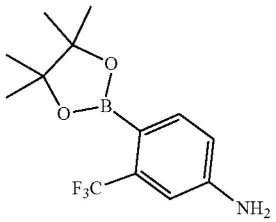 [SMILES: CC1(C)OB(c2ccc(N)cc2C(F)(F)F)OC1(C)C] | ESI (m/z) 288 $[C_{13}H_{17}BF_3NO_2 + H]^+$ |

TABLE A-continued

| Compounds A-2: | | | |
|---|---|---|---|
| Compound | | Structure | MS |
| A-2.7 | 3-ethyl-4-(4,4,5,5-tetramethyl-1,3,2-dioxaborolan-2-yl)aniline | 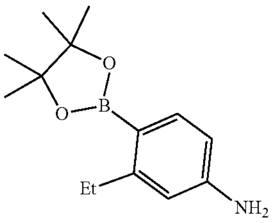 [SMILES: CCc1cc(N)ccc1B1OC(C)(C)C(C)(C)O1] | ESI (m/z) 248 $[C_{14}H_{22}BNO_2 + H]^+$ |
| A-2.8 | 3-methoxy-4-(4,4,5,5-tetramethyl-1,3,2-dioxaborolan-2-yl)aniline | 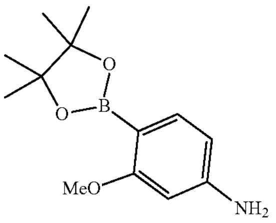 [SMILES: COc1cc(N)ccc1B1OC(C)(C)C(C)(C)O1] | ESI (m/z) 250 $[C_{13}H_{20}BNO_3 + H]^+$ |
| A-2.9 | 2-fluoro-3-methyl-4-(4,4,5,5-tetramethyl-1,3,2-dioxaborolan-2-yl)aniline | 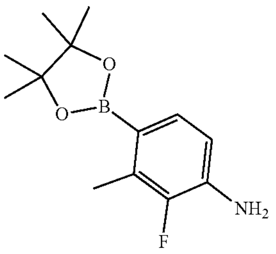 [SMILES: Cc1c(B2OC(C)(C)C(C)(C)O2)ccc(N)c1F] | ESI (m/z) 252 $[C_{13}H_{19}BFNO_2 + H]^+$ |

Scheme B

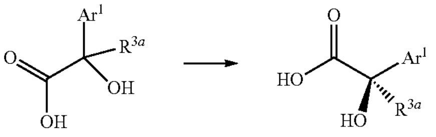

B-1 B-2

Compounds of Formula B-2 where $Ar^1$=3,5-difluorophenyl and $R^{3a}$=H can be synthesized as described below for compound B-2.1:

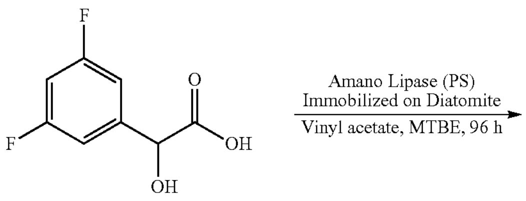

B-1.1

-continued

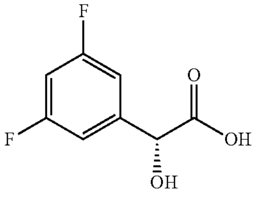

B-2.1

Synthesis of (R)-2-(3,5-difluorophenyl)-2-hydroxyacetic acid (B-2.1)

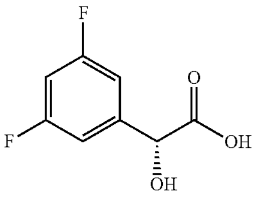

To a stirred solution of Amano lipase (PS) supported on Diatomite (5.0 g; purchased from Sigma-Aldrich) in methyl tert-butyl ether (MTBE, 50 mL) were added 2-(3,5-difluorophenyl)-2-hydroxyacetic acid (B-1.1, 2.50 g, 13.3 mmol) and vinyl acetate (5.37 g, 62.5 mmol). The reaction mixture was allowed to stir for 96 h. After this time, the supported enzyme was filtered off and washed with methyl tert-butyl ether (12 mL). The filtrate was concentrated under reduced pressure. The residue was stirred in methylene chloride (2.5 mL) for 10 min. The resulting white solid was isolated by filtration, washed with methylene chloride (2 mL), and dried under vacuum to obtain pure (R)-2-(3,5-difluorophenyl)-2-hydroxyacetic acid (B-2.1, 850 mg, yield: 34%): $^1H$ NMR (400 MHz, DMSO-$d_6$) δ 7.18-7.10 (m, 3H), 5.10 (s, 1H); ESI (m/z) 187 $[C_8H_6F_2O_3-H]^-$; SFC (chiral) purity >99%.

The compounds of formula B-2 (Table B) can be synthesized according to the procedures described for compound B-2.1

TABLE B

| Compounds B-2: | | | |
|---|---|---|---|
| Compound | Name | Structure | MS |
| B-2.1 | (R)-2-(3,5-difluorophenyl)-2-hydroxyacetic acid | 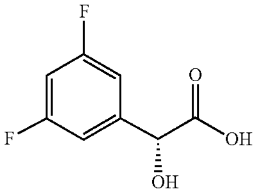 [SMILES: O=C(O)[C@H](O)c1cc(F)cc(F)c1] | ESI (m/z): 187 $[C_8H_6F_2O_3 - H]^-$ |
| B-2.2 | (R)-2-(3-fluorophenyl)-2-hydroxyacetic acid | 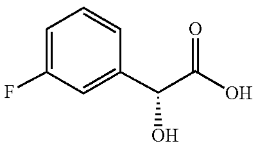 [SMILES: O=C(O)[C@H](O)c1cccc(F)c1] | ESI (m/z): 169 $[C_8H_7FO_3 - H]^-$ |

Scheme B1

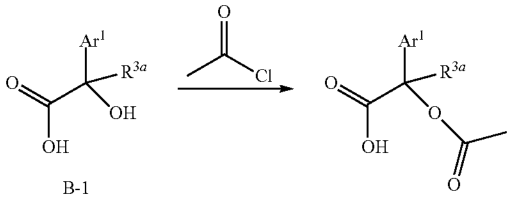

B-1

B-2

Compounds of Formula B-2 where $Ar^1$=3-chlorophenyl and $R^{3a}$=H can be synthesized as described below for compound B-2.1

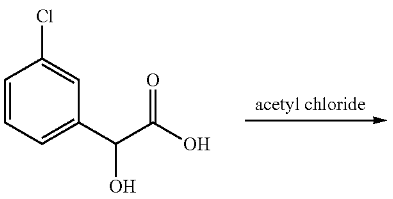

B-1.2

-continued

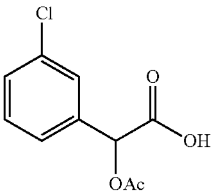

B-2.1

Synthesis of 2-acetoxy-2-(3-chlorophenyl)acetic acid (B-2.1)

To a stirred solution of acetyl chloride (2.0 mL) at 0° C. was added 2-(3-chlorophenyl)-2-hydroxyacetic acid (B-1.2, 2.00 g, 10.6 mmol) portion wise over a period of 10 min. at same temperature. The reaction mixture was allowed to warm to room temperature and stirred for 1 h. After this time, the reaction mixture was concentrated under reduced pressure to get crude material followed by co-distilled with hexanes to afford 2-acetoxy-2-(3-chlorophenyl)acetic acid (B-2.1, 2.10 g, yield: 86%) as a white solid; $^1H$ NMR (400 MHz, DMSO-$d_6$): δ 7.54-7.44 (m, 4H), 5.87 (s, 1H), 2.14 (s, 3H); ESI (m/z) 228.6 $[C_{10}H_9ClO_4+H]^+$.

The compounds of formula B-2 (Table B1) can be synthesized according to the procedures described for compound B-2.1:

TABLE B1

| Compounds C-1: | | | |
|---|---|---|---|
| Compound | Name | Structure | MS |
| B-2.1 | 2-acetoxy-2-(3-chlorophenyl)acetic acid | 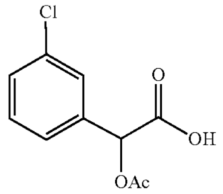 [SMILES: CC(=O)OC(C(=O)O)c1cccc(Cl)c1] | ESI (m/z) 228.6 $[C_{10}H_9ClO_4 + H]^+$ |
| B-2.2 | 2-acetoxy-2-(2-fluorophenyl)acetic acid | 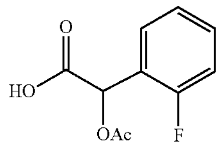 [SMILES: CC(=O)OC(C(=O)O)c1ccccc1F] | ESI (m/z) 213 $[C_{10}H_9FO_4 + H]^+$ |
| B-2.3 | 2-acetoxy-2-(3-fluorophenyl)acetic acid | 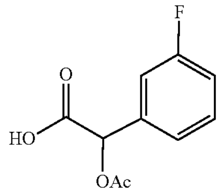 [SMILES: CC(=O)OC(C(=O)O)c1cccc(F)c1] | ESI (m/z) 213 $[C_{10}H_9FO_4 + H]^+$ |
| B-2.4 | 2-acetoxy-2-(2-chlorophenyl)acetic acid | 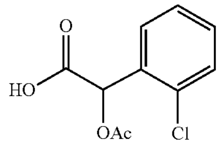 [SMILES: CC(=O)OC(C(=O)O)c1ccccc1Cl] | ESI (m/z) 229 $[C_{10}H_9ClO_4 + H]^+$ |
| B-2.5 | 2-acetoxy-2-(o-tolyl)acetic acid | 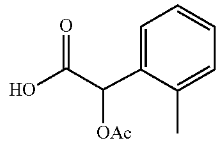 | ESI (m/z) 209 $[C_{11}H_{12}O_4 + H]^+$ |
| B-2.6 | 2-acetoxy-2-(m-tolyl)acetic acid | 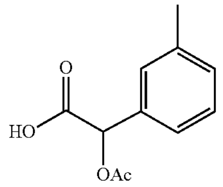 | ESI (m/z) 208.2 $[C_{11}H_{12}O_4 + H]^+$ |
| B-2.7 | 2-acetoxy-2-(2-(trifluoromethyl)phenyl) acetic acid | 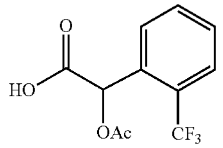 [SMILES: CC(=O)OC(C(=O)O)c1ccccc1C(F)(F)F] | ESI (m/z) 262.2 $[C_{11}H_9F_3O_4 + H]^+$ |
| B-2.8 | 2-acetoxy-2-(3-fluoro-5-methylphenyl)acetic acid | 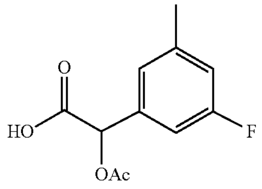 [SMILES: CC(=O)OC(C(=O)O)c1cc(C)cc(F)c1] | ESI (m/z) 226.2 $[C_{11}H_{11}FO_4 + H]^+$ |

Scheme B2

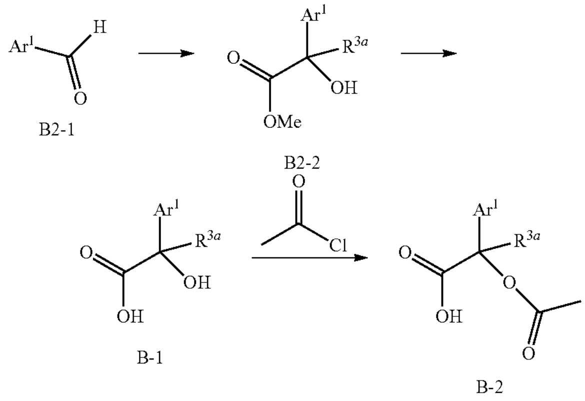

B2-1 B2-2 B-1 B-2

Compounds of Formula B-2' where $Ar^1$=3-trifluoromethylphenyl and $R^{3a}$=H can be synthesized as described below for compound B-2.9

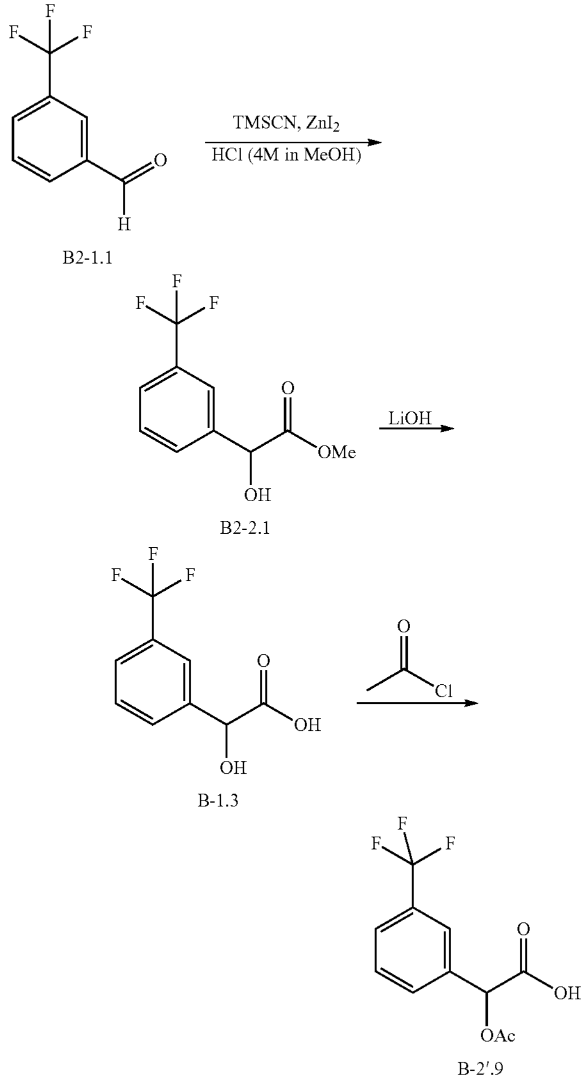

B2-1.1 B2-2.1 B-1.3 B-2'.9

Step-1: Synthesis of methyl 2-hydroxy-2-(3-(trifluoromethyl)phenyl)acetate (B2-2.1)

B2-2.1

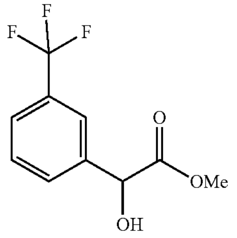

To a stirred solution of 3-(trifluoromethyl)benzaldehyde (B2-1.1, 25.00 g, 143 mmol) at 0° C. was added ZnI (4.50 g, 14.3 mmol), followed drop wise addition of trimethylsilyl cyanide (17.0 mL, 172.0 mmol) and resulting reaction mixture was stirred at 0° C. for 2 h. After this time, to the above reaction mixture HCl (4N in MeOH) (100 mL) was added at 0° C. The reaction mixture was allowed to warm to room temperature and stirred for 12 h. After this, the reaction mixture was concentrated under reduced pressure to get crude, which was quenched with saturated $NaHCO_3$ solution up to pH ~8, then added EtOAc (200 mL). The organic layer was washed with water (4×200 mL), followed by brine (200 mL). The organic layer was separated, dried over anhydrous sodium sulphate and concentrated under reduced pressure to afford methyl 2-hydroxy-2-(3-(trifluoromethyl)phenyl)acetate (B2-2.1, 28 g, yield: 83%) as a yellow liquid; ESI (m/z) 235 $[C_{10}H_9F_3O_3+H]^-$.

Step 2: Synthesis of 2-hydroxy-2-(3-(trifluoromethyl)phenyl)acetic acid (B-1.3)

B-1.3

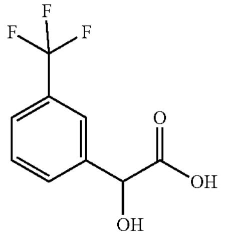

To a stirred solution of methyl 2-hydroxy-2-(3-(trifluoromethyl)phenyl)acetate (B2-2.1, 28 g, 119 mmol) in THF (70 mL), Water (20 mL), MeOH (50 mL), at room temperature LiOH (6.00 g, 143 mmol) was added and resulting reaction mixture was stirred for 12 h at same temperature. After this, the reaction mixture was concentrated under reduced pressure to get crude, which was quenched with water (100 mL). An aqueous layer was washed with EtOAc (200 mL) to remove impurities. Then water layer was acidified with 2N HCl (pH ~2), an aqueous layer extracted with EtOAc (2×150 mL). Combined organic layers were dried over anhydrous sodium sulphate and concentrated under reduced pressure to afford 2-hydroxy-2-(3-(trifluoromethyl)phenyl)acetic acid (B-1.3, 25.00 g, yield: 95%) as a color less liquid: ESI (m/z) 219.1 $[C_9H_7F_3O_3-H]^-$.

Step-3: Synthesis of 2-acetoxy-2-(3-(trifluoromethyl)phenyl)acetic acid (B-2'9)

B-2'.9

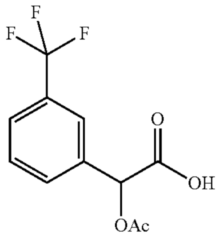

To a stirred solution of acetyl chloride (50 mL) at 0° C. was added 2-hydroxy-2-(3-trifluoro methyl)phenyl)acetic acid (B-1.3, 25.00 g, 113 mmol) portion wise over a period of 30 min. at same temperature. The reaction mixture was allowed to warm to room temperature and stirred for 1 h. After this time, the reaction mixture was concentrated under reduced pressure to get crude material followed by co-distilled with hexanes to afford 2-acetoxy-2-(3-(trifluoromethyl)phenyl)acetic acid (B-2'.9, 21.00 g, yield: 70%) as a white solid; $^{1}$H NMR (400 MHz, DMSO-$d_6$): δ 7.80 (t, J=8.0 Hz, 3H), 7.68 (t, J=8.0 Hz, 1H), 6.00 (s, 1H), 2.15 (s, 3H); ESI (m/z) 262.2 $[C_{11}H_9F_3O_4+H]^+$.

The compounds of formula B-2' (Table B32) can be synthesized according to the procedures described for compound B-2'.9

TABLE B2

| Compounds B-2': | | | |
|---|---|---|---|
| Compound | Name | Structure | MS |
| B-2'.9 | 2-acetoxy-2-(3-(trifluoromethyl)phenyl) acetic acid | 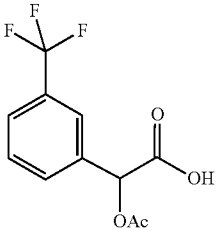 [SMILES: CC(=O)OC(C(=O)O)c1cccc(C(F)(F)F)c1] | ESI (m/z) 262.2 $[C_{11}H_9F_3O_4 + H]^+$ |
| B-2'.10 | 2-acetoxy-2-(3-ethylphenyl)acetic acid | 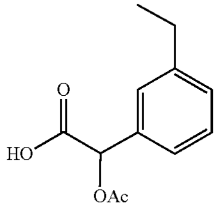 [SMILES: CCc1cccc(C(OC(C)=O)C(=O)O)c1] | ESI (m/z) 223 $[C_{12}H_{14}O_4 + H]^+$ |
| B-2'.11 | 2-acetoxy-2-(3-fluoro-5-(trifluoromethyl)phenyl) acetic acid | 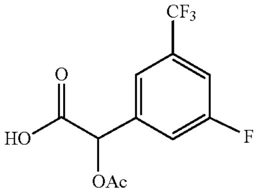 [SMILES: CC(=O)OC(C(=O)O)c1cc(F)cc(C(F)(F)F)c1] | ESI (m/z) 281 $[C_{11}H_8F_4O_4 + H]^+$ |
| B-2'.12 | 2-acetoxy-2-(3-ethyl-5-fluorophenyl)acetic acid | 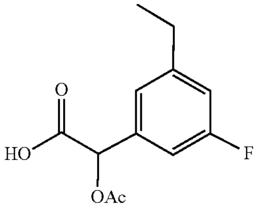 [SMILES: CCc1cc(F)cc(C(OC(C)=O)C(=O)O)c1] | ESI (m/z) 241 $[C_{12}H_{13}FO_4 + H]^+$ |
| B-2'.13 | 2-acetoxy-2-(m-tolyl)acetic acid | 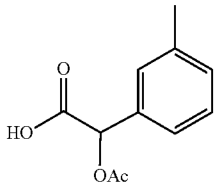 | ESI (m/z) 208.2 $[C_{11}H_{12}O_4 + H]^+$ |

Scheme C

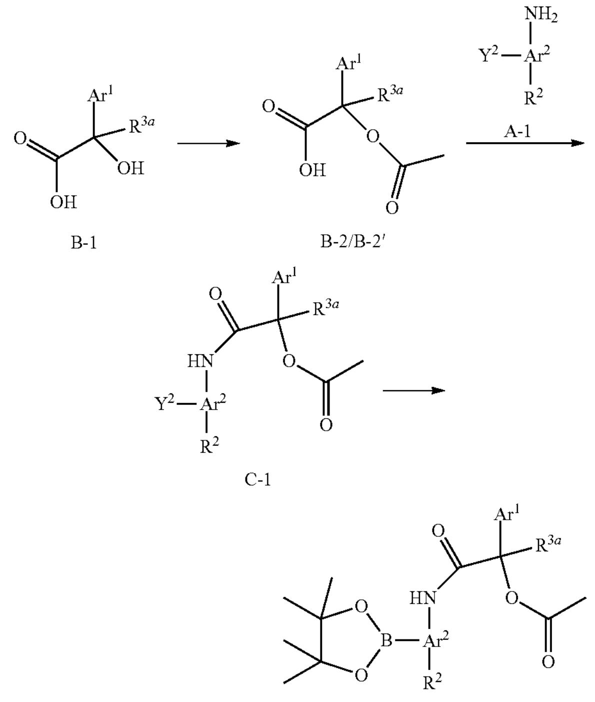

B-1 B-2/B-2' A-1 C-1 C-2

Compounds of Formula C-2 where $Ar^2$=phenyl, $R^2$=3—F, $Y^2$=Br, $R^{3a}$=H, $Ar^1$=phenyl-$R^1$ and $R^1$=3—F can be synthesized as described below for compound C-2.1

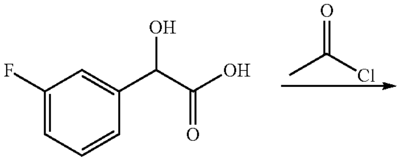

B-1.2

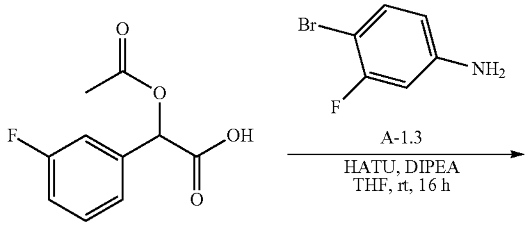

B-2.3 A-1.3

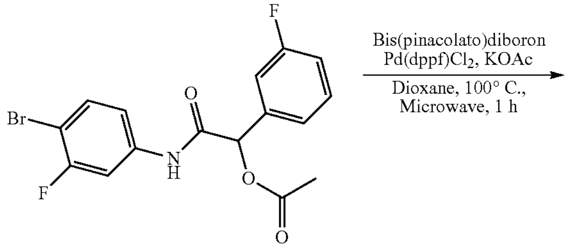

C-1.1

-continued

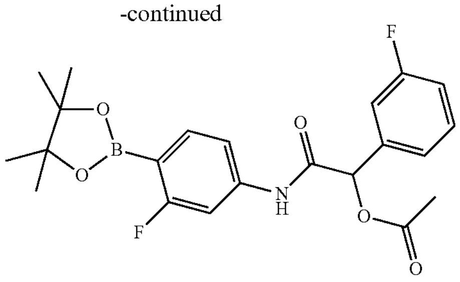

C-2.1

Step-1: Synthesis of 2-acetoxy-2-(3-fluorophenyl)acetic acid (B-2.3)

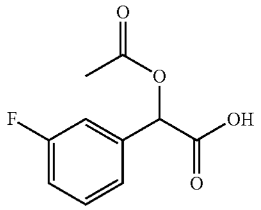

To a stirred solution of acetyl chloride (1.0 mL) at 0° C. was added 2-(3-fluorophenyl)-2-hydroxyacetic acid (B-1.2, 0.601 g, 3.53 mmol) portionwise. The reaction mixture was allowed to warm to room temperature and stirred for 1 h. After this time, the reaction mixture was concentrated to crude under vacuum and co-distilled with hexanes to afford 2-acetoxy-2-(3-fluorophenyl)acetic acid (B-2.3, 0.70 g, yield: 94%) as a white solid: ESI (m/z) 211 $[C_{10}H_9FO_4-H]^-$.

Step-2: Synthesis of 2-((4-bromo-3-fluorophenyl) amino)-1-(3-fluorophenyl)-2-oxoethyl acetate (C-1.1)

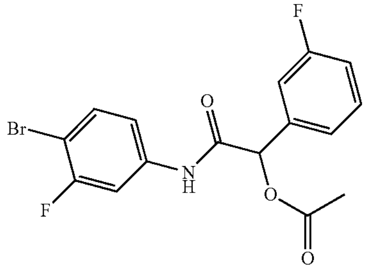 [SMILES: CC(=O)OC(C(=O)Nc1ccc(Br)c(F)c1)c1cccc(F)c1]

To a solution of 2-acetoxy-2-(3-fluorophenyl)acetic acid (B-2.3, 0.558 g, 2.63 mmol) and 4-bromo-3-fluoroaniline (A-1.3, 0.600 g, 3.16 mmol) in tetrahydrofuran (20 mL) were added N,N-diisopropylethylamine (0.90 mL, 5.3 mmol) followed by 1-[bis(dimethylamino)methylene]-1H-1,2,3-triazolo[4,5-b]pyridinium 3-oxid hexafluorophosphate (HATU) (1.50 g, 3.94 mmol) at room temperature and stirred for 16 h. After this time, the reaction mixture was diluted with dichloromethane (6.0 mL) and washed with water (4×4 mL) and brine (4 mL). The organic layer was separated, dried over anhydrous sodium sulfate and concentrated under reduced pressure. The crude product was purified by column chromatography (silica gel, 4% methanol/dichloromethane) to afford 2-((4-bromo-3-fluorophenyl)amino)-1-(3-fluorophenyl)-2-oxoethyl acetate (C-1.1, 500 mg, yield: 60%) as a pale brown solid: ESI (m/z) 385$[C_{16}H_{12}BrF_2NO_3]^+$.

Step-3: Synthesis of 2-((3-fluoro-4-(4,4,5,5-tetramethyl-1,3,2-dioxaborolan-2-yl)phenyl)amino)-1-(3-fluorophenyl)-2-oxoethyl acetate (C-2.1)

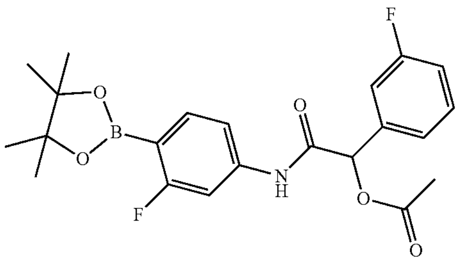 [SMILES: CC(=O)OC(C(=O)Nc1ccc(B2OC(C)(C)C(C)(C)O2)c(F)c1)c1cccc(F)c1]

To a stirred solution of 2-((4-bromo-3-fluorophenyl)amino)-1-(3-fluorophenyl)-2-oxoethyl acetate (C-1.1, 0.10 g, 0.26 mmol) in 1,4-dioxane (3.0 mL) under argon atmosphere were added bis(pinacolato)diboron (0.13 g, 0.52 mmol) and potassium acetate (51 mg, 0.52 mmol. The reaction mixture was purged with argon for 10 min. 1,1-Bis (diphenylphosphino)ferrocene-palladium(II)dichloride dichloromethane complex (9.5 mg, 0.01 mmol) was added and the mixture was purged with argon for 10 min. The reaction mixture was exposed to microwave irradiation (SEM Company) at 100° C. for 1 h. After this time, the reaction mixture was allowed to cool to room temperature, passed through a bed of diatomaceous earth, and washed with ethyl acetate (2×15 mL). The filtrate was washed with water (2×10 mL) and brine (2×10 mL). The organic layer was dried over anhydrous sodium sulfate and concentrated under reduced pressure. The crude product was purified by column chromatography (silica gel, 100 ethyl acetate/hexanes) to afford 2-((3-fluoro-4-(4,4,5,5-tetramethyl-1,3,2-dioxaborolan-2-yl)phenyl)amino)-1-(3-fluorophenyl)-2-oxoethyl acetate (C-2.1, 50 mg, yield: 600%) as a pale brown solid: ESI (m/z) 432 $[C_{22}H_{24}BF_2NO_5+H]^+$.

The compounds of formula C-2 (Table C) can be synthesized according to the procedures described for compound C-2.1:

TABLE C

Compounds C-2:

| Compound | Name | Structure | MS |
|---|---|---|---|
| C-2.1 | 2-((3-fluoro-4-(4,4,5,5-tetramethyl-1,3,2-dioxaborolan-2-yl)phenyl)amino)-1-(3-fluorophenyl)-2-oxoethyl acetate | 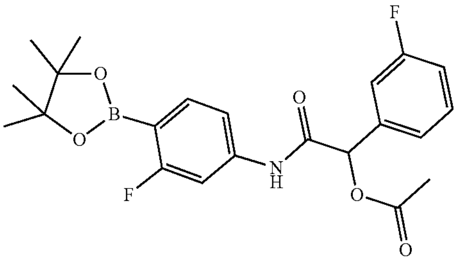 [SMILES: CC(=O)OC(C(=O)Nc1ccc(B2OC(C)(C)C(C)(C)O2)c(F)c1)c1cccc(F)c1] | ESI (m/z) 432 $[C_{22}H_{24}BF_2NO_5 + H]^+$ |
| C-2.2 | 1-(3-fluorophenyl)-2-((3-methyl-4-(4,4,5,5-tetramethyl-1,3,2-dioxaborolan-2-yl)phenyl)amino)-2-oxoethyl acetate | 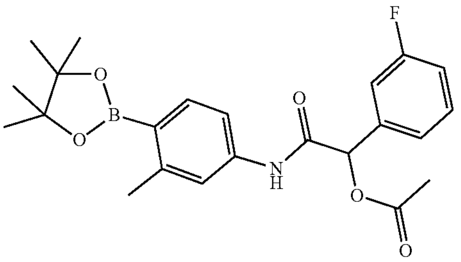 [SMILES: CC(=O)OC(C(=O)Nc1ccc(B2OC(C)(C)C(C)(C)O2)c(C)c1)c1cccc(F)c1] | ESI (m/z) 428 $[C_{23}H_{27}BFNO_5 + H]^+$ |
| C-2.3 | 2-((3-chloro-4-(4,4,5,5-tetramethyl-1,3,2-dioxaborolan-2-yl)phenyl)amino)-1-(3-fluorophenyl)-2-oxoethyl acetate | 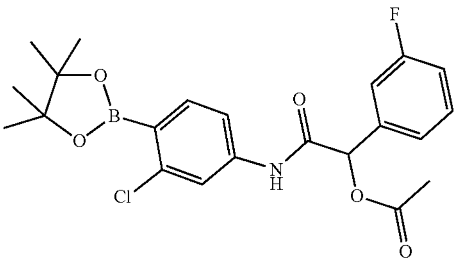 [SMILES: CC(=O)OC(C(=O)Nc1ccc(B2OC(C)(C)C(C)(C)O2)c(Cl)c1)c1cccc(F)c1] | ESI (m/z) 448, 450 $[C_{22}H_{24}BClFNO_5 + H]^+$ |

TABLE C-continued

| Compounds C-2: | | | |
|---|---|---|---|
| Compound | Name | Structure | MS |
| C-2.4 | 1-(3-fluorophenyl)-2-oxo-2-((4-(4,4,5,5-tetramethyl-1,3,2-dioxaborolan-2-yl)-3-(trifluoromethyl)phenyl) amino)ethyl acetate | 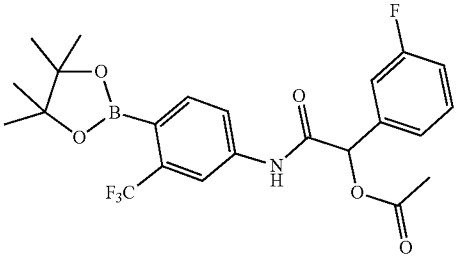 [SMILES: CC(=O)OC(C(=O)Nc1ccc(B2OC(C)(C)C(C)(C)O2)c(C(F)(F)F)c1)c1cccc(F)c1] | ESI (m/z) 482 [$C_{23}H_{24}BF_4NO_5$ + H]$^+$ |
| C-2.5 | 1-(3-fluorophenyl)-2-oxo-2-((4-(4,4,5,5-tetramethyl-1,3,2-dioxaborolan-2-yl)-3-(trifluoromethoxy)phenyl) amino)ethyl acetate | 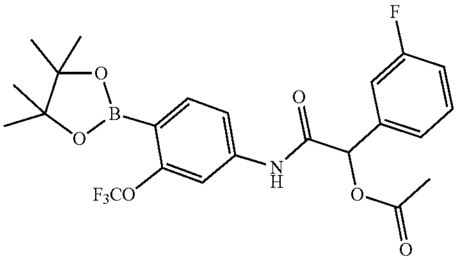 [SMILES: CC(=O)OC(C(=O)Nc1ccc(B2OC(C)(C)C(C)(C)O2)c(OC(F)(F)F)c1)c1cccc(F)c1] | ESI (m/z) 498 [$C_{23}H_{24}BF_4NO_6$ + H]$^+$ |
| C-2.6 | 2-((3-chloro-4-(4,4,5,5-tetramethyl-1,3,2-dioxaborolan-2-yl)phenyl)amino)-1-(3,5-difluorophenyl)-2-oxoethyl acetate | 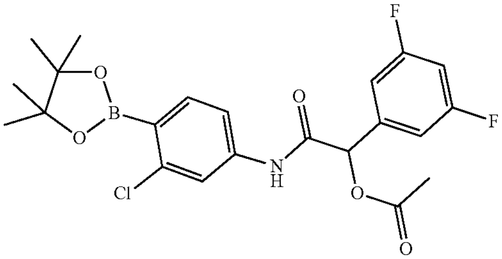 [SMILES: CC(=O)OC(C(=O)Nc1ccc(B2OC(C)(C)C(C)(C)O2)c(Cl)c1)c1cc(F)cc(F)c1] | ESI (m/z) 466 [$C_{22}H_{23}BClF_2NO_5$ + H]$^+$ |
| C-2.7 | (R)-2-((3-chloro-4-(4,4,5,5-tetramethyl-1,3,2-dioxaborolan-2-yl)phenyl)amino)-1-(3-fluorophenyl)-2-oxoethyl acetate | 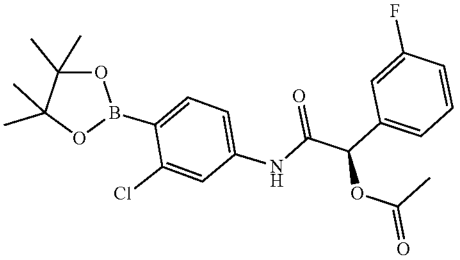 [SMILES: CC(=O)O[C@@H](C(=O)Nc1ccc(B2OC(C)(C)C(C)(C)O2)c(Cl)c1)c1cccc(F)c1] | ESI (m/z) 448, 450 [$C_{22}H_{24}BClFNO_5$ + H]$^+$ |
| C-2.8 | 1-(3-fluorophenyl)-2-((3-methoxy-4-(4,4,5,5-tetramethyl-1,3,2-dioxaborolan-2-yl)phenyl)amino)-2-oxoethyl acetate | 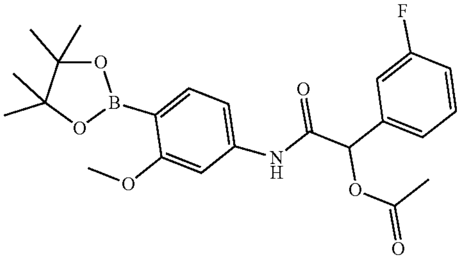 [SMILES: COc1cc(NC(=O)C(OC(C)=O)c2cccc(F)c2)ccc1B1OC(C)(C)C(C)(C)O1] | ESI (m/z) 444 [$C_{23}H_{27}BFNO_6$ + H]$^+$ |
| C-2.9 | N-(3-ethyl-4-(4,4,5,5-tetramethyl-1,3,2-dioxaborolan-2-yl)phenyl)-2-(3-fluorophenyl)-2-hydroxyacetamide | 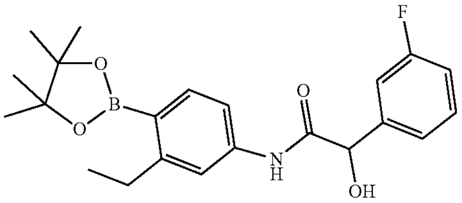 | ESI (m/z) 400 [$C_{27}H_{27}BFNO_4$ + H]$^+$ |

TABLE C-continued

| Compounds C-2: | | | |
|---|---|---|---|
| Compound | Name | Structure | MS |
| C-2.10 | 2-((2-fluoro-3-methyl-4-(4,4,5,5-tetramethyl-1,3,2-dioxaborolan-2-yl)phenyl)amino)-1-(3-fluorophenyl)-2-oxoethyl acetate | 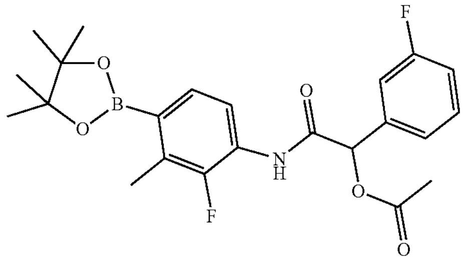 [SMILES: CC(=O)OC(C(=O)Nc1ccc(B2OC(C)(C)C(C)(C)O2)c(C)c1F)c1cccc(F)c1] | ESI (m/z) 446 $[C_{23}H_{26}BF_2NO_5 + H]^+$ |
| C-2.11 | 2-((3,5-dimethyl-4-(4,4,5,5-tetramethyl-1,3,2-dioxaborolan-2-yl)phenyl)amino)-1-(3-fluorophenyl)-2-oxoethyl acetate | 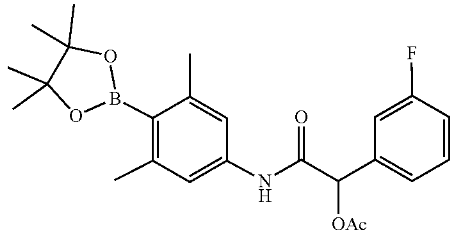 [SMILES: CC(=O)OC(C(=O)Nc1cc(C)c(B2OC(C)(C)C(C)(C)O2)c(C)c1)c1cccc(F)c1] | ESI (m/z) 442 $[C_{24}H_{29}BFNO_5 + H]^+$ |
| C-2.12 | 2-((2-fluoro-5-methyl-4-(4,4,5,5-tetramethyl-1,3,2-dioxaborolan-2-yl) phenyl)amino)-1-(3-fluorophenyl)-2-oxoethyl acetate | 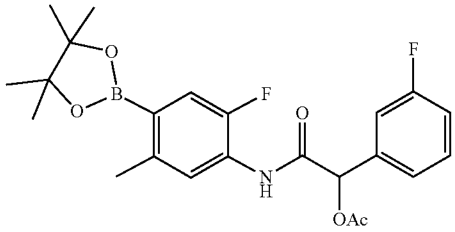 | ESI (m/z) 466 $[C_{23}H_{26}BF_2NO_5 + H]^+$ |
| C-2.13 | 2-((2,5-difluoro-4-(4,4,5,5-tetramethyl-1,3,2-dioxaborolan-2-yl)phenyl)amino)-1-(3-fluorophenyl)-2-oxoethyl acetate | 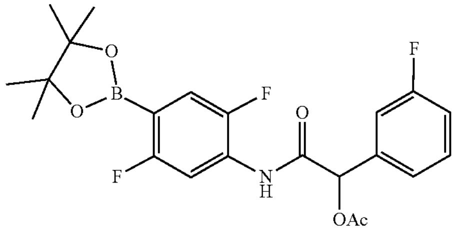 [SMILES: CC(=O)OC(C(=O)Nc1cc(F)c(B2OC(C)(C)C(C)(C)O2)cc1F)c1cccc(F)c1] | ESI (m/z) 450 $[C_{22}H_{23}BF_3NO_5 + H]^+$ |
| C-2.14 | 2-((3-fluoro-5-methyl-4-(4,4,5,5-tetramethyl-1,3,2-dioxaborolan-2-yl)phenyl)amino)-1-(3-fluorophenyl)-2-oxoethyl acetate | 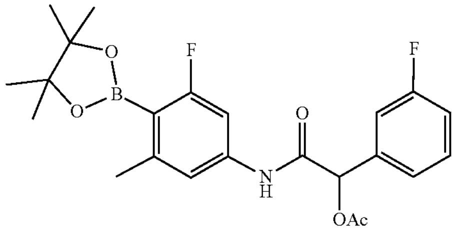 [SMILES: CC(=O)OC(C(=O)Nc1cc(C)c(B2OC(C)(C)C(C)(C)O2)c(F)c1)c1cccc(F)c1] | ESI (m/z) 446 $[C_{23}H_{26}BF_2NO_5 + H]^+$ |
| C-2.15 | 1-(3-fluorophenyl)-2-((6-methyl-5-(4,4,5,5-tetramethyl-1,3,2-dioxaborolan-2-yl)pyridin-2-yl)amino)-2-oxoethyl acetate | 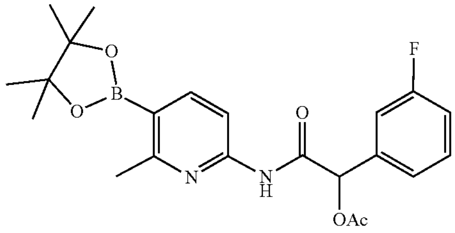 [SMILES: CC(=O)OC(C(=O)Nc1ccc(B2OC(C)(C)C(C)(C)O2)c(C)n1)c1cccc(F)c1] | ESI (m/z) 429 $[C_{22}H_{26}BFN_2O_5 + H]^+$ |

TABLE C-continued

| Compounds C-2: | | | |
|---|---|---|---|
| Compound | Name | Structure | MS |
| C-2.16 | 1-(3-fluorophenyl)-2-((4-methyl-5-(4,4,5,5-tetramethyl-1,3,2-dioxaborolan-2-yl)pyridin-2-yl)amino)-2-oxoethyl acetate | 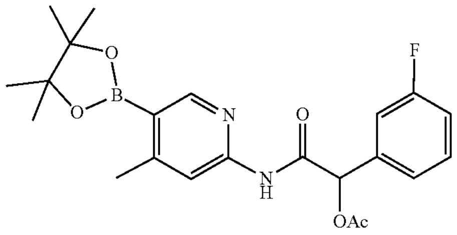 [SMILES: CC(=O)OC(C(=O)Nc1cc(C)c(B2OC(C)(C)C(C)(C)O2)cn1)c1cccc(F)c1] | ESI (m/z) 429 $[C_{22}H_{26}BFN_2O_5 + H]^+$ |
| C-2.17 | 2-((4-methyl-5-(4,4,5,5-tetramethyl-1,3,2-dioxaborolan-2-yl)pyridin-2-yl)amino)-2-oxo-1-(3-(trifluoromethyl)phenyl) ethyl acetate | 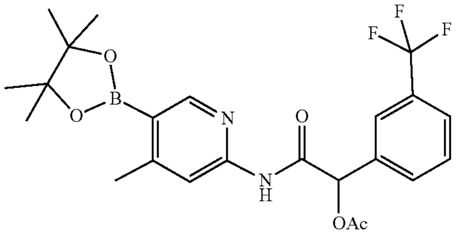 [SMILES: CC(=O)OC(C(=O)Nc1cc(C)c(B2OC(C)(C)C(C)(C)O2)cn1)c1cccc(C(F)(F)F)c1] | ESI (m/z) 479 $[C_{23}H_{26}BF_3N_2O_5 + H]^+$ |
| C-2.18 | 2-((6-methyl-5-(4,4,5,5-tetramethyl-1,3,2-dioxaborolan-2-yl)pyridin-2-yl)amino)-2-oxo-1-(3-(trifluoromethyl)phenyl) ethyl acetate | 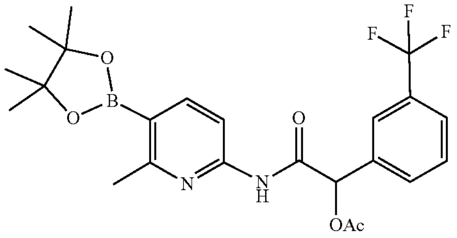 [SMILES: CC(=O)OC(C(=O)Nc1ccc(B2OC(C)(C)C(C)(C)O2)c(C)n1)c1cccc(C(F)(F)F)c1] | ESI (m/z) 479 $[C_{23}H_{26}BF_3N_2O_5 + H]^+$. |
| C-2.19 | 2-((3-methyl-4-(4,4,5,5-tetramethyl-1,3,2-dioxaborolan-2-yl)phenyl)amino)-2-oxo-1-(6-(trifluoromethyl) pyridin-2-yl)ethyl acetate | 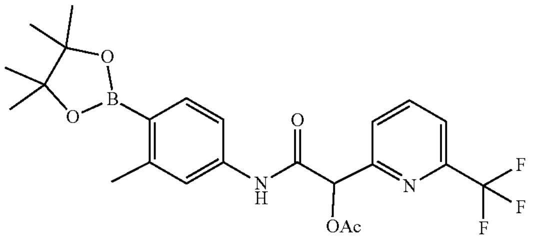 [SMILES: CC(=O)OC(C(=O)Nc1ccc(B2OC(C)(C)C(C)(C)O2)c(C)c1)c1cccc(C(F)(F)F)n1] | ESI (m/z) 479 $[C_{23}H_{26}BF_3N_2O_5 + H]^+$. |
| C-2.20 | 2-((3-methyl-4-(4,4,5,5-tetramethyl-1,3,2-dioxaborolan-2-yl)phenyl)amino)-1-(6-methylpyridin-2-yl)-2-oxoethyl acetate | 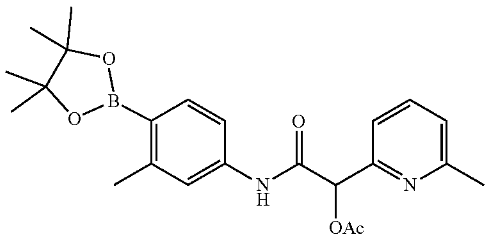 | ESI (m/z) 425 $[C_{23}H_{29}BN_2O_5 + H]^+$. |

Scheme D

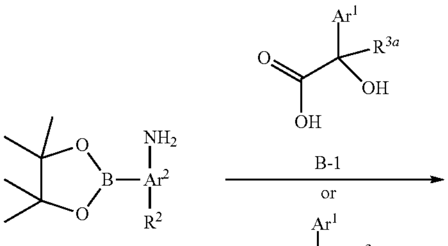

A-2

B-2/B-2'

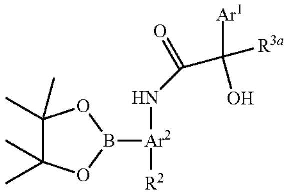

D-1 or

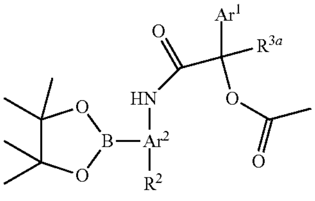

D-1a

Compounds of Formula D-1 where $Ar^2$=phenyl, $R^2$=3-methyl, $R^{3a}$=H, $Ar^1$=phenyl-$R^1$ and $R^1$=3—F can be synthesized as described below for compound D-1.1:

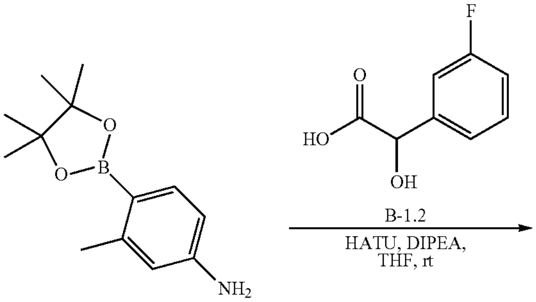

B-1.2

A-2.1

-continued

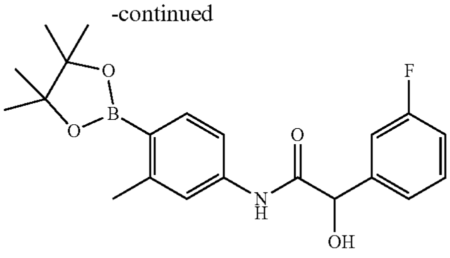

D-1.1

Synthesis of 2-(3-fluorophenyl)-2-hydroxy-N-(3-methyl-4-(4,4,5,5-tetramethyl-1,3,2-dioxaborolan-2-yl)phenyl)acetamide (D-1.1)

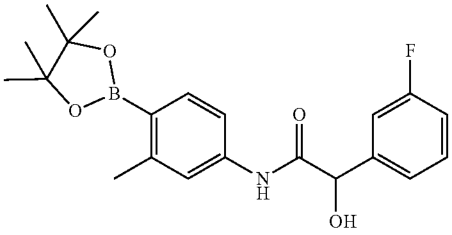 [SMILES: Cc1cc(NC(=O)C(O)c2cccc(F)c2)ccc1B1OC(C)(C)C(C)(C)O1]

To a solution of 3-methyl-4-(4,4,5,5-tetramethyl-1,3,2-dioxaborolan-2-yl)aniline (A-2.1, 0.298 g, 1.28 mmol) and 2-(3-fluorophenyl)-2-hydroxyacetic acid (B-1.2, 0.196 g, 1.15 mmol) in tetrahydrofuran (10 mL) were added N,N-disopropylethyl amine (0.26 mL, 1.5 mmol) followed by 1-[bis(dimethylamino)methylene]-1H-1,2,3-triazolo[4,5-b]pyridinium 3-oxid hexafluorophosphate (HATU) (0.586, 1.54 mmol) at 0'C. The reaction mixture was allowed to warm to room temperature and stirred for 12 h. After this time, the reaction D mixture was diluted with methylene chloride (6.0 mL) and washed with water (4×4 mL) and brine (4 mL). The organic layer was separated, dried over anhydrous sodium sulfate, and concentrated under reduced pressure. The crude product was purified by column chromatography (silica gel, 40 methanol/dichloromethane) to afford 2-(3-fluorophenyl)-2-hydroxy-N-(3-methyl-4-(4,4,5,5-tetramethyl-1,3,2-dioxaborolan-2-yl)phenyl)acetamide (D-1.1, 0.25 g, yield: 52 d) as a pale brown solid: ESI (m/z) 386 $[C_{24}H_{25}BFNO_4+H]^+$.

The compounds of formula D-1 (Table D) can be synthesized according to the procedures described for compound D-1.1:

TABLE D

| Compounds D-1: | | | |
|---|---|---|---|
| Compound | Name | Structure | MS |
| D-1.1 | 2-(3-fluorophenyl)-2-hydroxy-N-(3-methyl-4-(4,4,5,5-tetramethyl-1,3,2-dioxaborolan-2-yl)phenyl) acetamide | 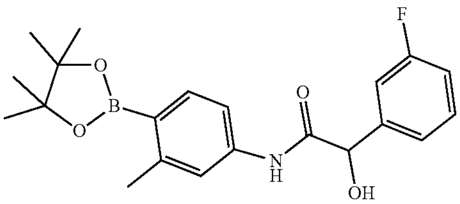 [SMILES: Cc1cc(NC(=O)C(O)c2cccc(F)c2)ccc1B1OC(C)(C)C(C)(C)O1] | ESI (m/z) 386 $[C_{21}H_{25}BFNO_4 + H]^+$ |
| D-1.2 | N-(2,3-difluoro-4-(4,4,5,5-tetramethyl-1,3,2-dioxaborolan-2-yl) phenyl)-2-(3-fluorophenyl)-2-hydroxyacetamide | 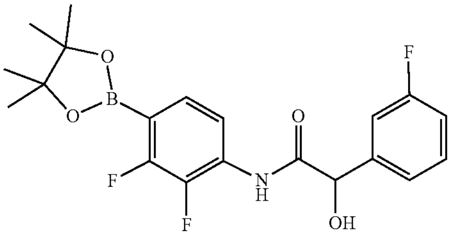 [SMILES: CC1(C)OB(c2ccc(NC(=O)C(O)c3cccc(F)c3)c(F)c2F)OC1(C)C] | ESI (m/z) 408 $[C_{20}H_{21}BF_3NO_4 + H]^+$ |
| D-1.3 | 1-(3-fluorophenyl)-2-((3-methyl-4-(4,4,5,5-tetramethyl-1,3,2-dioxaborolan-2-yl)phenyl)amino)-2-oxoethyl acetate | 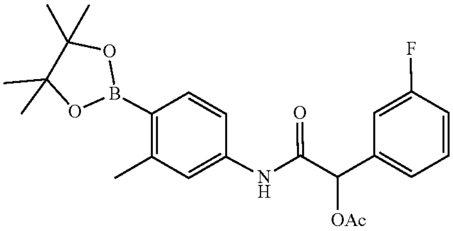 [SMILES: CC(=O)OC(C(=O)Nc1ccc(B2OC(C)(C)C(C)(C)O2)c(C)c1)c1cccc(F)c1] | ESI (m/z) 428 $[C_{23}H_{27}BFNO_5 + H]^+$ |
| D-1.4 | 1-(3,5-difluorophenyl)-2-((3-methyl-4-(4,4,5,5-tetramethyl-1,3,2-dioxaborolan-2-yl)phenyl)amino)-2-oxoethyl acetate | 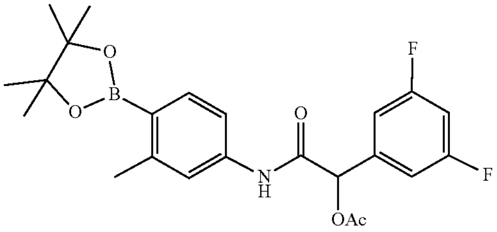 [SMILES: CC(=O)OC(C(=O)Nc1ccc(B2OC(C)(C)C(C)(C)O2)c(C)c1)c1cc(F)cc(F)c1] | ESI (m/z) 446 $[C_{23}H_{26}BF_2NO_5 + H]^+$ |
| D-1.5 | 1-(3-fluoro-5-(trifluoromethyl) phenyl)-2-((3-methyl-4-(4,4,5,5-tetramethyl-1,3,2-dioxaborolan-2-yl)phenyl)amino)-2-oxoethyl acetate | 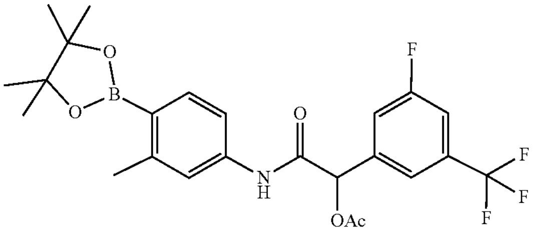 [SMILES: CC(=O)OC(C(=O)Nc1ccc(B2OC(C)(C)C(C)(C)O2)c(C)c1)c1cc(F)cc(C(F)(F)F)c1] | ESI (m/z) 496 $[C_{24}H_{26}BF_4NO_5 + H]^+$ |
| D-1.6 | 1-(3-fluoro-5-methylphenyl)-2-((3-methyl-4-(4,4,5,5-tetramethyl-1,3,2-dioxaborolan-2-yl)phenyl)amino)-2-oxoethyl acetate | 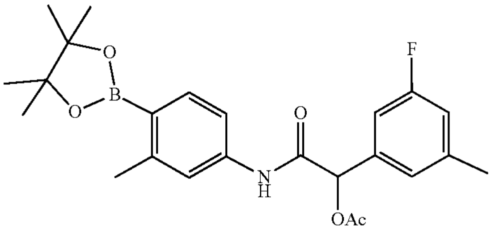 | ESI (m/z) 442 $[C_{24}H_{29}BFNO_5 + H]^+$ |

TABLE D-continued

| Compounds D-1: | | | |
|---|---|---|---|
| Compound | Name | Structure | MS |
| D-1.7 | 2-((3-ethyl-4-(4,4,5,5-tetramethyl-1,3,2-dioxaborolan-2-yl)phenyl)amino)-1-(3-fluorophenyl)-2-oxoethyl acetate | 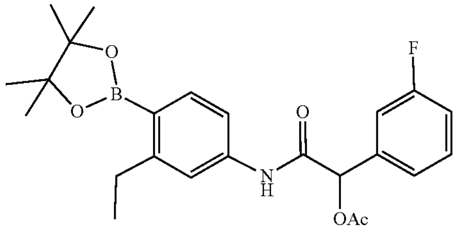 [SMILES: CCc1cc(NC(=O)C(OC(C)=O)c2cccc(F)c2)ccc1B1OC(C)(C)C(C)(C)O1] | ESI (m/z) 442 $[C_{24}H_{29}BFNO_5 + H]^+$ |
| D-1.8 | 1-(3-fluorophenyl)-2-oxo-2-((4-(4,4,5,5-tetramethyl-1,3,2-dioxaborolan-2-yl)phenyl)amino) ethyl acetate | 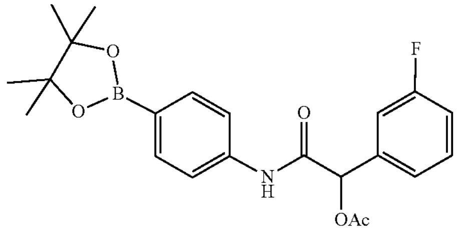 [SMILES: CC(=O)OC(C(=O)Nc1ccc(B2OC(C)(C)C(C)(C)O2)cc1)c1cccc(F)c1] | ESI (m/z) 414 $[C_{22}H_{25}BFNO_5 + H]^+$ |
| D-1.9 | 2-((3-fluoro-4-(4,4,5,5-tetramethyl-1,3,2-dioxaborolan-2-yl)phenyl)amino)-1-(3-fluorophenyl)-2-oxoethyl acetate | 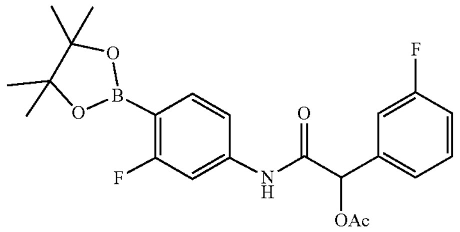 | ESI (m/z) 432 $[C_{22}H_{24}BF_2NO_5 + H]^+$ |
| D-1.10 | 1-(3-chlorophenyl)-2-((3-fluoro-4-(4,4,5,5-tetramethyl-1,3,2-dioxaborolan-2-yl)phenyl)amino)-2-oxoethyl acetate | 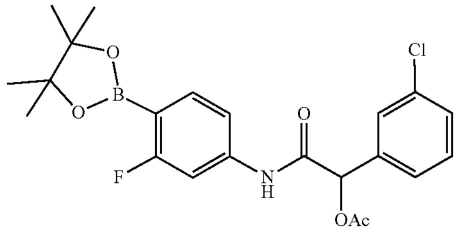 [SMILES: CC(=O)OC(C(=O)Nc1ccc(B2OC(C)(C)C(C)(C)O2)c(F)c1)c1cccc(Cl)c1] | ESI (m/z) 447 $[C_{22}H_{24}BClFNO_5 + H]^+$ |
| D-1.11 | 2-((3-fluoro-4-(4,4,5,5-tetramethyl-1,3,2-dioxaborolan-2-yl)phenyl)amino)-2-oxo-1-(m-tolyl)ethyl acetate | 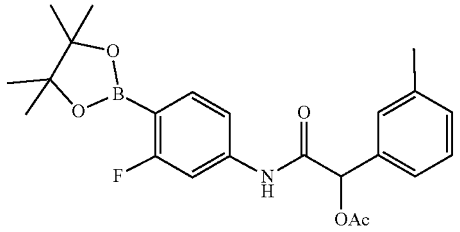 [SMILES: CC(=O)OC(C(=O)Nc1ccc(B2OC(C)(C)C(C)(C)O2)c(F)c1)c1cccc(C)c1] | ESI (m/z) 428 $[C_{23}H_{27}BFNO_5 + H]^+$ |
| D-1.12 | 2-((3-fluoro-4-(4,4,5,5-tetramethyl-1,3,2-dioxaborolan-2-yl)phenyl)amino)-2-oxo-1-(3-(trifluoromethyl) phenyl)ethyl acetate | 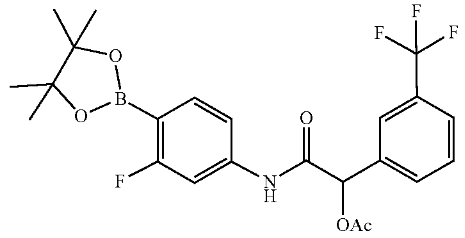 [SMILES: CC(=O)OC(C(=O)Nc1ccc(B2OC(C)(C)C(C)(C)O2)c(F)c1)c1cccc(C(F)(F)F)c1] | ESI (m/z) 482 $[C_{23}H_{24}BF_4NO_5 + H]^+$ |

TABLE D-continued

| Compounds D-1: | | | |
|---|---|---|---|
| Compound | Name | Structure | MS |
| D-1.13 | 1-(3,5-difluorophenyl)-2-((3-fluoro-4-(4,4,5,5-tetramethyl-1,3,2-dioxaborolan-2-yl)phenyl)amino)-2-oxoethyl acetate | 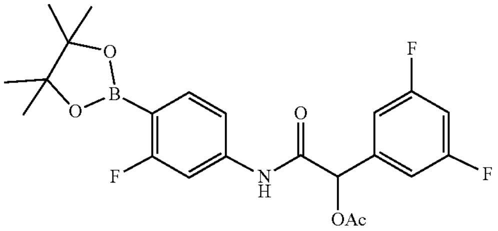 [SMILES: CC(=O)OC(C(=O)Nc1ccc(B2OC(C)(C)C(C)(C)O2)c(F)c1)c1cc(F)cc(F)c1] | ESI (m/z) 450 $[C_{22}H_{23}BF_3NO_5 + H]^+$ |
| D-1.14 | 2-((3-fluoro-4-(4,4,5,5-tetramethyl-1,3,2-dioxaborolan-2-yl)phenyl)amino)-1-(3-fluoro-5-(trifluoromethyl) phenyl)-2-oxoethyl acetate | 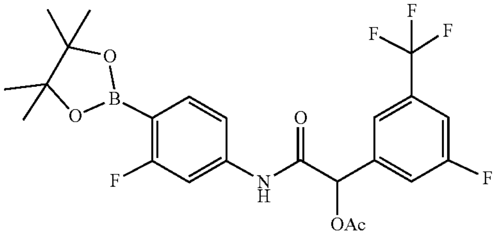 [SMILES: CC(=O)OC(C(=O)Nc1ccc(B2OC(C)(C)C(C)(C)O2)c(F)c1)c1cc(F)cc(C(F)(F)F)c1] | ESI (m/z) 500 $[C_{23}H_{23}BF_5NO_5 + H]^+$ |
| D-1.15 | 2-((2-fluoro-4-(4,4,5,5-tetramethyl-1,3,2-dioxaborolan-2-yl)phenyl)amino)-1-(3-fluorophenyl)-2-oxoethyl acetate | 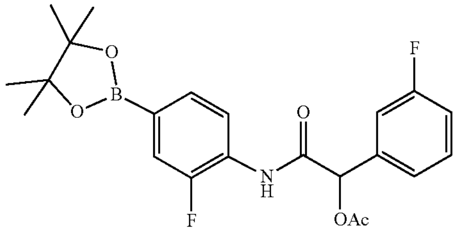 [SMILES: CC(=O)OC(C(=O)Nc1ccc(B2OC(C)(C)C(C)(C)O2)cc1F)c1cccc(F)c1] | ESI (m/z) 432 $[C_{22}H_{24}BF_2NO_5 + H]^+$ |
| D-1.16 | 1-(3-fluorophenyl)-2-oxo-2-((4-(4,4,5,5-tetramethyl-1,3,2-dioxaborolan-2-yl)-3-(trifluoromethoxy) phenyl)amino)ethyl acetate | 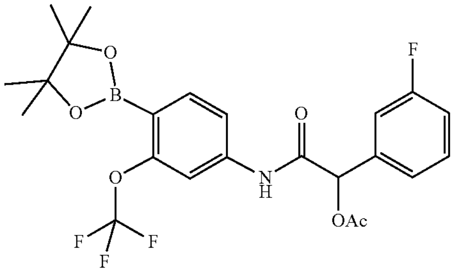 [SMILES: CC(=O)OC(C(=O)Nc1ccc(B2OC(C)(C)C(C)(C)O2)c(OC(F)(F)F)c1)c1cccc(F)c1] | ESI (m/z) 498 $[C_{23}H_{24}BF_4NO_6 + H]^+$ |
| D-1.17 | 1-(3-chlorophenyl)-2-((2,3-difluoro-4-(4,4,5,5-tetramethyl-1,3,2-dioxaborolan-2-yl)phenyl)amino)-2-oxoethyl acetate | 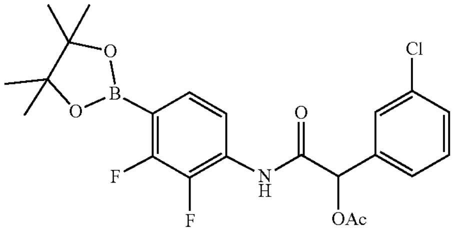 [SMILES: CC(=O)OC(C(=O)Nc1ccc(B2OC(C)(C)C(C)(C)O2)c(F)c1F)c1cccc(Cl)c1] | ESI (m/z) 465 $[C_{22}H_{23}BClF_2NO_5 + H]^+$ |
| D-1.18 | 2-((2,3-difluoro-4-(4,4,5,5-tetramethyl-1,3,2-dioxaborolan-2-yl)phenyl)amino)-2-oxo-1-(3-(trifluoromethyl) phenyl)ethyl acetate | 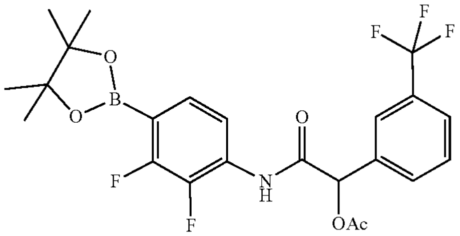 [SMILES: CC(=O)OC(C(=O)Nc1ccc(B2OC(C)(C)C(C)(C)O2)c(F)c1F)c1cccc(C(F)(F)F)c1] | ESI (m/z) 500 $[C_{23}H_{23}BF_5NO_5 + H]^+$ |

TABLE D-continued

| Compounds D-1: | | | |
|---|---|---|---|
| Compound | Name | Structure | MS |
| D-1.19 | 2-((2,3-difluoro-4-(4,4,5,5-tetramethyl-1,3,2-dioxaborolan-2-yl)phenyl)amino)-1-(3,5-difluorophenyl)-2-oxoethyl acetate | 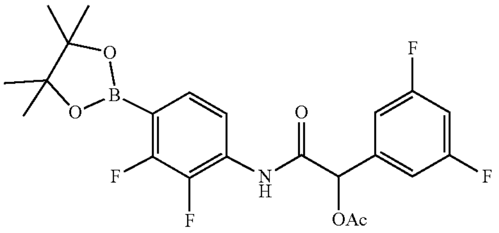 [SMILES: CC(=O)OC(C(=O)Nc1ccc(B2OC(C)(C)C(C)(C)O2)c(F)c1F)c1cc(F)cc(F)c1] | ESI (m/z) 468 [$C_{22}H_{22}BF_4NO_5$ + H]$^+$ |
| D-1.20 | 2-((2,3-difluoro-4-(4,4,5,5-tetramethyl-1,3,2-dioxaborolan-2-yl)phenyl)amino)-1-(3-fluoro-5-(trifluoromethyl)phenyl)-2-oxoethyl acetate | 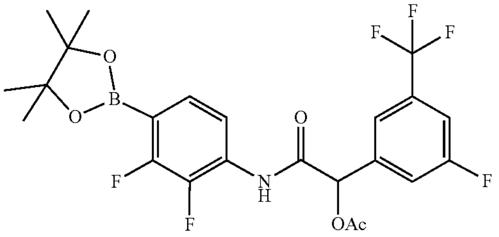 [SMILES: CC(=O)OC(C(=O)Nc1ccc(B2OC(C)(C)C(C)(C)O2)c(F)c1F)c1cc(F)cc(C(F)(F)F)c1] | ESI (m/z) 418 [$C_{23}H_{22}BF_6NO_5$ + H]$^+$ |
| D-1.21 | 1-(2,3-dihydrobenzofuran-7-yl)-2-((3-methyl-4-(4,4,5,5-tetramethyl-1,3,2-dioxaborolan-2-yl)phenyl)amino)-2-oxoethyl acetate | 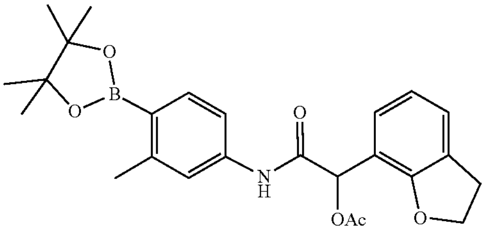 [SMILES: CC(=O)OC(C(=O)Nc1ccc(B2OC(C)(C)C(C)(C)O2)c(C)c1)c1cccc2c1OCC2] | ESI (m/z) 452 [$C_{25}H_{30}BNO_6$ + H]$^+$ |
| D-1.22 | 1-(1-methyl-1H-indazol-7-yl)-2-((3-methyl-4-(4,4,5,5-tetramethyl-1,3,2-dioxaborolan-2-yl)phenyl)amino)-2-oxoethyl acetate | 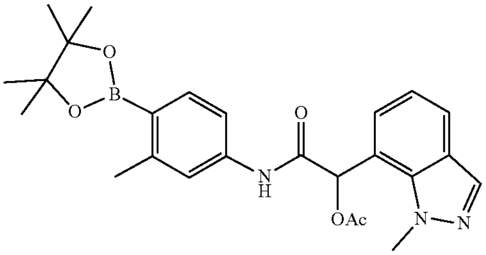 [SMILES: CC(=O)OC(C(=O)Nc1ccc(B2OC(C)(C)C(C)(C)O2)c(C)c1)c1cccc2cnn(C)c12] | ESI (m/z) 464 [$C_{25}H_{30}BN_3O_5$ + H]$^+$ |
| D-1.23 | 2,2-difluoro-N-(3-methyl-4-(4,4,5,5-tetramethyl-1,3,2-dioxaborolan-2-yl)phenyl)-2-phenylacetamide | 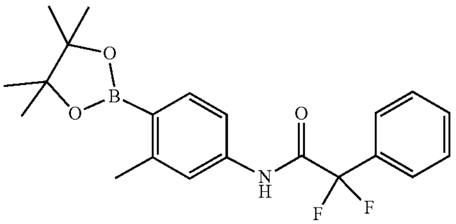 [SMILES: Cc1cc(NC(=O)C(F)(F)c2ccccc2)ccc1B1OC(C)(C)C(C)(C)O1] | ESI (m/z) 388 [$C_{21}H_{24}BF_2NO_3$ + H]$^+$ |

Scheme E

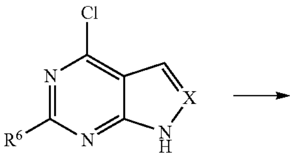

E-1

-continued

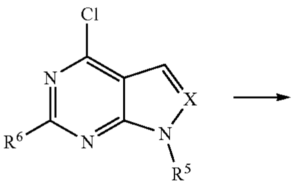

E-2

-continued

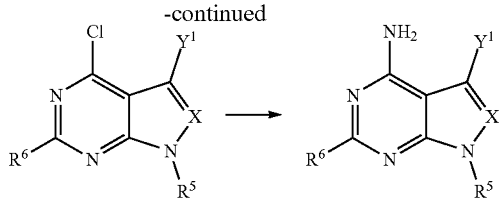

E-3 E-4

Compounds of Formula E-4 where X═CH, $R^5$=methyl, $R^6$=methyl and $Y^1$═Br can be synthesized as described for compound E-4.1:

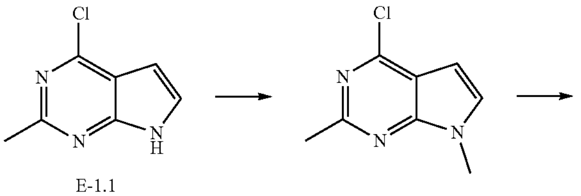

E-1.1 E-2.1

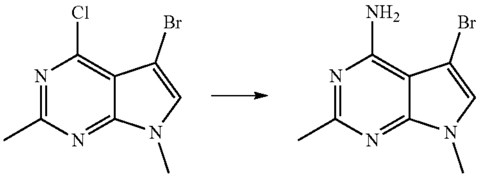

E-3.1 E-4.1

Step-1: Synthesis of 4-chloro-2,7-dimethyl-7H-pyrrolo[2,3-d]pyrimidine (E-2.1)

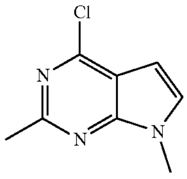

To a stirred solution of 4-chloro-2-methyl-7H-pyrrolo[2,3-d]pyrimidine (E-1.1, 2.50 g, 14.9 mmol) in N-methyl-2-pyrrolidone (15 mL) was added cesium carbonate (9.71 g, 29.8 mmol) at 10° C. After 15 min, methyl iodide (2.32 g, 1.0 mL, 16.4 mmol) was added dropwise at room temperature, and the mixture was stirred under argon atmosphere at ambient temperature for 4 h. After this time, the reaction mixture was poured into ice cold water (20 mL) and stirred for 30 min. The resulting solid was isolated by filtration and dried under vacuum to afford 4-chloro-2,7-dimethyl-7H-pyrrolo[2,3-d]pyrimidine (E-2.1, 2.0 g, yield: 74%) as a pale brown solid: ESI (m/z) 182 $[C_8H_8ClN_3+H]^+$.

Step-2: Synthesis of 5-bromo-4-chloro-2,7-dimethyl-7H-pyrrolo[2,3-d]pyrimidine (E-3.1)

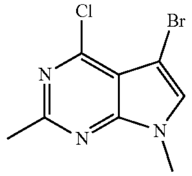

To a stirred solution of 4-chloro-2,7-dimethyl-7H-pyrrolo[2,3-d]pyrimidine (E-2.1, 2.00 g, 11.0 mmol) in dichloromethane (18 mL) was added N-bromosuccinimide (2.10 g, 12.1 mmol) portion-wise at 0° C. The resulting mixture was warmed to ambient temperature, and stirring continued for 2 h. After this time, the reaction mixture was filtered, and the isolated solid was washed with water (20 mL) and dried to afford 5-bromo-4-chloro-2,7-dimethyl-7H-pyrrolo[2,3-d]pyrimidine (E-3.1, 1.80 g, yield: 63%) as a light brown solid: ESI (m/z) 260, 262 $[C_8H_7BrClN_3+H]^+$.

Step-3: Synthesis of 5-bromo-2,7-dimethyl-7H-pyrrolo[2,3-d]pyrimidin-4-amine (E-4.1)

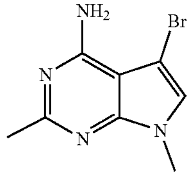

A solution of 5-bromo-4-chloro-2,7-dimethyl-7H-pyrrolo[2,3-d]pyrimidine (E-3.1, 1.80 g, 6.90 mmol) in 25% aqueous ammonia (17 mL) was stirred in a 100 mL autoclave. The reaction mixture was heated to 120° C. and stirred for 16 h. After this time, the reaction mixture was allowed to cool to room temperature. The resulting solid was isolated by filtration, washed with water (25 mL), and dried to afford 5-bromo-2,7-dimethyl-7H-pyrrolo[2,3-d]pyrimidin-4-amine (E-4.1, 1.20 g, yield: 72%) as a light grey solid: ESI (m/z) 241, 243 $[C_8H_9BrN_4+H]^+$.

The compounds of Formula E-4 (Table E) can be synthesized according to the procedures described for compound E-4.1:

TABLE E

| Compounds E-4: | | | |
|---|---|---|---|
| Compound | Name | Structure | MS |
| E-4.1 | 5-bromo-2,7-dimethyl-7H-pyrrolo[2,3-d]pyrimidin-4-amine | 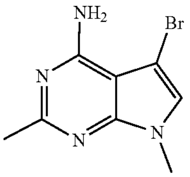 | ESI (m/z) 241, 243 $[C_8H_9BrN_4 + H]^+$ |
| E-4.2 | 5-bromo-7-methyl-7H-pyrrolo[2,3-d]pyrimidin-4-amine | 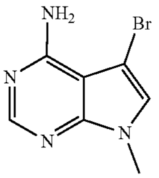 | ESI (m/z) 241, 243 $[C_7H_7BrN_4 + H]^+$ |
| E-4.4 | 5-bromo-2-isopropyl-7-methyl-7H-pyrrolo[2,3-d]pyrimidin-4-amine | 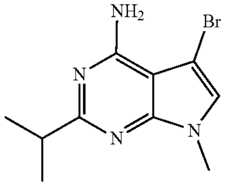 | ESI (m/z) 269 $[C_{10}H_{13}BrN_4 + H]^+$ |
| E-4.5 | 5-iodo-7-methyl-2-(trifluoromethyl)-7H-pyrrolo[2,3-d]pyrimidin-4-amine | 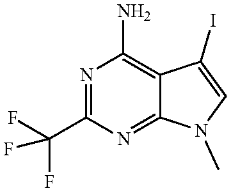 [SMILES: Cn1cc(I)c2c(N)nc(C(F)(F)F)nc21] | Compound does not ionize. $^1$H-NMR (400 MHz, DMSO-d6) δ 7.70-7.20 (dr s, 2H), 6.60 (s, 1H), 1.75 (s, 3H). |

Scheme F

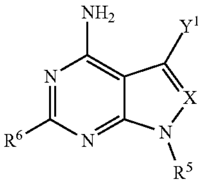

E-4

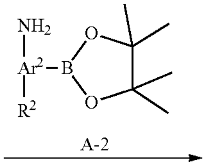

A-2

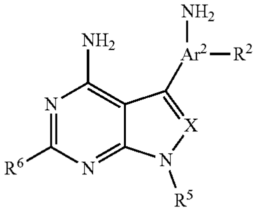

F-1

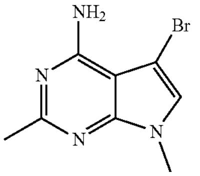

E-4.1

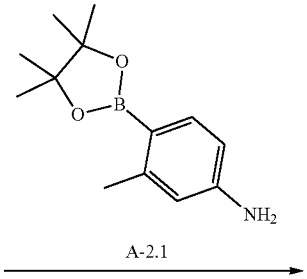

A-2.1

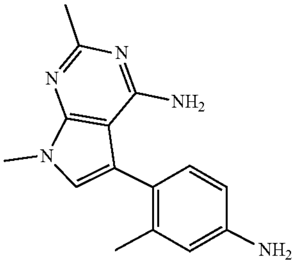

F-1.1

Compounds of Formula F-1 where $Ar^2$=phenyl, $R^2$=3-methyl, X═CH, $R^5$=methyl, $R^6$=methyl and $Y^1$═Br can be synthesized as described below for compound F-1.1:

Synthesis of 5-(4-amino-2-methylphenyl)-2,7-dimethyl-7H-pyrrolo[2,3-d]pyrimidin-4-amine (F-1.1)

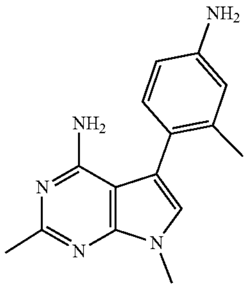

To a stirred solution of 5-bromo-2,7-dimethyl-7H-pyrrolo[2,3-d]pyrimidin-4-amine (E-4.1, 200 mg, 0.830 mmol) and 3-methyl-4-(4,4,5,5-tetramethyl-1,3,2-dioxaborolan-2-yl)aniline (A-2.1, 270 mg, 1.16 mmol) in 2-methyltetrahydrofuran (3.0 mL) was added saturated aqueous sodium bicarbonate (2.00 mL, 1.65 mmol). The mixture was purged with argon for 10 min. Palladium(II) acetate (6.0 mg, 0.027 mmol) was added, followed by di(1-adamantyl)-n-butylphosphine (cataCXium® A) (18.0 mg, 0.0502 mmol), and the mixture was purged with argon for 10 min. The resulting reaction mixture was heated at 100° C. in a sealed tube for 12 h. After this time, the mixture was allowed to cool to room temperature, passed through a bed of diatomaceous earth, and washed with methyl tert-butyl ether (2×5 mL). The filtrate was washed with water (5 mL) and brine (5 mL). The organic layer was separated, dried over sodium sulfate, and concentrated under reduced pressure. The crude product was purified by column chromatography (silica gel, 2% methanol/methylene chloride) to afford 5-(4-amino-2-methylphenyl)-2,7-dimethyl-7H-pyrrolo[2,3-d]pyrimidin-4-amine (F-1.1, 150 mg, yield: 68%) as a brown solid: ESI (m/z) 268 $[C_{15}H_{17}N_5+H]^+$.

The compounds of formula F-1 (Table F) can be synthesized according to the procedures described for compound F-1.1:

TABLE F

| Compounds F: | | | |
|---|---|---|---|
| Compound | Name | Structure | MS |
| F-1.1 | 5-(4-amino-2-methylphenyl)-2,7-dimethyl-7H-pyrrolo[2,3-d]pyrimidin-4-amine | 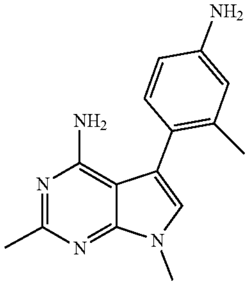 | ESI (m/z) 268 $[C_{15}H_{17}N_5 + H]^+$ |
| F-1.2 | 5-(4-amino-2-methylphenyl)-7-methyl-7H-pyrrolo[2,3-d]pyrimidin-4-amine | 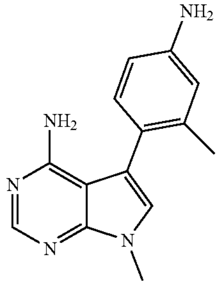 [SMILES: Cc1cc(N)ccc1-c1cn(C)c2ncnc(N)c12] | ESI (m/z) 254 $[C_{14}H_{15}N_5 + H]^+$ |
| F-1.3 | 5-(4-aminophenyl)-7-methyl-7H-pyrrolo[2,3-d]pyrimidin-4-amine | 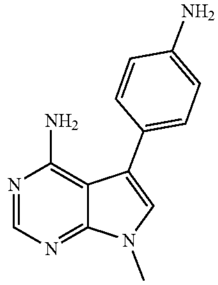 [SMILES: Cn1cc(-c2ccc(N)cc2)c2c(N)ncnc21] | ESI (m/z) 240 $[C_{13}H_{13}N_5 + H]^+$ |

TABLE F-continued

| Compounds F: | | | |
|---|---|---|---|
| Compound | Name | Structure | MS |
| F-1.4 | 5-(4-amino-2-methoxyphenyl)-2,7-dimethyl-7H-pyrrolo[2,3-d]pyrimidin-4-amine | 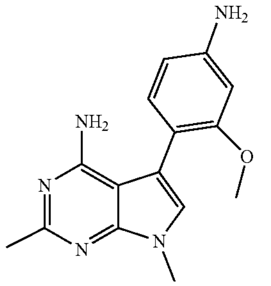 [SMILES: COc1cc(N)ccc1-c1cn(C)c2nc(C)nc(N)c12] | ESI (m/z) 284 [$C_{15}H_{17}N_5O$ + H]$^+$ |
| F-1.5 | 5-(4-aminophenyl)-2,7-dimethyl-7H-pyrrolo[2,3-d]pyrimidin-4-amine | 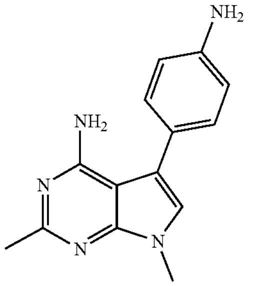 [SMILES: Cc1nc(N)c2c(-c3ccc(N)cc3)cn(C)c2n1] | ESI (m/z) 254 [$C_{14}H_{15}N_5$ + H]$^+$ |
| F-1.6 | 5-(4-amino-2-methylphenyl)-7-methyl-2-(trifluoromethyl)-7H-pyrrolo[2,3-d]pyrimidin-4-amine | 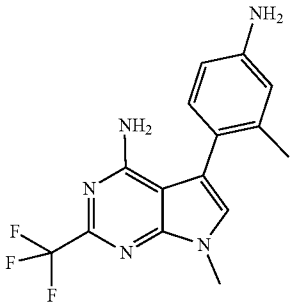 | ESI (m/z) 272 [$C_{14}H_{14}FN_5$ + H]$^+$ |
| F-1.7 | 5-(4-amino-3-fluoro-2-methylphenyl)-7-methyl-7H-pyrrolo[2,3-d]pyrimidin-4-amine | 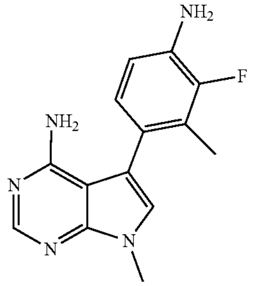 [SMILES: Cc1c(-c2cn(C)c3ncnc(N)c23)ccc(N)c1F] | ESI (m/z) 272 [$C_{14}H_{14}FN_5$ + H]$^+$ |
| F-1.8 | 5-(4-amino-2-methylphenyl)-2-ethyl-7-methyl-7H-pyrrolo[2,3-d]pyrimidin-4-amine | 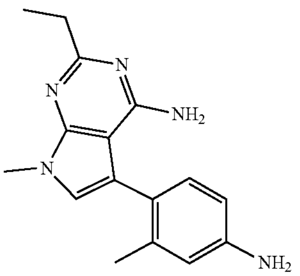 [SMILES: CCc1nc(N)c2c(-c3ccc(N)cc3C)cn(C)c2n1] | ESI (m/z) 282 [C16H19N5 + H]$^+$ |

TABLE F-continued

| Compounds F: | | | |
|---|---|---|---|
| Compound | Name | Structure | MS |
| F-1.9 | 5-(4-amino-2-fluorophenyl)-2,7-dimethyl-7H-pyrrolo[2,3-d]pyrimidin-4-amine | 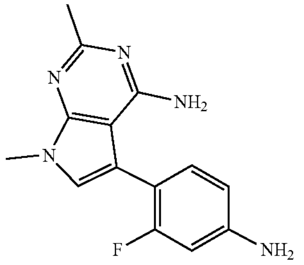 [SMILES: Cc1nc(N)c2c(-c3ccc(N)cc3F)cn(C)c2n1] | ESI (m/z) 272 [C14H14FN5 + H]$^+$ |
| F-1.10 | 5-(4-amino-3-fluorophenyl)-2,7-dimethyl-7H-pyrrolo[2,3-d]pyrimidin-4-amine | 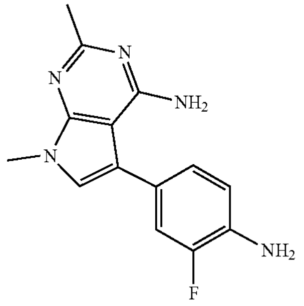 [SMILES: Cc1nc(N)c2c(-c3ccc(N)c(F)c3)cn(C)c2n1] | ESI (m/z) 272 [C14H14FN5 + H]$^+$ |
| F-1.11 | 5-(4-amino-2-chlorophenyl)-2,7-dimethyl-7H-pyrrolo[2,3-d]pyrimidin-4-amine | 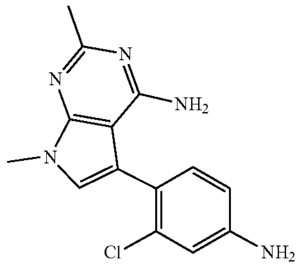 | ESI (m/z) 288 [C14H14ClN5 + H]$^+$ |
| F-1.12 | 5-(4-amino-2-methoxyphenyl)-7-methyl-7H-pyrrolo[2,3-d]pyrimidin-4-amine | 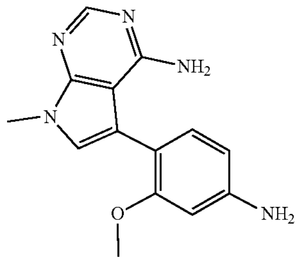 [SMILES: COc1cc(N)ccc1-c1cn(C)c2ncnc(N)c12] | ESI (m/z) 270 [C14H15N5O + H]$^+$ |
| F-1.13 | 5-(4-amino-2-methoxyphenyl)-2,7-dimethyl-7H-pyrrolo[2,3-d]pyrimidin-4-amine | 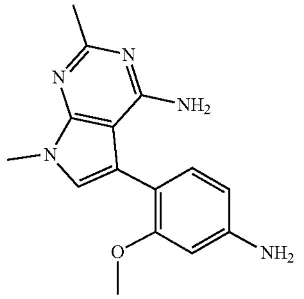 [SMILES: COc1cc(N)ccc1-c1cn(C)c2nc(C)nc(N)c12] | ESI (m/z) 284 [C15H17N5O + H]$^+$ |

TABLE F-continued

| Compounds F: | | | |
|---|---|---|---|
| Compound | Name | Structure | MS |
| F-1.14 | 5-(4-amino-2,3-difluorophenyl)-2,7-dimethyl-7H-pyrrolo[2,3-d]pyrimidin-4-amine | 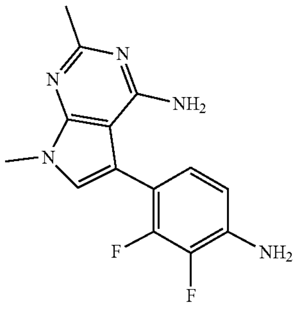 [SMILES: Cc1nc(N)c2c(-c3ccc(N)c(F)c3F)cn(C)c2n1] | ESI (m/z) 290 [C14H13F2N5 + H]$^+$ |

Scheme G

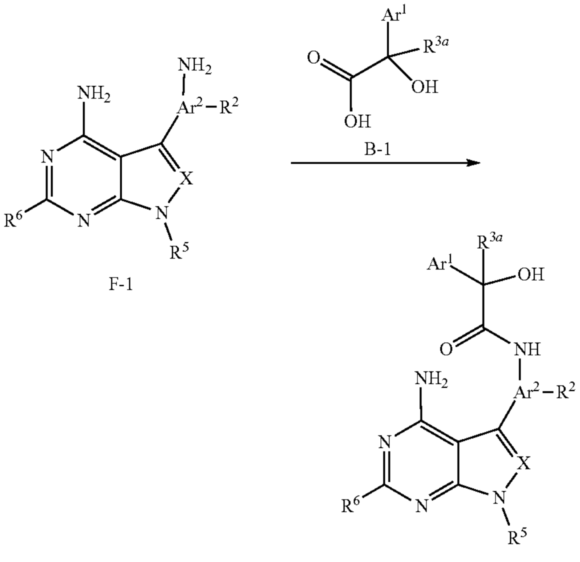

F-1

B-1

I

Compounds of Formula I can be synthesized according to the procedures for the synthesis of compound of Formula I.1 wherein X═CH, $R^5$=methyl, $R^6$=methyl, $Ar^2$=phenyl, $R^2$=3-methyl, $R^{3a}$═H, $Ar^1$=phenyl-$R^1$ and $R^1$=3—F.

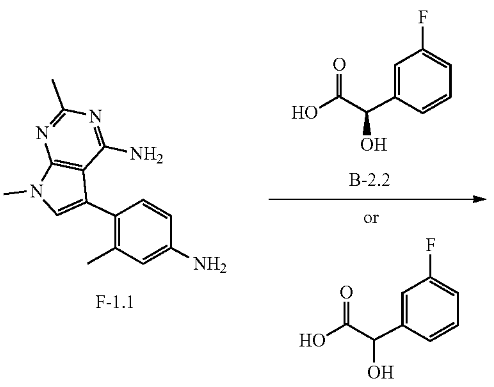

F-1.1

B-2.2 or

B-1.2

-continued

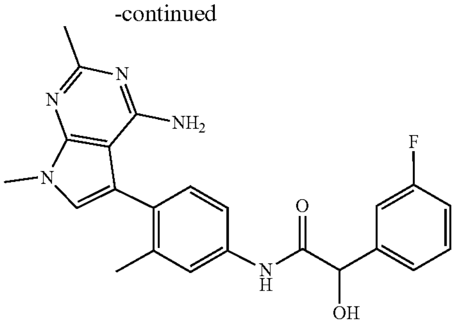

I.1

The compounds of formula I (Table 1) can be synthesized according to the procedures described for compound I.1:

Synthesis of N-(4-(4-amino-2,7-dimethyl-7H-pyrrolo[2,3-d]pyrimidin-5-yl)-3-methylphenyl)-2-(3-fluorophenyl)-2-hydroxyacetamide (I.1: Example 1 and Example 2)

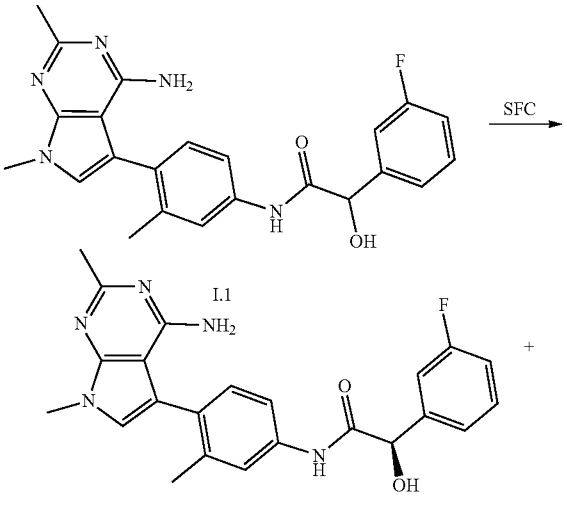

I.1

+

Example 1

-continued

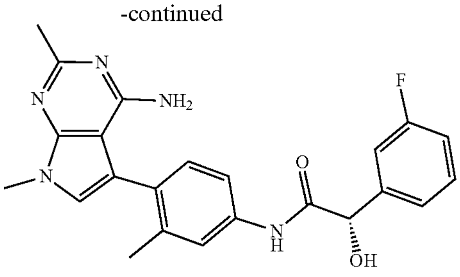

Example 2

To a solution of 5-(4-amino-2-methylphenyl)-2,7-dimethyl-7H-pyrrolo[2,3-d]pyrimidin-4-amine (F-1.1, 150 mg, 0.56 mmol) and 2-(3-fluorophenyl)-2-hydroxyacetic acid (B-1.2, 115 mg, 0.676 mmol) in tetrahydrofuran (1.50 mL) were added N,N-diisopropylethylamine (362 mg, 2.80 mmol) followed by 1-[bis(dimethylamino)methylene]-1H-1,2,3-triazolo[4,5-b]pyridinium 3-oxid hexafluorophosphate (HATU) (320 mg, 0.84 mmol) at 0° C. The reaction mixture was allowed to warm to room temperature and stirred for 12 h. After this time, the reaction mixture was diluted with methylene chloride (6.0 mL) and washed with water (4×4 mL) and brine (4 mL). The organic layer was separated, dried over anhydrous sodium sulfate, and concentrated under reduced pressure. The crude product was purified by column chromatography (silica gel, 4% methanol/methylene chloride) to afford N-(4-(4-amino-2,7-dimethyl-7H-pyrrolo[2,3-d]pyrimidin-5-yl)-3-methylphenyl)-2-(3-fluorophenyl)-2-hydroxyacetamide (1.1, 140 mg, yield: 60%) as a mixture of enantiomers as a pale brown solid: ESI (m/z) 420 $[C_{23}H_{22}FN_5O_2+H]^+$.

The mixture of enantiomers was purified by chiral supercritical fluid chromatography (SFC) (Chiralcel® OX—H column, 30% methanol in $CO_2$, 40° C. temperature) to afford:

Isomer 1 (Example 1) (60 mg) as a light yellow solid: $^1$H NM/1R (400 MHz, DMSO-$d_6$): δ 9.95 (s, 1H), 7.66 (s, 1H), 7.59 (d, J=8.4 Hz, 1H), 7.41-7.33 (m, 3H), 7.14 (d, J=8.4 Hz, 2H), 7.01 (s, 1H), 6.57 (d, J=4.8 Hz, 1H), 5.54 (br s, 2H), 5.15 (d, J=4.8 Hz, 1H), 3.68 (s, 3H), 2.39 (s, 3H), 2.14 (s, 3H); ESI (m/z): 420 $[C_{23}H_{22}FN_5O_2+H]^+$; HPLC (Method A) 94.6% (AUC), $t_R$=6.52 min; Chiral SFC (Chiralcel OX—H, Method A) >99% (AUC), $t_R$=5.26 min.

Isomer 2 (Example 2) (48 mg) as a light yellow solid: $^1$H NMR (400 MHz, DMSO-$d_6$): δ 9.96 (s, 1H), 7.66 (s, 1H), 7.59 (d, J=8.4 Hz, 1H), 7.43-7.33 (m, 3H), 7.14 (d, J=8.0 Hz, 2H), 7.02 (s, 1H), 6.58 (d, J=4.8 Hz, 1H), 5.54 (br s, 2H), 5.15 (d, J=4.4 Hz, 1H), 3.68 (s, 3H), 2.39 (s, 3H), 2.14 (s, 3H); ESI (m/z): 420 $[C_{23}H_{22}FN_5O_2+H]^+$; HPLC (Method A) 98.10% (AUC), $t_R$=6.51 min; Chiral SFC (Chiralcel OX—H, Method A) 95.6% (AUC), $t_R$=7.30 min.

Scheme H

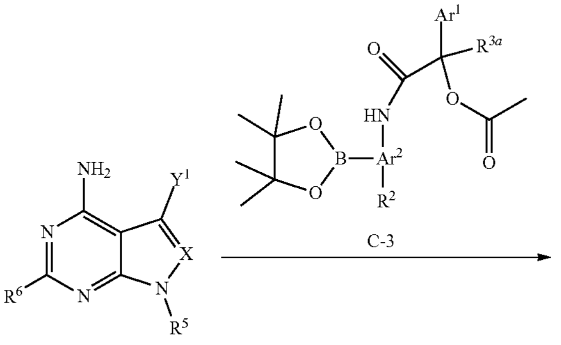

E-3

C-3

-continued

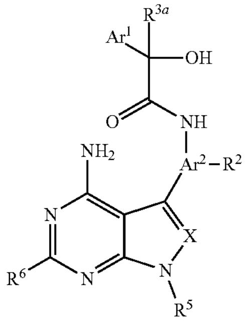

I

Compounds of Formula I can be synthesized according to the procedures for the synthesis of compound of Formula I.2 wherein $Y^1$=Br, X=CH, $R^5$=methyl, $R^6$=H, $Ar^2$=phenyl, $R^2$=3-F, $R^{3a}$=H, $Ar^1$=phenyl-$R^1$ and $R^1$=3—F.

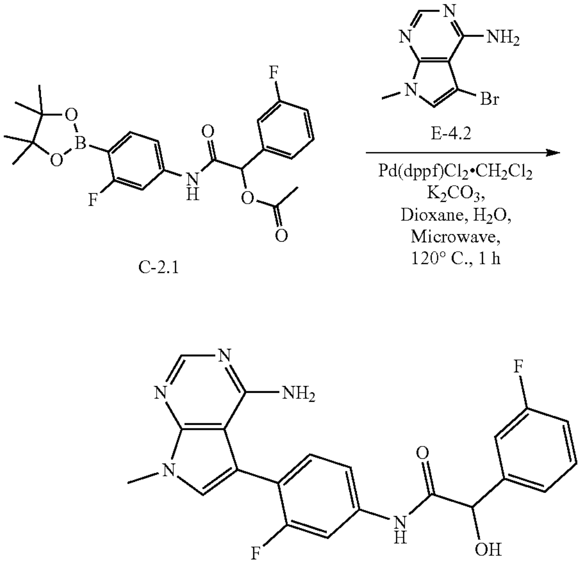

E-4.2

C-2.1

I.2

Synthesis of N-(4-(4-amino-7-methyl-7H-pyrrolo[2,3-d]pyrimidin-5-yl)-3-fluorophenyl)-2-(3-fluorophenyl)-2-hydroxyacetamide (1.2: Racemate, Example 3 and Example 4)

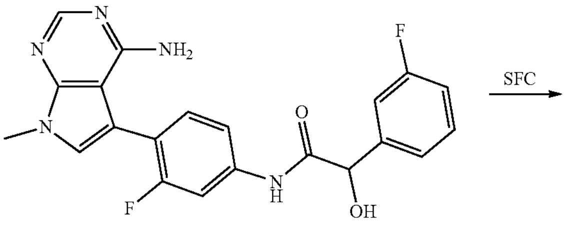

I.2

-continued

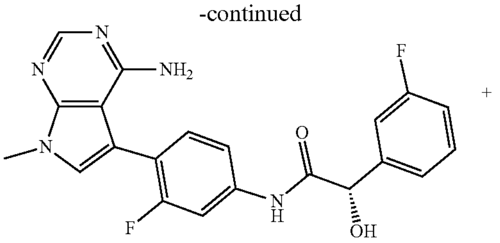

Example 3

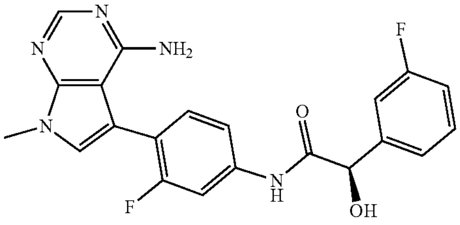

Example 4

To a stirred solution of 5-bromo-7-methyl-7H-pyrrolo[2,3-d]pyrimidin-4-amine (E-4.2, 0.500 g, 2.20 mmol) and 2-((3-fluoro-4-(4,4,5,5-tetramethyl-1,3,2-dioxaborolan-2-yl)phenyl)amino)-1-(3-fluorophenyl)-2-oxoethyl acetate (C-3.1, 1.14 g, 2.64 mmol) in a mixture of 1,4-dioxane and water (3:1, 20 mL) was purged with argon for 5 min. Potassium carbonate (0.6 g, 4.40 mmol) was added, followed by 1,1-bis(diphenylphosphino)ferrocene-palladium (II)dichloride dichloromethane complex (90 mg, 0.11 mmol), and the mixture was purged with argon for 10 min. The resulting reaction mixture was heated at 120° C. in a microwave for 1 h. After this time, the mixture was allowed to cool to room temperature, passed through a bed of diatomaceous earth, and washed with ethyl acetate (2×20 mL). The filtrate was washed with water (10 mL) and brine (10 mL). The organic layer was dried over anhydrous sodium sulfate and concentrated under reduced pressure. The crude product was purified by reversed phase column chromatography (C18, 40% acetonitrile/water) to afford N-(4-(4-amino-7-methyl-7H-pyrrolo[2,3-d]pyrimidin-5-yl)-3-fluorophenyl)-2-(3-fluorophenyl)-2-hydroxyacetamide (1.2, 200 mg, yield: 18%) as a brown solid: ESI (m/z) 410 $[C_{21}H_{17}F_2N_5O+H]^+$.

The mixture of enantiomers was purified by chiral supercritical fluid chromatography (SFC) (Chiralcel® OX—H column, 30% methanol in $CO_2$, 40° C. temperature) to afford:

Isomer 1 (Example 3 as a light yellow solid: $^1H$ NMR (400 MHz, DMSO-$d_6$) δ 10.31 (s, 1H), 8.13 (s, 1H), 7.83-7.79 (d, J=12.4 Hz, 1H), 7.63-7.61 (d, J=8 Hz, 1H), 7.44-7.27 (m, 5H), 7.16-7.12 (m, 1H), 6.70-6.69 (d, J=4.4 Hz, 1H), 6.00 (br s, 2H), 5.20-5.19 (d, J=4.4 Hz, 1H), 3.73 (s, 3H); ESI (m/z) 410 $[C_{21}H_{17}F_2N_5O+H]^+$; HPLC (Method B) 96.7% (AUC), $t_R$=7.16 min; Chiral SFC (Chiralpak IA, Method D) 98.9% (AUC), $t_R$=1.83 min.

Isomer 2 (Example 4) as a light yellow solid: $^1H$ NMR (400 MHz, DMSO-$d_6$) δ 10.31 (s, 1H), 8.13 (s, 1H), 7.83-7.79 (d, J=12.4 Hz, 1H), 7.63-7.61 (d, J=8 Hz, 1H), 7.44-7.27 (m, 5H), 7.16-7.12 (m, 1H), 6.70-6.69 (d, J=4.4 Hz, 1H), 6.00 (br s, 2H), 5.20-5.19 (d, J=4.4 Hz, 1H), 3.73 (s, 3H); ESI (m/z) 410 $[C_{21}H_{17}F_2N_5O+H]^+$; HPLC (Method B) 96.5% (AUC), $t_R$=7.16 min; Chiral SFC (Chiralpak IA, Method D) 97.1% (AUC), $t_R$=2.57 min.

Scheme I

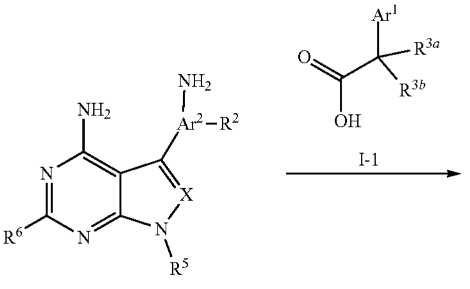

F-1

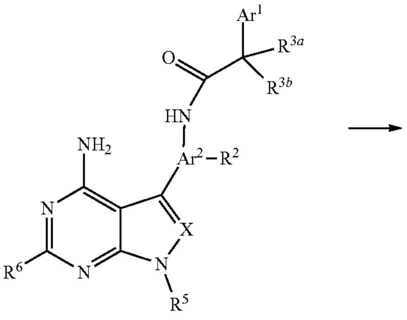

I-2

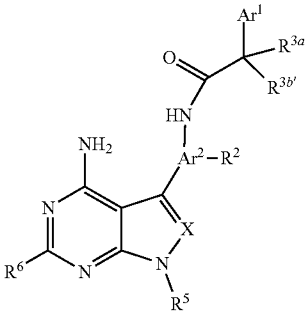

I-2

Compounds of Formula I can be synthesized according to the procedures for the synthesis of compound of Formula I-2 or I-3, wherein $R^6$═H, X═CH, $R^5$=methyl, $Ar^2$=phenyl, $R^2$=3—$CH_3$, $R^{3a}$═H, $R^{3b'}$═$NH_2$, $Ar^1$=phenyl:

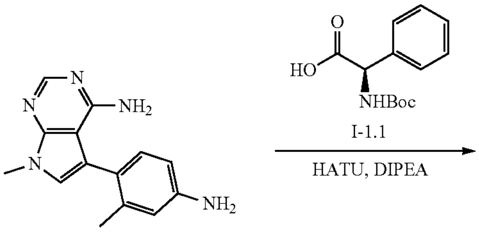

F-1.2

-continued

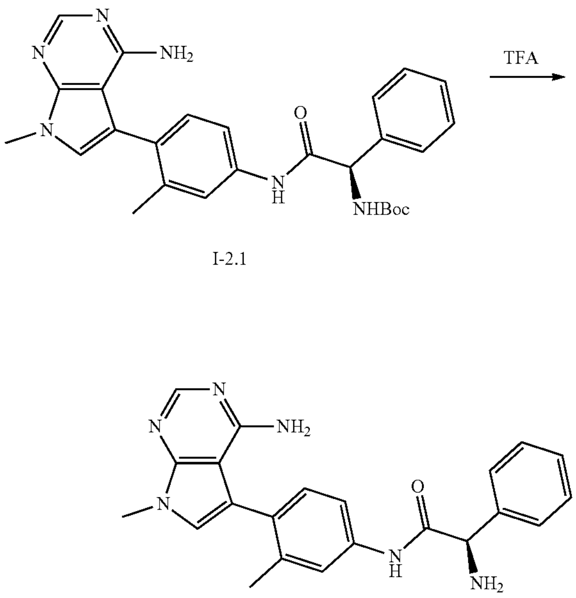

I-2.1

I-3.1

Step-1: Synthesis of (R)-tert-butyl (2-((4-(4-amino-7-methyl-7H-pyrrolo[2,3-d]pyrimidin-5-yl)-3-methyl phenyl)amino)-2-oxo-1-phenylethyl)carbamate (I-2.1)

I-2.1

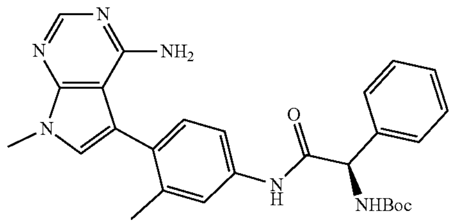

To a solution of (R)-2-((tert-butoxycarbonyl)amino)-2-phenylacetic acid (I-1.1, 0.51 g, 2.06 mmol), 5-(4-amino-2-methylphenyl)-7-methyl-7H-pyrrolo[2,3-d]pyrimidin-4-amine (F-1.2, 0.25 g, 1.37 mmol) in DMF (7.0 mL) were added DIPEA (1.20 mL, 6.88 mmol) followed by HATU (0.78 g, 2.06 mmol) at room temperature and stirred for 15 min. After this time, reaction mixture was diluted with EtOAc (20 mL), washed with water (20 mL×2) followed by brine (15 mL×2). The Organic layer was separated, dried over anhydrous $Na_2SO_4$ and volatiles were removed under reduced pressure. The crude was purified by column chromatography (silica gel, 50% EtOAc in hexanes) to afford (R)-tert-butyl (2-((4-(4-amino-7-methyl-7H-pyrrolo[2,3-d]pyrimidin-5-yl)-3-methylphenyl)amino)-2-oxo-1-phenylethyl)carbamate (I-2.1, 0.21 g, yield: 30%) as pale yellow solid; ESI (m/z) 487 $[C_{27}H_{30}N_6O_3+H]^+$.

Step-2: Synthesis of (R)-2-amino-N-(4-(4-amino-7-methyl-7H-pyrrolo[2,3-d]pyrimidin-5-yl)-3-methyl phenyl)-2-phenylacetamide (I-3.1=Example 26)

I-3.1

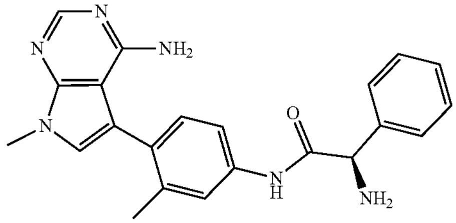

To a solution of (R)-tert-butyl (2-((4-(4-amino-7-methyl-7H-pyrrolo[2,3-d]pyrimidin-5-yl)-3-methylphenyl)amino)-2-oxo-1-phenylethyl)carbamate (I-2.1, 0.20 g, 0.41 mmol) in dichloromethane (6.0 mL) was added trifluoroacetic acid (0.62 mL, 8.23 mmol) at 0° C. and resulting reaction mixture was stirred for 15 h at room temperature. Volatiles were removed under reduced pressure to afford crude, which was diluted with dichloromethane (50 mL), adjusted pH to ~9 (by saturated $NaHCO_3$ solution). The Organic layer was separated, washed with water (20 mL×2), brine (15 mL×2), dried over anhydrous $Na_2SO_4$ and organic layer was removed under reduced pressure to afford (R)-2-amino-N-(4-(4-amino-7-methyl-7H-pyrrolo[2,3-d]pyrimidin-5-yl)-3-methylphenyl)-2-phenylacetamide (I-3.1, 0.13 g, yield: 81%) as a white solid; $^1$H-NMR (400 MHz, DMSO-$d_6$) δ 10.22 (brs, 1H), 8.11 (s, 1H), 7.58 (d, J=8.00 Hz, 2H), 7.55 (d, J=4.00 Hz, 2H), 7.54-7.48 (m, 2H), 7.36-7.32 (m, 2H), 7.29-7.27 (m, 1H), 7.27 (d, J=4.00 Hz, 1H), 7.12 (s, 1H), 5.70 (brs, 2H), 4.55 (s, 1H), 3.72 (s, 3H), 2.20 (s, 3H); ESI (m/z) 387 $[C_{22}H_{22}N_6O+H]^+$.

Scheme J

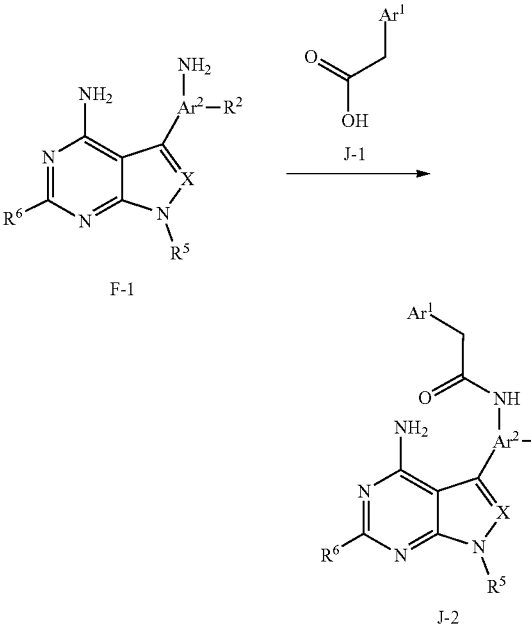

J-1

F-1

J-2

Compounds of Formula J-2 can be synthesized according to the procedures for the synthesis of compound of Formula J-2.1 wherein X═CH, $R^5$=methyl, $R^6$═H, $Ar^2$=phenyl, $R^2$=3-methyl, $Ar^1$=6-methylpyridin-2-yl:

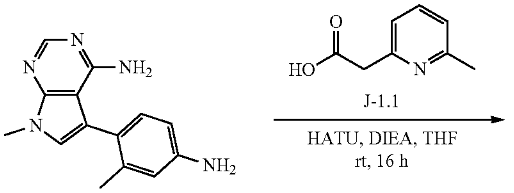

F-1.2

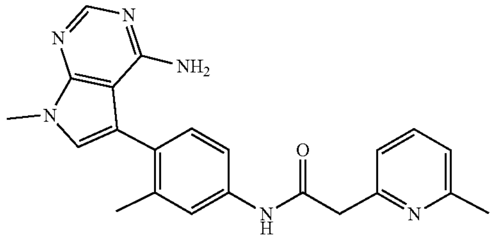

J-2.1

Synthesis of N-(4-(4-amino-7-methyl-7H-pyrrolo[2,3-d]pyrimidin-5-yl)-3-methyl phenyl)-2-(6-methylpyridin-2-yl)acetamide (J-2.1=Example 136)

To a solution of 5-(4-amino-2-methylphenyl)-7-methyl-7H-pyrrolo[2,3-d]pyrimidin-4-amine (F-1.2, 0.20 g, 0.79 mmol), 2-(6-methylpyridin-2-yl)acetic acid (J-1.1, 0.14 g, 0.94 mmol) in DMF (5 mL) were added N,N-diisopropylethylamine (0.42 mL, 2.37 mmol) followed by HATU (0.36 g, 0.94 mmol) at 0° C. The reaction mixture was allowed to warm to room temperature and stirred for 16 h. Then reaction mixture was cooled to 0° C., quenched with ice cold water (10 mL), extracted with ethyl acetate (2×20 mL). The organic layer was washed brine (10 mL), dried over anhydrous sodium sulfate and concentrated under reduced pressure. The crude product was purified by column chromatography (silica gel, 1% methanol/dichloromethane) to to afford N-(4-(4-amino-7-methyl-7H-pyrrolo[2,3-d]pyrimidin-5-yl)-3-methylphenyl)-2-(6-methylpyridin-2-yl)acetamide (J-2.1, 0.20 g, yield: 78%) as an off-white solid; $^1$H-NMR (400 MHz, DMSO-$d_6$): δ 10.31 (s, 1H), 8.13 (s, 1H), 7.66-7.61 (m, 2H), 7.53 (s, 1H), 7.21-7.14 (m, 4H), 5.74 (s, 2H), 3.81 (s, 2H), 3.74 (s, 3H), 2.46 (s, 3H), 2.16 (s, 3H); ESI (m/z) 387 $[C_{22}H_{22}N_6O+H]^+$.

Scheme K: Synthesis of phenyl (4-(4-amino-7-methyl-7H-pyrrolo[2,3-d]pyrimidin-5-yl)-3-methyl phenyl)carbamate (Example 169)

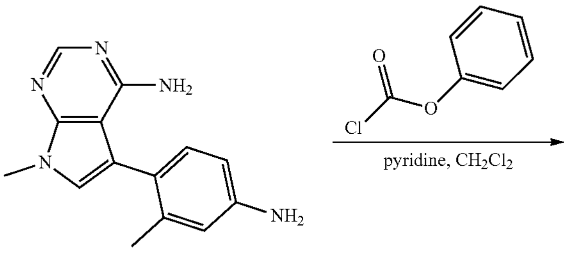

F-1.2

-continued

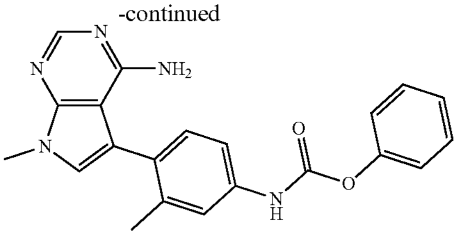

Example 169

To a solution of 5-(4-amino-2-methylphenyl)-7-methyl-7H-pyrrolo[2,3-d]pyrimidin-4-amine (F-1.2, 0.20 g, 0.79 mmol) and in $CH_2Cl_2$ (15 mL) were added pyridine (1.27 mL, 0.95 mmol), phenyl carbonochloridate (1.18 mL, 0.95 mmol) at 0° C. and resulting reaction mixture was allowed to warm to room temperature and stirred for 1 h. After this, reaction mixture was concentrated under vacuum afforded crude product, which was purified by column chromatography (silica gel, 5% MeOH in chloroform) afforded phenyl (4-(4-amino-7-methyl-7H-pyrrolo[2,3-d]pyrimidin-5-yl)-3-methylphenyl)carbamate (Example 169, 0.09 g, yield: 40%) as off white solid; $^1$H NMR (400 MHz, DMSO-$d_6$): δ 10.31 (s, 1H), 8.13 (s, 1H), 7.42-7.50 (m, 4H), 7.15-7.29 (m, 5H), 5.76 (brs, 2H), 3.74 (s, 3H), 2.17 (s, 3H); ESI (m/z) 374 $[C_{21}H_{19}N_5O_2+H]^+$.

Scheme L: Synthesis of 1-(4-(4-amino-7-methyl-7H-pyrrolo[2,3-d]pyrimidin-5-yl)-3-methyl phenyl)-3-phenylurea (Example 170)

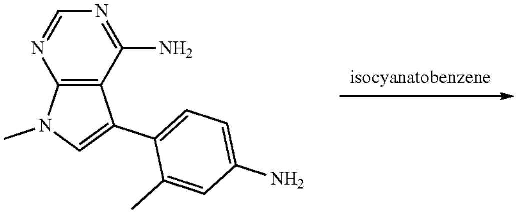

F-1.2

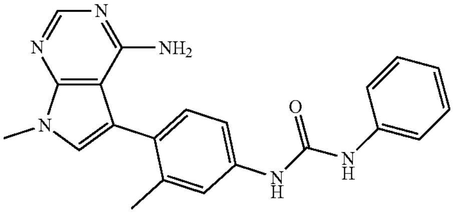

Example 170

To a solution of 5-(4-amino-2-methylphenyl)-7-methyl-7H-pyrrolo[2,3-d]pyrimidin-4-amine (F-1.2, 0.25 g, 0.99 mmol) and in THF (10 mL) was added isocyanatobenzene (1.18 mL, 1.09 mmol) at −10° C., then resulting reaction mixture was allowed to warm to room temperature and stirred for 6 h. The reaction mixture was quenched with water (20 mL), extracted with EtOAc (2×25 mL), obtained organic solvent was washed with brine solution (50 mL) and dried over anhydrous sodium sulfate, concentrated under vacuum. The crude product was purified by was purified by column chromatography (silica gel, 4% MeOH in dichloromethane) afforded 1-(4-(4-amino-7-methyl-7H-pyrrolo[2,3-d]pyrimidin-5-yl)-3-methyl phenyl)-3-phenylurea (Example 170, 0.11 g, yield: 30%) as an off white solid; $^{1}$H-NMR (400 MHz, DMSO-$d_6$): δ 8.69 (d, J=4.00 Hz, 2H), 8.13 (s, 1H), 7.44-7.47 (m, 3H), 7.36 (dd, J=8.00 Hz, 1H), 7.28 (t, J=8.00 Hz, 2H), 7.16 (s, 1H), 7.13 (s, 1H), 6.97 (t, J=8.00 Hz, 1H), 5.75 (s, 2H), 3.74 (s, 3H), 2.17 (s, 3H); ESI (m/z) 373 $[C_{21}H_{20}N_6O+H]^+$.

Scheme M: Synthesis of 3-(4-(4-amino-7-methyl-7H-pyrrolo[2,3-d]pyrimidin-5-yl)-3-methyl phenyl)-1-methyl-1-phenylurea (Example 171)

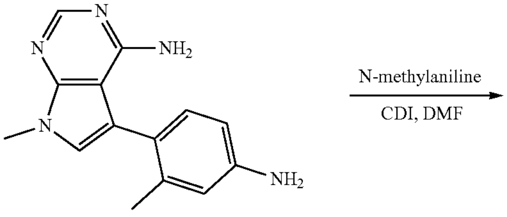

F-1.2

-continued

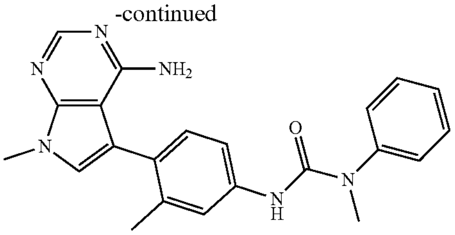

Example 171

To a solution of 5-(4-amino-2-methyl phenyl)-7-methyl-7H-pyrrolo[2,3-d]pyrimidin-4-amine (F-1.2, 0.15 g, 0.59 mmol), N-methyl aniline (0.95 g, 0.89 mmol) in DMF (10 mL) was added CDI (0.192 g, 1.18 mmol) at room temperature and stirred for 16 h at same temperature. The reaction mixture was quenched with water (10 mL), solid was precipitated out, was filtered and dried afforded crude material, which was purified by column chromatography (silica gel, 5% MeOH in chloroform) afforded 3-(4-(4-amino-7-methyl-7H-pyrrolo[2,3-d]pyrimidin-5-yl)-3-methyl phenyl)-p-methyl-1-phenylurea (Example 171, 0.10 g, yield: 43) as an off white solid; $^{1}$H NMR (400 MHz, DMSO-$d_6$): δ 8.19 (s, 1H), 8.12 (s, 1H), 7.33-7.44 (m, 6H), 7.24-7.28 (m, 1H), 7.08-7.12 (m, 2H), 5.76 (brs, 2H), 3.73 (s, 3H), 3.28 (s, 3H), 2.12 (s, 3H); ESI (m/z) 387 $[C_{22}H_{22}N_6O+H]^+$.

The compounds of formula I (Table I) can be synthesized according to the procedures described in Scheme G, Scheme H, Scheme I, Scheme J, Scheme K, Scheme L, and Scheme M:

TABLE 1

Compounds of Formula I:

| Example | Name | Compounds I | MS | Synthetic Method |
|---|---|---|---|---|
| 1 | N-(4-(4-amino-2,7-dimethyl-7H-pyrrolo[2,3-d]pyrimidin-5-yl)-3-methylphenyl)-2-(3-fluorophenyl)-2-hydroxyacetamide | 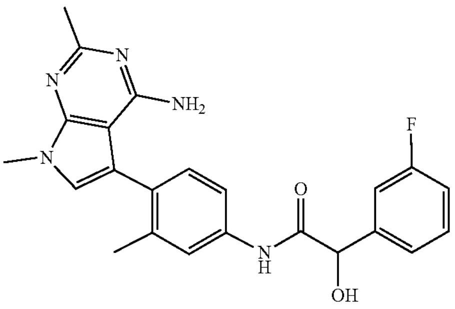 Isomer 1 | ESI (m/z) 420 $[C_{23}H_{22}FN_5O_2 + H]^+$ | Scheme G |
| 2 | N-(4-(4-amino-2,7-dimethyl-7H-pyrrolo[2,3-d]pyrimidin-5-yl)-3-methylphenyl)-2-(3-fluorophenyl)-2-hydroxyacetamide | 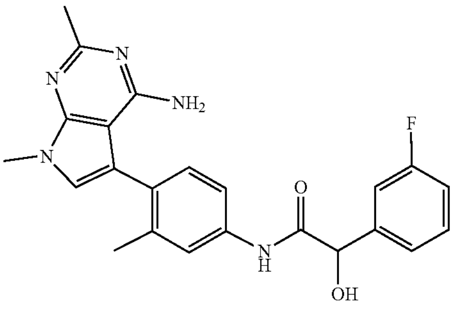 Isomer 2 | ESI (m/z): 420 $[C_{23}H_{22}FN_5O_2 + H]^+$ | Scheme G |

TABLE 1-continued

Compounds of Formula I:

| Example | Name | Compounds I | MS | Synthetic Method |
|---|---|---|---|---|
| 3 | N-(4-(4-amino-7-methyl-7H-pyrrolo[2,3-d] pyrimidin-5-yl)-3-fluorophenyl)-2-hydroxyacetamide | 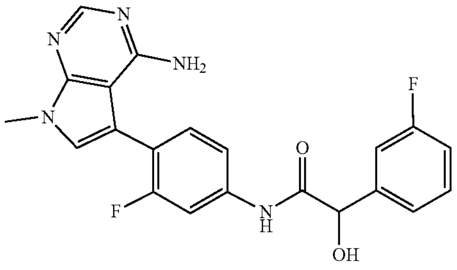<br>Isomer 1 | ESI (m/z): 410 $[C_{21}H_{17}F_2N_5O_2 + H]^+$ | Scheme H |
| 4 | N-(4-(4-amino-7-methyl-7H-pyrrolo[2,3-d] pyrimidin-5-yl)-3-fluorophenyl)-2-(3-fluorophenyl)-2-hydroxyacetamide | 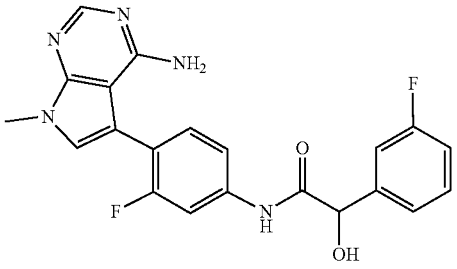<br>Isomer 2 | ESI (m/z): 410 $[C_{21}H_{17}F_2N_5O_2 + H]^+$ | Scheme H |
| 5 | N-(4-(4-amino-7-methyl-7H-pyrrolo[2,3-d]pyrimidin-5-yl)-3-methylphenyl)-2-hydroxy-2-phenylacetamide | 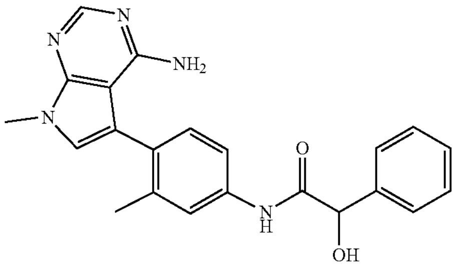<br>Racemate | ESI (m/z): 388 $[C_{22}H_{21}N_5O_2 + H]^+$ | Scheme G |
| 6 | N-(4-(4-amino-7-methyl-7H-pyrrolo[2,3-d]pyrimidin-5-yl)-3-methylphenyl)-2-hydroxy-2-phenylacetamide | 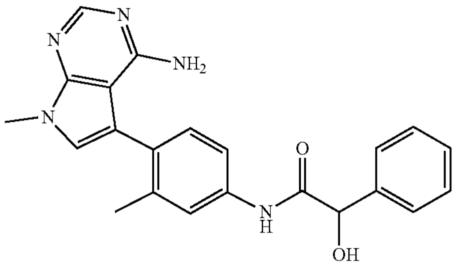<br>Isomer 1 | ESI (m/z) 388 $[C_{22}H_{21}N_5O_2 + H]^+$ | Scheme G |
| 7 | N-(4-(4-amino-7-methyl-7H-pyrrolo[2,3-d]pyrimidin-5-yl)-3-methylphenyl)-2-hydroxy-2-phenylpropanamide | 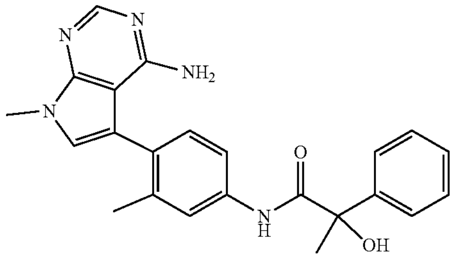 [SMILES: Cc1cc(NC(=O)C(C)(O)c2ccccc2)ccc1-c1cn(C)c2ncnc(N)c12] | ESI (m/z) 402 $[C_{23}H_{23}N_5O_2 + H]^+$ | Scheme G |

TABLE 1-continued

| Compounds of Formula I: | | | | |
|---|---|---|---|---|
| Example | Name | Compounds I | MS | Synthetic Method |
| 8 | N-(4-(4-amino-7-methyl-7H-pyrrolo[2,3-d]pyrimidin-5-yl)-3-methylphenyl)-2-methoxy-2-phenylacetamide | 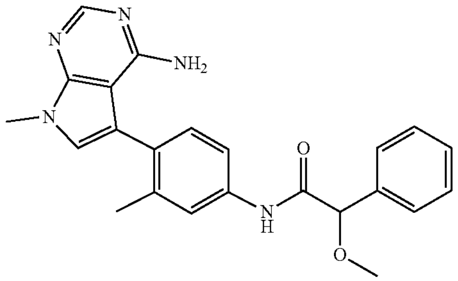 Isomer 1 | ESI (m/z) 402 $[C_{23}H_{23}N_5O_2 + H]^+$ | Scheme G |
| 9 | N-(4-(4-amino-7-methyl-7H-pyrrolo[2,3-d]pyrimidin-5-yl)-3-methylphenyl)-2-(3-fluorophenyl)-2-hydroxyacetamide | 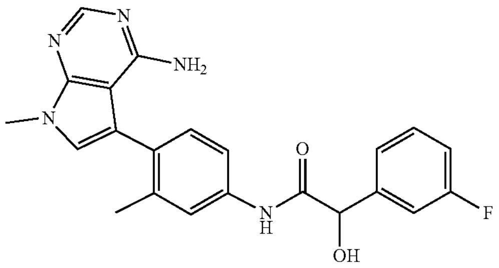 Isomer 1 | ESI (m/z) 406 $[C_{22}H_{20}FN_5O_2 + H]^+$ | Scheme G |
| 10 | N-(4-(4-amino-7-methyl-7H-pyrrolo[2,3-d]pyrimidin-5-yl)-3-methylphenyl)-2-(3-fluorophenyl)-2-hydroxyacetamide | 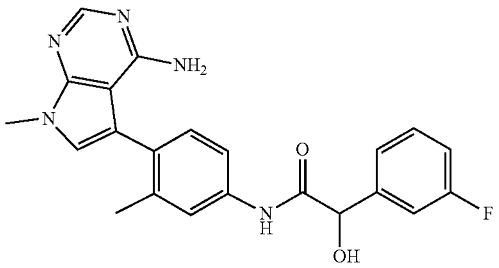 Isomer 2 | ESI (m/z) 406 $[C_{22}H_{20}FN_5O_2 + H]^+$ | Scheme G |
| 11 | N-(4-(4-amino-7-methyl-7H-pyrrolo[2,3-d]pyrimidin-5-yl)-3-methylphenyl)-2-(3-fluorophenyl)-2-hydroxyacetamide | 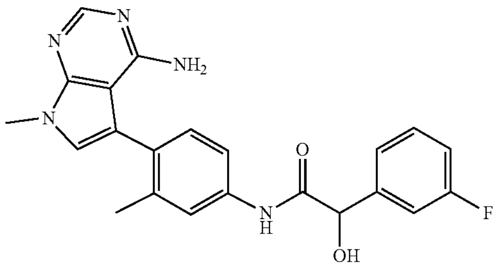 Racemate | ESI (m/z) 406 $[C_{22}H_{20}FN_5O_2 + H]^+$ | Scheme G |

TABLE 1-continued

Compounds of Formula I:

| Example | Name | Compounds I | MS | Synthetic Method |
|---|---|---|---|---|
| 12 | N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide | 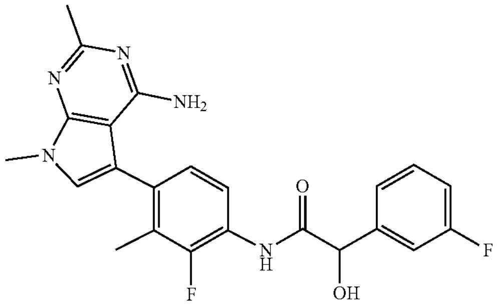 Isomer 1 | ESI (m/z) 438 [$C_{23}H_{21}F_2N_5O_2$ + H]$^+$ | Scheme G |
| 13 | N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide | 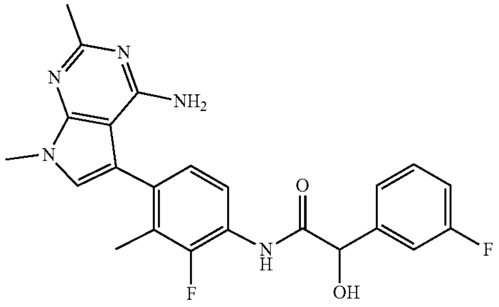 Isomer 2 | ESI (m/z) 438 [$C_{23}H_{21}F_2N_5O_2$ + H]$^+$ | Scheme G |
| 14 | N-(4-(4-amino-7-methyl-7H-pyrrolo[2,3-d]pyrimidin-5-yl)-3-chlorophenyl)-2-(3-fluorophenyl)-2-hydroxyacetamide | 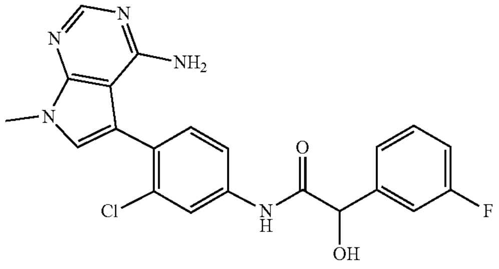 Isomer 1 | ESI (m/z) 426 [$C_{21}H_{17}ClFN_5O_2$ + H]$^+$ | Scheme H |
| 15 | N-(4-(4-amino-7-methyl-7H-pyrrolo[2,3-d]pyrimidin-5-yl)-3-chlorophenyl)-2-(3-fluorophenyl)-2-hydroxyacetamide | 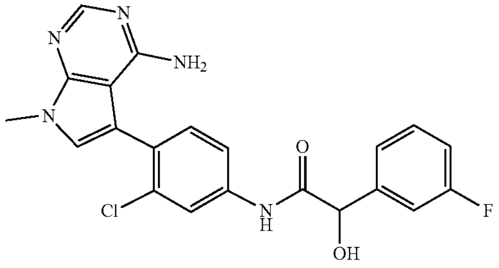 Isomer 2 | ESI (m/z) 426 [$C_{21}H_{17}ClFN_5O_2$ + H]$^+$ | Scheme H |

TABLE 1-continued

Compounds of Formula I:

| Example | Name | Compounds I | MS | Synthetic Method |
|---|---|---|---|---|
| 16 | N-(4-(4-amino-7-methyl-7H-pyrrolo[2,3-d]pyrimidin-5-yl)-3-(trifluoromethyl)phenyl)-2-(3-fluorophenyl)-2-hydroxyacetamide | 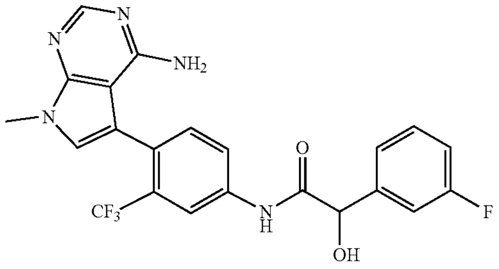 Racemic | ESI (m/z) 460 $[C_{22}H_{17}F_4N_5O_2 + H]^+$ | Scheme H |
| 17 | N-(4-(4-amino-7-methyl-7H-pyrrolo[2,3-d]pyrimidin-5-yl)-3-ethylphenyl)-2-(3-fluorophenyl)-2-hydroxyacetamide | 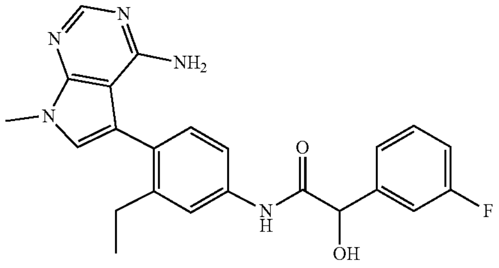 Racemic | ESI (m/z) 420 $[C_{23}H_{22}FN_5O_2 + H]^+$ | Scheme H |
| 18 | N-(4-(4-amino-7-methyl-7H-pyrrolo[2,3-d]pyrimidin-5-yl)-3-(trifluoromethoxy)phenyl)-2-(3-fluorophenyl)-2-hydroxyacetamide | 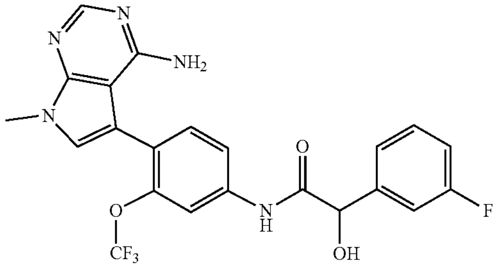 Racemic | ESI (m/z) 476 $[C_{22}H_{17}F_4N_5O_3 + H]^+$ | Scheme H |
| 19 | N-(4-(4-amino-2,7-dimethyl-7H-pyrrolo[2,3-d]pyrimidin-5-yl)-3-(trifluoromethyl)phenyl)-2-(3-fluorophenyl)-2-hydroxyacetamide | 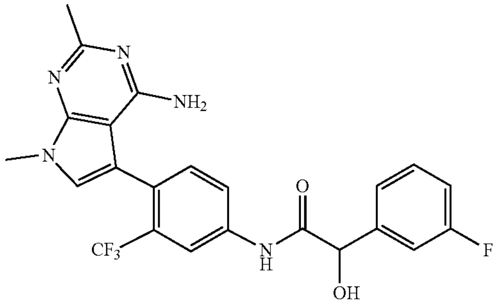 Isomer 1 | ESI (m/z) 474 $[C_{23}H_{19}F_4N_5O_2 + H]^+$ | Scheme H |

TABLE 1-continued

| Compounds of Formula I: | | | | |
|---|---|---|---|---|
| Example | Name | Compounds I | MS | Synthetic Method |
| 20 | N-(4-(4-amino-2,7-dimethyl-7H-pyrrolo[2,3-d]pyrimidin-5-yl)-3-(trifluoromethyl)phenyl)-2-(3-fluorophenyl)-2-hydroxyacetamide | 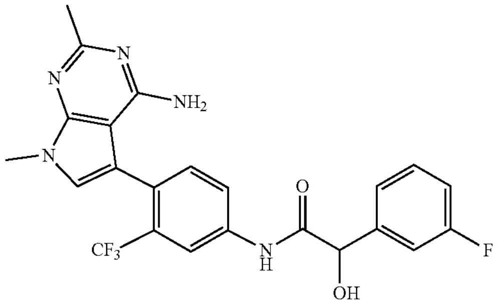 Isomer 2 | ESI (m/z) 474 $[C_{23}H_{19}F_4N_5O_2 + H]^+$ | Scheme H |
| 21 | N-(4-(4-amino-2,7-dimethyl-7H-pyrrolo[2,3-d]pyrimidin-5-yl)-3-(trifluoromethoxy)phenyl)-2-(3-fluorophenyl)-2-hydroxyacetamide | 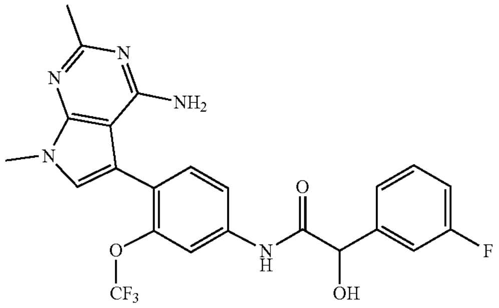 Isomer 1 | ESI (m/z) 490 $[C_{23}H_{19}F_4N_5O_3 + H]^+$ | Scheme H |
| 22 | N-(4-(4-amino-2,7-dimethyl-7H-pyrrolo[2,3-d]pyrimidin-5-yl)-3-(trifluoromethoxy)phenyl)-2-(3-fluorophenyl)-2-hydroxyacetamide | 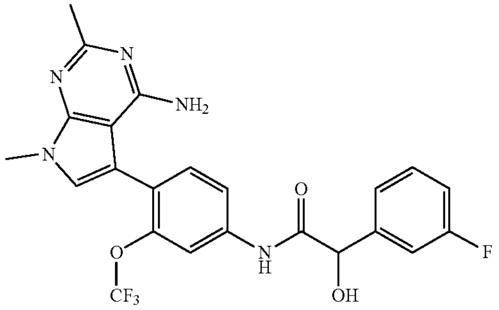 Isomer 2 | ESI (m/z) 490 $[C_{23}H_{19}F_4N_5O_3 + H]^+$ | Scheme H |
| 23 | N-(4-(4-amino-2,7-dimethyl-7H-pyrrolo[2,3-d]pyrimidin-5-yl)phenyl)-2-(3-fluorophenyl)-2-hydroxyacetamide | 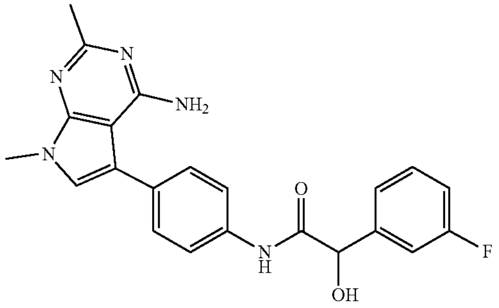 Isomer 1 | ESI (m/z) 406 $[C_{22}H_{20}FN_5O_2 + H]^+$ | Scheme G |

TABLE 1-continued

| Compounds of Formula I: | | | | |
|---|---|---|---|---|
| Example | Name | Compounds I | MS | Synthetic Method |
| 24 | N-(4-(4-amino-2,7-dimethyl-7H-pyrrolo[2,3-d]pyrimidin-5-yl)phenyl)-2-(3-fluorophenyl)-2-hydroxyacetamide | 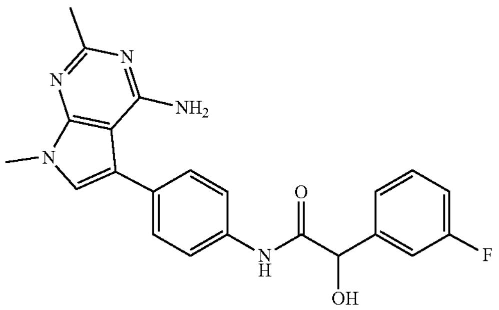 Isomer 2 | ESI (m/z) 406 $[C_{22}H_{20}FN_5O_2 + H]^+$ | Scheme G |
| 25 | N-(4-(4-amino-2-isopropyl-7-methyl-7H-pyrrolo[2,3-d]pyrimidin-5-yl)-3-methylphenyl)-2-(3-fluorophenyl)-2-hydroxyacetamide | 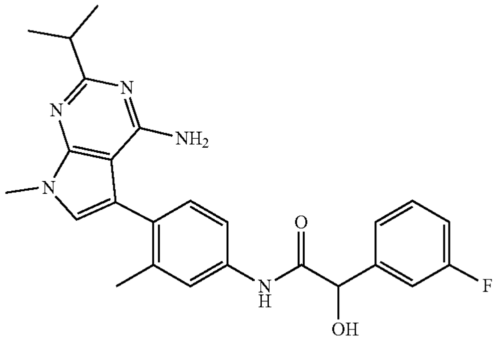 Racemic | ESI (m/z) 448 $[C_{25}H_{26}FN_5O_2 + H]^+$ | Scheme H |
| 26 | 2-amino-N-(4-(4-amino-7-methyl-7H-pyrrolo[2,3-d]pyrimidin-5-yl)-3-methylphenyl)-2-phenylacetamide | 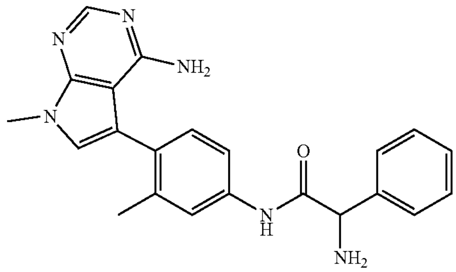 Isomer 1 | ESI (m/z) 387 $[C_{22}H_{22}N_6O + H]^+$ | Scheme I |
| 27 | 2-amino-N-(4-(4-amino-7-methyl-7H-pyrrolo[2,3-d]pyrimidin-5-yl)-3-methylphenyl)-2-phenylacetamide | 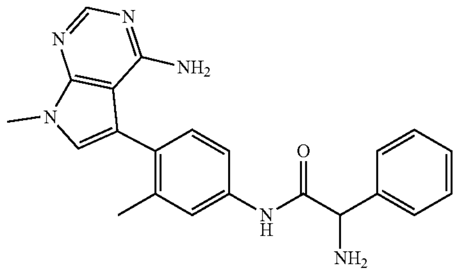 Isomer 2 | ESI (m/z) 387 $[C_{22}H_{22}N_6O + H]^+$ | Scheme I |

TABLE 1-continued

| Compounds of Formula I: | | | | |
|---|---|---|---|---|
| Example | Name | Compounds I | MS | Synthetic Method |
| 28 | N-(4-(4-amino-7-methyl-7H-pyrrolo[2,3-d]pyrimidin-5-yl)-3-methylphenyl)-2,2-difluoro-2-phenylacetamide | 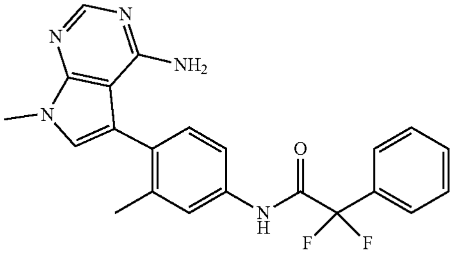 [SMILES: Cc1cc(NC(=O)C(F)(F)c2ccccc2)ccc1-c1cn(C)c2ncnc(N)c12] | ESI (m/z) 408 $[C_{22}H_{19}F_2N_5O + H]^+$ | Scheme I |
| 29 | N-(4-(4-amino-7-methyl-7H-pyrrolo[2,3-d]pyrimidin-5-yl)phenyl)-2-(3-fluorophenyl)-2-hydroxyacetamide | 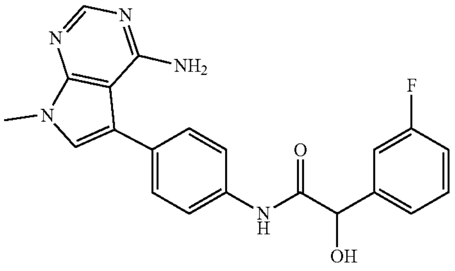 Isomer 1 | ESI (m/z) 392 $[C_{21}H_{18}FN_5O_2 + H]^+$ | Scheme G |
| 30 | N-(4-(4-amino-7-methyl-7H-pyrrolo[2,3-d]pyrimidin-5-yl)phenyl)-2-(3-fluorophenyl)-2-hydroxyacetamide | 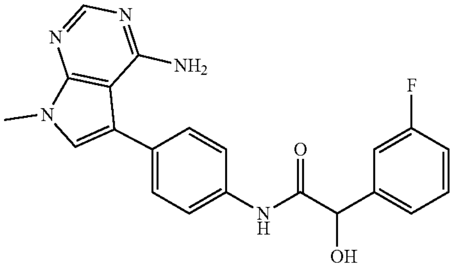 Isomer 2 | ESI (m/z) 392 $[C_{21}H_{18}FN_5O_2 + H]^+$ | Scheme G |
| 31 | N-(4-(4-amino-7-methyl-7H-pyrrolo[2,3-d]pyrimidin-5-yl)-3-methylphenyl)-2-(2-fluorophenyl)-2-hydroxyacetamide | 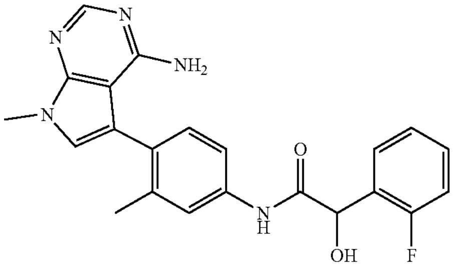 Isomer 1 | ESI (m/z) 406 $[C_{22}H_{20}FN_5O_2 + H]^+$ | Scheme G |
| 32 | N-(4-(4-amino-2,7-dimethyl-7H-pyrrolo[2,3-d]pyrimidin-5-yl)-3-methylphenyl)-2-(2-fluorophenyl)-2-hydroxyacetamide | 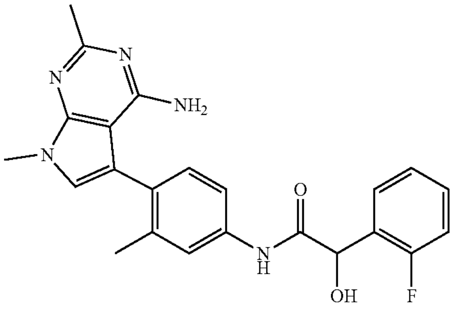 Isomer 1 | ESI (m/z) 420 $[C_{23}H_{22}FN_5O_2 + H]^+$ | Scheme G |

TABLE 1-continued

| Compounds of Formula I: | | | | |
|---|---|---|---|---|
| Example | Name | Compounds I | MS | Synthetic Method |
| 33 | N-(4-(4-amino-7-methyl-7H-pyrrolo[2,3-d]pyrimidin-5-yl)-3-methylphenyl)-2-(2-chlorophenyl)-2-hydroxyacetamide | 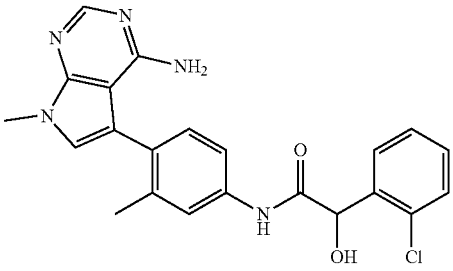 Isomer 1 | ESI (m/z) 422 $[C_{22}H_{20}ClN_5O_2 + H]^+$ | Scheme G |
| 34 | N-(4-(4-amino-2,7-dimethyl-7H-pyrrolo[2,3-d]pyrimidin-5-yl)-3-methylphenyl)-2-(2-chlorophenyl)-2-hydroxyacetamide | 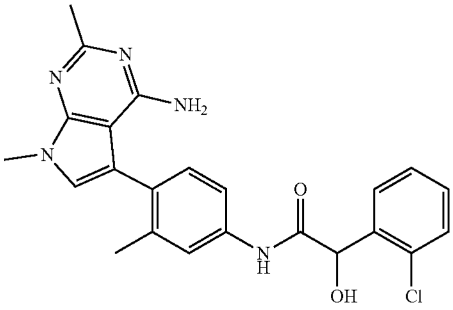 Isomer 1 | ESI (m/z) 436 $[C_{23}H_{21}ClN_5O_2 + H]^+$ | Scheme G |
| 35 | N-(4-(4-amino-7-methyl-7H-pyrrolo[2,3-d]pyrimidin-5-yl)-3-methylphenyl)-2-(3-chlorophenyl)-2-hydroxyacetamide | 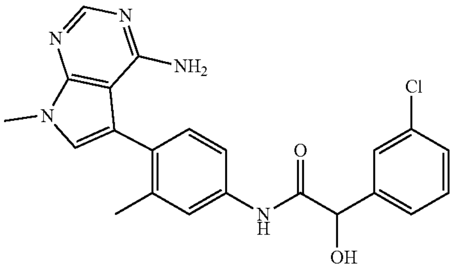 Racemate | ESI (m/z) 422 $[C_{22}H_{20}ClN_5O_2 + H]^+$ | Scheme G |
| 36 | N-(4-(4-amino-2,7-dimethyl-7H-pyrrolo[2,3-d]pyrimidin-5-yl)-3-methylphenyl)-2-(3-chlorophenyl)-2-hydroxyacetamide | 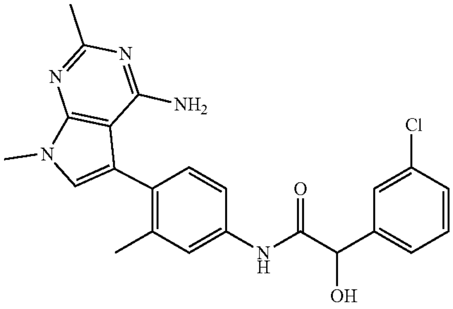 Racemate | ESI (m/z) 436 $[C_{23}H_{22}ClN_5O_2 + H]^+$ | Scheme G |

TABLE 1-continued

| Compounds of Formula I: | | | | |
|---|---|---|---|---|
| Example | Name | Compounds I | MS | Synthetic Method |
| 37 | N-(4-(4-amino-2,7-dimethyl-7H-pyrrolo[2,3-d]pyrimidin-5-yl)-3-methylphenyl)-2-(3-chlorophenyl)-2-hydroxyacetamide | 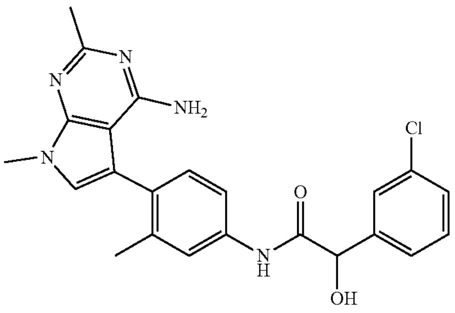 Isomer 1 | ESI (m/z) 436 $[C_{23}H_{22}ClN_5O_2 + H]^+$ | Scheme G |
| 38 | N-(4-(4-amino-2,7-dimethyl-7H-pyrrolo[2,3-d]pyrimidin-5-yl)-3-methylphenyl)-2-(3-chlorophenyl)-2-hydroxyacetamide | 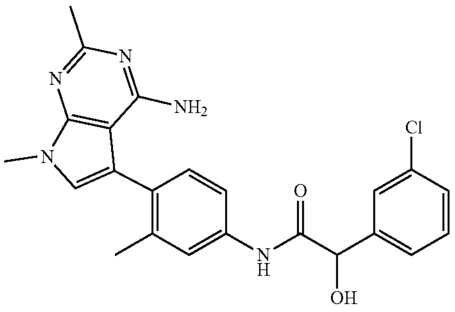 Isomer 2 | ESI (m/z) 436 $[C_{23}H_{22}ClN_5O_2 + H]^+$ | Scheme G |
| 39 | N-(4-(4-amino-7-methyl-7H-pyrrolo[2,3-d]pyrimidin-5-yl)-3-methylphenyl)-2-hydroxy-2-(o-tolyl)acetamide | 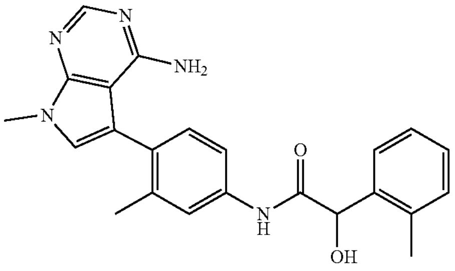 Racemate | ESI (m/z) 402 $[C_{23}H_{23}N_5O_2 + H]^+$ | Scheme G |
| 40 | N-(4-(4-amino-2,7-dimethyl-7H-pyrrolo[2,3-d]pyrimidin-5-yl)-3-methylphenyl)-2-hydroxy-2-(o-tolyl)acetamide | 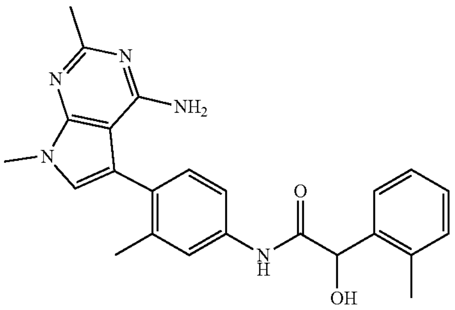 Racemate | ESI (m/z) 416 $[C_{24}H_{25}N_5O_2 + H]^+$ | Scheme G |

TABLE 1-continued

Compounds of Formula I:

| Example | Name | Compounds I | MS | Synthetic Method |
|---|---|---|---|---|
| 41 | N-(4-(4-amino-7-methyl-7H-pyrrolo[2,3-d]pyrimidin-5-yl)-3-methylphenyl)-2-hydroxy-2-(m-tolyl)acetamide | 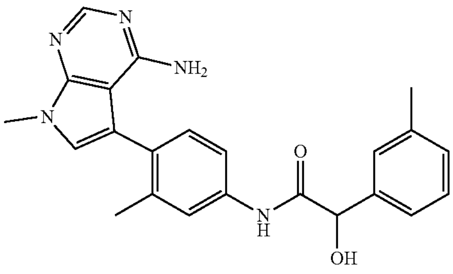 Racemate | ESI (m/z) 402 $[C_{23}H_{23}N_5O_2 + H]^+$ | Scheme G |
| 42 | N-(4-(4-amino-2,7-dimethyl-7H-pyrrolo[2,3-d]pyrimidin-5-yl)-3-methylphenyl)-2-hydroxy-2-(m-tolyl)acetamide | 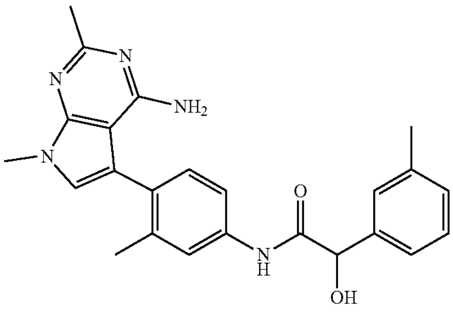 Racemate | ESI (m/z) 416 $[C_{24}H_{25}FN_5O_2 + H]^+$ | Scheme G |
| 43 | N-(4-(4-amino-2,7-dimethyl-7H-pyrrolo[2,3-d]pyrimidin-5-yl)-3-methylphenyl)-2-(3-ethylphenyl)-2-hydroxyacetamide | 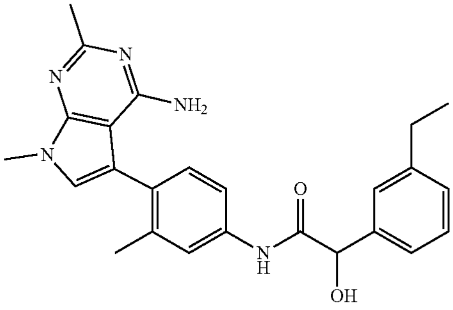 Isomer 1 | ESI (m/z) 430 $[C_{25}H_{27}N_5O_2 + H]^+$ | Scheme G |
| 44 | N-(4-(4-amino-2,7-dimethyl-7H-pyrrolo[2,3-d]pyrimidin-5-yl)-3-methylphenyl)-2-(3-ethylphenyl)-2-hydroxyacetamide | 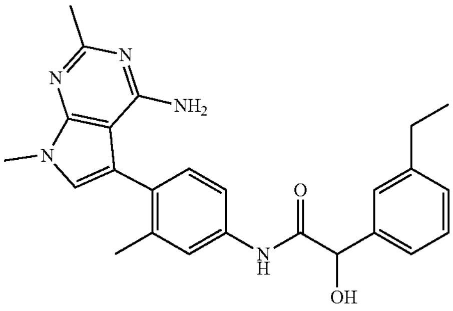 Isomer 2 | ESI (m/z) 430 $[C_{25}H_{27}N_5O_2 + H]^+$ | Scheme G |

TABLE 1-continued

| Compounds of Formula I: | | | | |
|---|---|---|---|---|
| Example | Name | Compounds I | MS | Synthetic Method |
| 45 | N-(4-(4-amino-7-methyl-7H-pyrrolo[2,3-d]pyrimidin-5-yl)-3-methylphenyl)-2-hydroxy-2-(2-(trifluoromethyl)phenyl)acetamide | 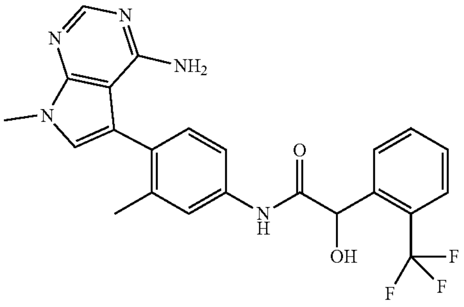 Racemate | ESI (m/z) 456 $[C_{23}H_{20}F_3N_5O_2 + H]^+$ | Scheme G |
| 46 | N-(4-(4-amino-2,7-dimethyl-7H-pyrrolo[2,3-d]pyrimidin-5-yl)-3-methylphenyl)-2-hydroxy-2-(2-(trifluoromethyl)phenyl)acetamide | 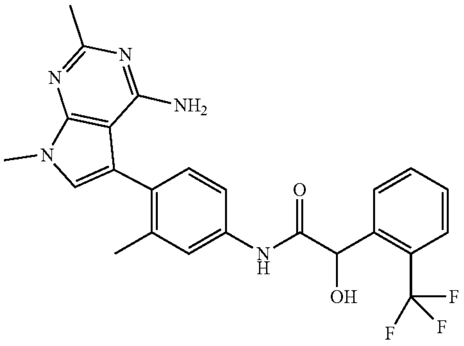 Racemate | ESI (m/z) 470 $[C_{24}H_{22}F_3N_5O_2 + H]^+$ | Scheme G |
| 47 | N-(4-(4-amino-7-methyl-7H-pyrrolo[2,3-d]pyrimidin-5-yl)-3-methylphenyl)-2-hydroxy-2-(3-(trifluoromethyl)phenyl)acetamide | 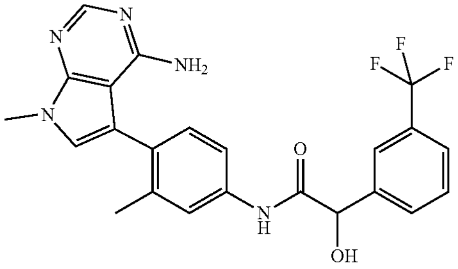 Isomer 1 | ESI (m/z) 456 $[C_{23}H_{20}F_3N_5O_2 + H]^+$ | Scheme G |
| 48 | N-(4-(4-amino-7-methyl-7H-pyrrolo[2,3-d]pyrimidin-5-yl)-3-methylphenyl)-2-hydroxy-2-(3-(trifluoromethyl)phenyl)acetamide | 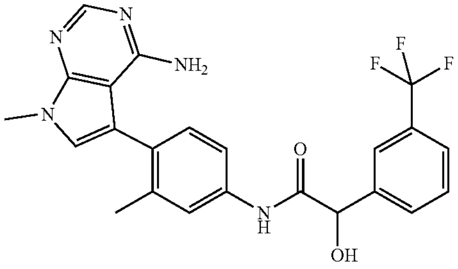 Isomer 2 | ESI (m/z) 456 $[C_{23}H_{20}F_3N_5O_2 + H]^+$ | Scheme G |

TABLE 1-continued

| Compounds of Formula I: | | | | |
|---|---|---|---|---|
| Example | Name | Compounds I | MS | Synthetic Method |
| 49 | N-(4-(4-amino-2,7-dimethyl-7H-pyrrolo[2,3-d]pyrimidin-5-yl)-3-methylphenyl)-2-hydroxy-2-(3-(trifluoromethyl)phenyl)acetamide | 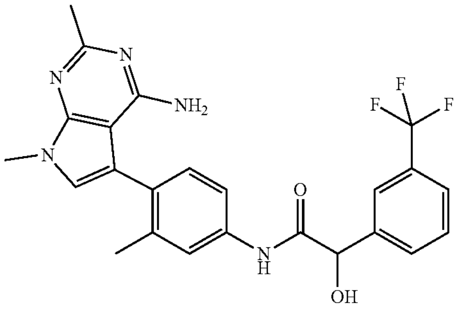 Racemate | ESI (m/z) 470 $[C_{24}H_{22}F_3N_5O_2 + H]^+$ | Scheme G |
| 50 | N-(4-(4-amino-2,7-dimethyl-7H-pyrrolo[2,3-d]pyrimidin-5-yl)-3-methylphenyl)-2-hydroxy-2-(3-(trifluoromethyl)phenyl)acetamide | 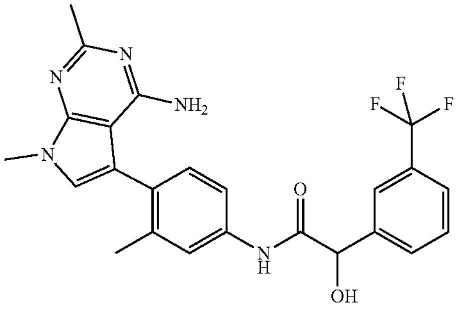 Isomer 1 | ESI (m/z) 470 $[C_{24}H_{22}F_3N_5O_2 + H]^+$ | Scheme G |
| 51 | N-(4-(4-amino-2,7-dimethyl-7H-pyrrolo[2,3-d]pyrimidin-5-yl)-3-methylphenyl)-2-hydroxy-2-(3-(trifluoromethyl)phenyl)acetamide | 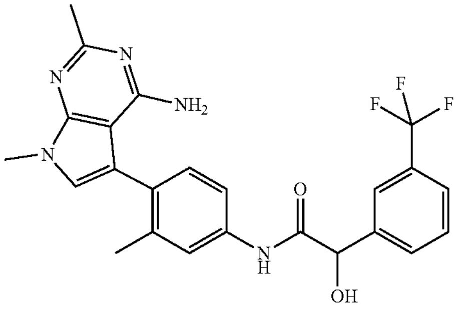 Isomer 2 | ESI (m/z) 470 $[C_{24}H_{22}F_3N_5O_2 + H]^+$ | Scheme G |
| 52 | N-(4-(4-amino-2,7-dimethyl-7H-pyrrolo[2,3-d]pyrimidin-5-yl)-3-methylphenyl)-2-(3,5-difluorophenyl)-2-hydroxyacetamide | 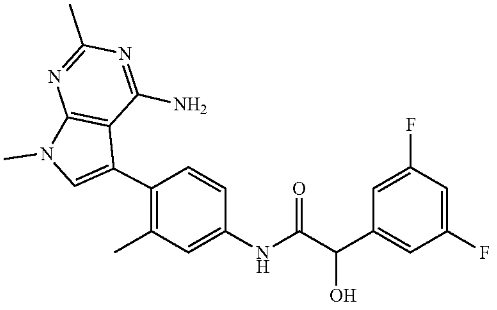 Isomer 1 | ESI (m/z) 438 $[C_{23}H_{21}F_2N_5O_2 + H]^+$ | Scheme G |

TABLE 1-continued

| Compounds of Formula I: | | | | |
|---|---|---|---|---|
| Example | Name | Compounds I | MS | Synthetic Method |
| 53 | N-(4-(4-amino-2,7-dimethyl-7H-pyrrolo[2,3-d]pyrimidin-5-yl)-3-methylphenyl)-2-(3,5-difluorophenyl)-2-hydroxyacetamide | 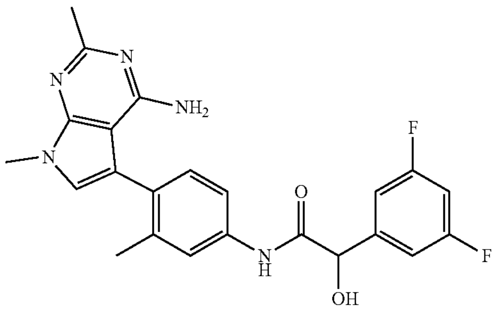 Isomer 2 | ESI (m/z) 438 $[C_{23}H_{21}F_2N_5O_2 + H]^+$ | Scheme G |
| 54 | N-(4-(4-amino-2,7-dimethyl-7H-pyrrolo[2,3-d]pyrimidin-5-yl)-3-methylphenyl)-2-(3-fluoro-5-(trifluorophenyl) phenyl)-2-hydroxyacetamide | 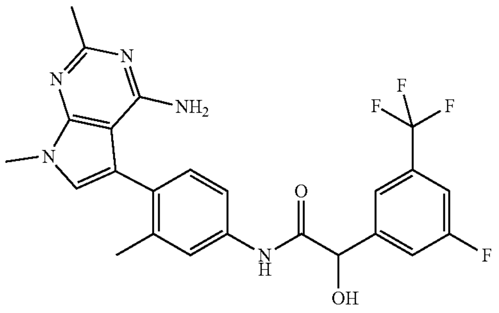 Isomer 1 | ESI (m/z) 488 $[C_{24}H_{21}F_4N_5O_2 + H]^+$ | Scheme G |
| 55 | N-(4-(4-amino-2,7-dimethyl-7H-pyrrolo[2,3-d]pyrimidin-5-yl)-3-methylphenyl)-2-(3-fluoro-5-(trifluoromethyl) phenyl)-2-hydroxyacetamide | 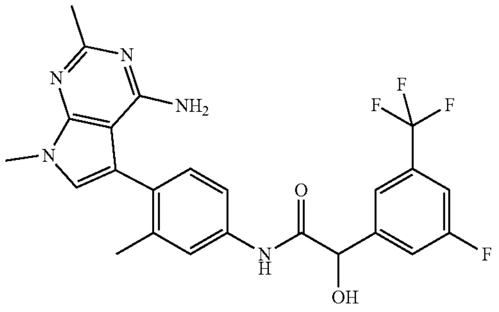 Isomer 2 | ESI (m/z) 488 $[C_{24}H_{21}F_4N_5O_2 + H]^+$ | Scheme G |
| 56 | N-(4-(4-amino-2,7-dimethyl-7H-pyrrolo[2,3-d]pyrimidin-5-yl)-3-methylphenyl)-2-(3-fluoro-5-methylphenyl)-2-hydroxyacetamide | 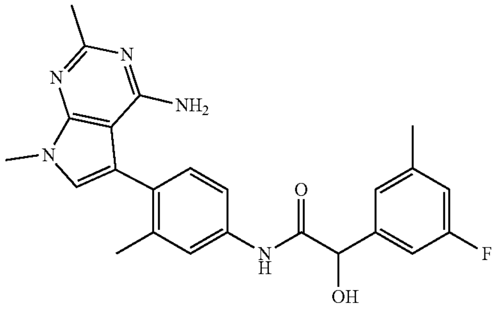 Isomer 1 | ESI (m/z) 434 $[C_{24}H_{24}FN_5O_2 + H]^+$ | Scheme G |

TABLE 1-continued

| Compounds of Formula I: | | | | |
|---|---|---|---|---|
| Example | Name | Compounds I | MS | Synthetic Method |
| 57 | N-(4-(4-amino-2,7-dimethyl-7H-pyrrolo[2,3-d]pyrimidin-5-yl)-3-methylphenyl)-2-(3-fluoro-5-methylphenyl)-2-hydroxyacetamide | 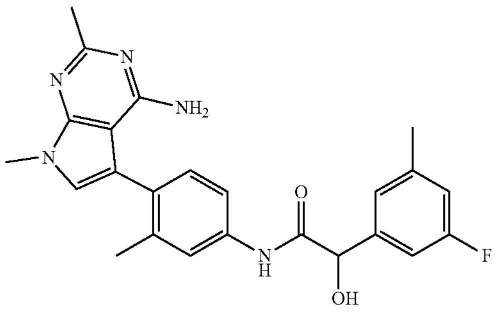 Isomer 2 | ESI (m/z) 434 $[C_{24}H_{24}FN_5O_2 + H]^+$ | Scheme G |
| 58 | N-(4-(4-amino-2,7-dimethyl-7H-pyrrolo[2,3-d]pyrimidin-5-yl)-3-methylphenyl)-2-(3-ethyl-5-fluorophenyl)-2-hydroxyacetamide | 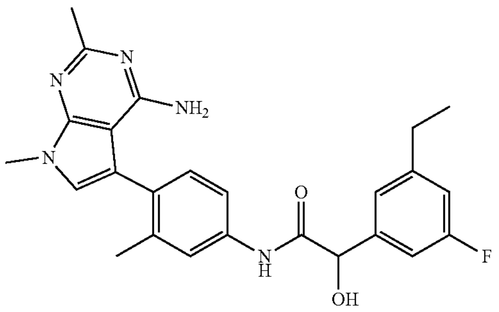 Isomer 1 | ESI (m/z) 448 $[C_{25}H_{26}FN_5O_2 + H]^+$ | Scheme G |
| 59 | N-(4-(4-amino-2,7-dimethyl-7H-pyrrolo[2,3-d]pyrimidin-5-yl)-3-methylphenyl)-2-(3-ethyl-5-fluorophenyl)-2-hydroxyacetamide | 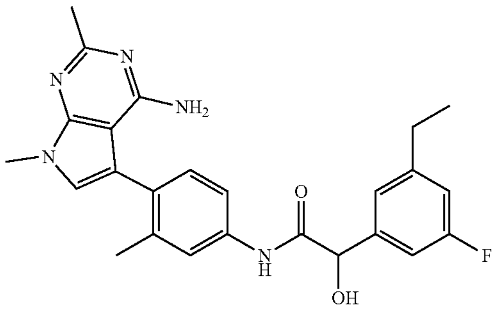 Isomer 2 | ESI (m/z) 448 $[C_{25}H_{26}FN_5O_2 + H]^+$ | Scheme G |
| 60 | N-(4-(4-amino-7-methyl-7H-pyrrolo[2,3-d]pyrimidin-5-yl)-3-methylphenyl)-2-hydroxy-2-(6-methylpyridin-2-yl)acetamide | 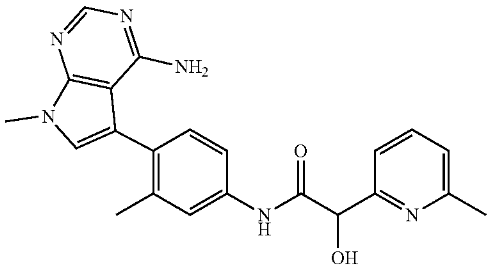 Racemate | ESI (m/z) 403 $[C_{22}H_{22}N_6O_2 + H]^+$ | Scheme G |

TABLE 1-continued

| Compounds of Formula I: | | | | |
|---|---|---|---|---|
| Example | Name | Compounds I | MS | Synthetic Method |
| 61 | N-(4-(4-amino-2,7-dimethyl-7H-pyrrolo[2,3-d]pyrimidin-5-yl)-3-methylphenyl)-2-hydroxy-2-(6-(trifluoromethyl) pyridin-2-yl)acetamide | 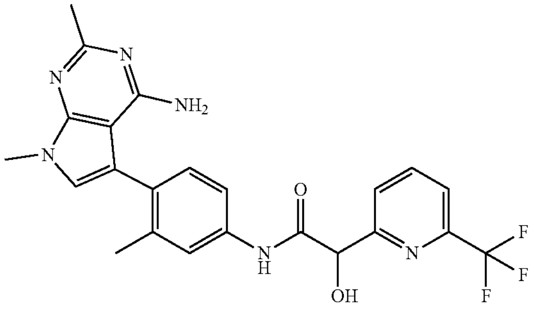 Isomer 1 | ESI (m/z) 471 $[C_{23}H_{21}F_3N_6O_2 + H]^+$ | Scheme G |
| 62 | N-(4-(4-amino-2,7-dimethyl-7H-pyrrolo[2,3-d]pyrimidin-5-yl)-3-methylphenyl)-2-hydroxy-2-(6-(trifluoromethyl) pyridin-2-yl)acetamide | 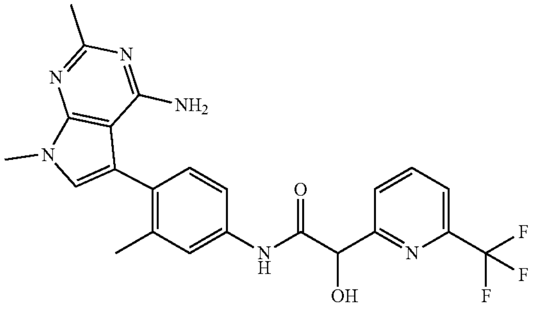 Isomer 2 | ESI (m/z) 471 $[C_{23}H_{21}F_3N_6O_2 + H]^+$ | Scheme G |
| 63 | N-(4-(4-amino-2,7-dimethyl-7H-pyrrolo[2,3-d]pyrimidin-5-yl)-3-methylphenyl)-2-(2,3-dihydrobenzofuran-7-yl)-2-hydroxyacetamide | 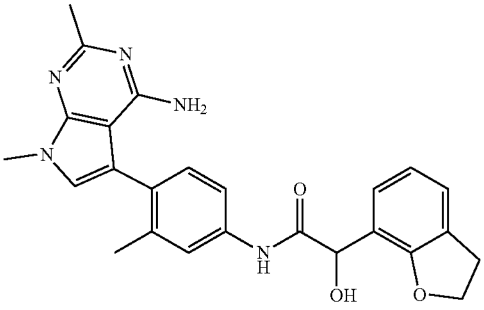 Racemate | ESI (m/z) 444 $[C_{25}H_{25}N_5O_3 + H]^+$ | Scheme G |
| 64 | N-(4-(4-amino-2,7-dimethyl-7H-pyrrolo[2,3-d]pyrimidin-5-yl)-3-methylphenyl)-2-hydroxy-2-(1-methyl-1H-indazol-7-yl)acetamide | 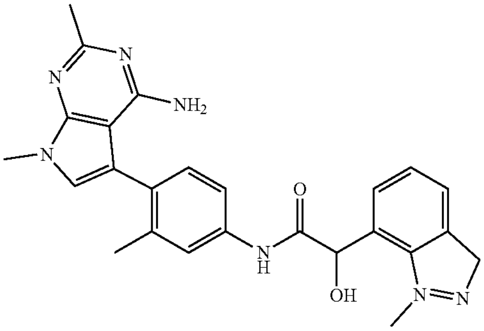 Isomer 1 | ESI (m/z) 456 $[C_{25}H_{25}N_7O_2 + H]^+$ | Scheme G |

TABLE 1-continued

| Compounds of Formula I: | | | | |
|---|---|---|---|---|
| Example | Name | Compounds I | MS | Synthetic Method |
| 65 | N-(4-(4-amino-2,7-dimethyl-7H-pyrrolo[2,3-d]pyrimidin-5-yl)-3-methylphenyl)-2-hydroxy-2-(1-methyl-1H-indazol-7-yl)acetamide | 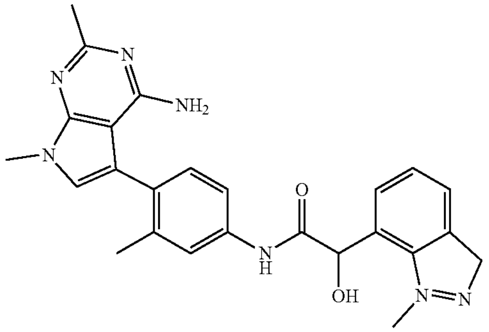 Isomer 2 | ESI (m/z) 456 [$C_{25}H_{25}N_7O_2$ + H]$^+$ | Scheme G |
| 66 | N-(4-(4-amino-7-methyl-2-(trifluoromethyl)-7H-pyrrolo[2,3-d]pyrimidin-5-yl)-3-methylphenyl)-2-(3-fluorophenyl)-2-hydroxyacetamide | 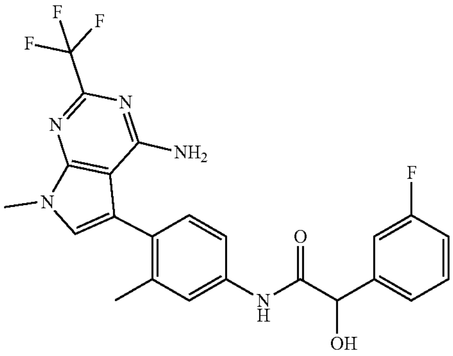 Racemate | ESI (m/z) 474 [$C_{23}H_{19}F_4N_5O_2$ + H]$^+$ | Scheme G |
| 67 | N-(4-(4-amino-2-ethyl-7-methyl-7H-pyrrolo[2,3-d]pyrimidin-5-yl)-3-methylphenyl)-2-(3-fluorophenyl)-2-hydroxyacetamide | 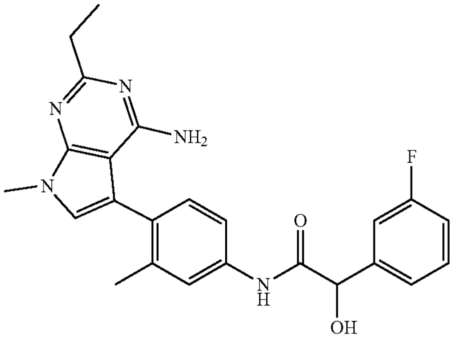 Racemate | ESI (m/z) 434 [$C_{24}H_{24}FN_5O_2$ + H]$^+$ | Scheme G |
| 68 | N-(4-(4-amino-2-2,7-dimethyl-7H-pyrrolo[2,3-d]pyrimidin-5-yl)-3-ethylphenyl)-2-(3-fluorophenyl)-2-hydroxyacetamide | 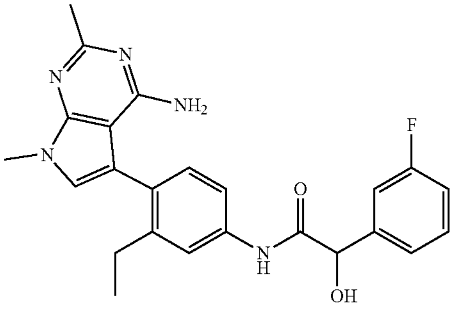 Isomer 1 | ESI (m/z) 434 [$C_{24}H_{24}FN_5O_2$ + H]$^+$ | Scheme H |

TABLE 1-continued

Compounds of Formula I:

| Example | Name | Compounds I | MS | Synthetic Method |
|---|---|---|---|---|
| 69 | N-(4-(4-amino-2,7-dimethyl-7H-pyrrolo[2,3-d]pyrimidin-5-yl)-3-ethylphenyl)-2-(3-fluorophenyl)-2-hydroxyacetamide | 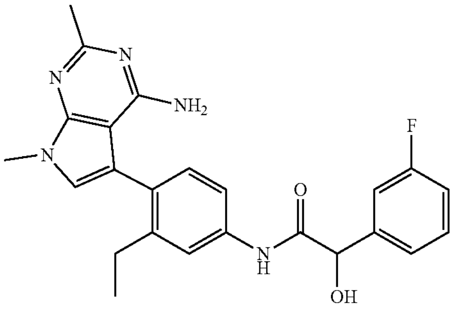<br>Isomer 2 | ESI (m/z) 434 $[C_{24}H_{24}FN_5O_2 + H]^+$ | Scheme H |
| 70 | N-(4-(4-amino-2,7-dimethyl-7H-pyrrolo[2,3-d]pyrimidin-5-yl)-3-fluorophenyl)-2-(2-chlorophenyl)-2-hydroxyacetamide | 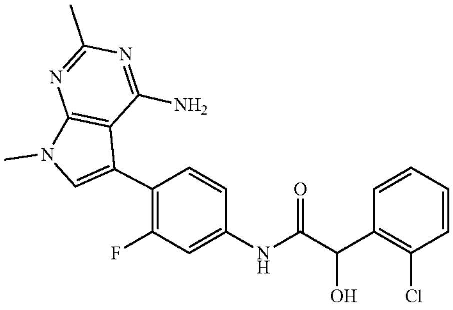<br>Isomer 1 | ESI (m/z) 440 $[C_{22}H_{19}ClFN_5O_2 + H]^+$ | Scheme G |
| 71 | N-(4-(4-amino-2,7-dimethyl-7H-pyrrolo[2,3-d]pyrimidin-5-yl)-3-fluorophenyl)-2-hydroxy-2-(o-tolyl)acetamide | 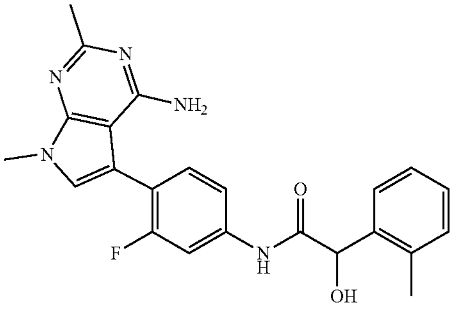<br>Isomer 1 | ESI (m/z) 420 $[C_{23}H_{22}FN_5O_2 + H]^+$ | Scheme G |
| 72 | N-(4-(4-amino-2,7-dimethyl-7H-pyrrolo[2,3-d]pyrimidin-5-yl)-3-fluorophenyl)-2-hydroxy-2-(o-tolyl)acetamide | 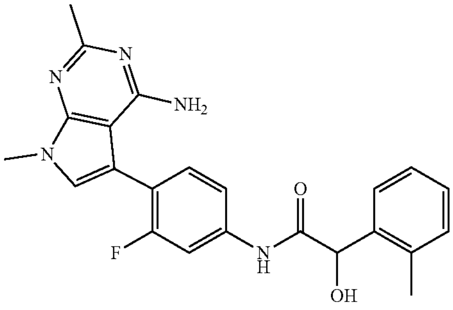<br>Isomer 2 | ESI (m/z) 420 $[C_{23}H_{22}FN_5O_2 + H]^+$ | Scheme G |

TABLE 1-continued

| Compounds of Formula I: | | | | |
|---|---|---|---|---|
| Example | Name | Compounds I | MS | Synthetic Method |
| 73 | N-(4-(4-amino-2,7-dimethyl-7H-pyrrolo[2,3-d]pyrimidin-5-yl)-3-fluorophenyl)-2-hydroxy-2-(m-tolyl)acetamide | 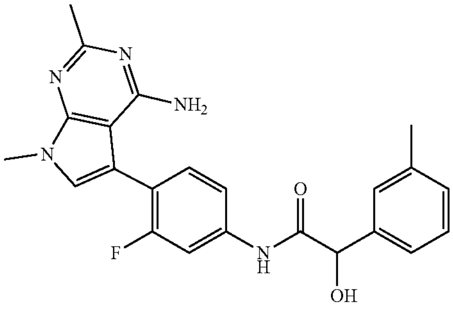 Isomer 1 | ESI (m/z) 420 $[C_{23}H_{22}FN_5O_2 + H]^+$ | Scheme G |
| 74 | N-(4-(4-amino-2,7-dimethyl-7H-pyrrolo[2,3-d]pyrimidin-5-yl)-3-fluorophenyl)-2-hydroxy-2-(m-tolyl)acetamide | 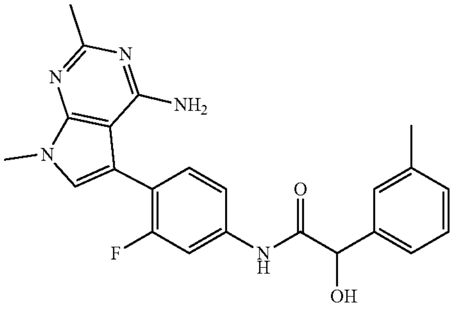 Isomer 2 | ESI (m/z) 420 $[C_{23}H_{22}FN_5O_2 + H]^+$ | Scheme G |
| 75 | N-(4-(4-amino-2,7-dimethyl-7H-pyrrolo[2,3-d]pyrimidin-5-yl)-3-fluorophenyl)-2-(3-ethylphenyl)-2-hydroxyacetamide | 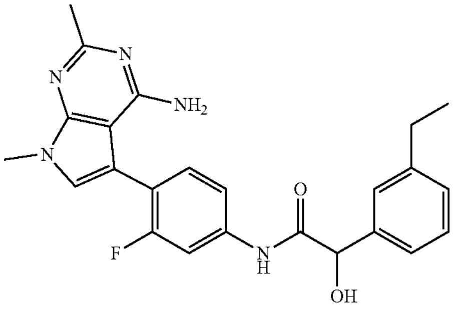 Isomer 1 | ESI (m/z) 434 $[C_{24}H_{24}FN_5O_2 + H]^+$ | Scheme G |
| 76 | N-(4-(4-amino-2,7-dimethyl-7H-pyrrolo[2,3-d]pyrimidin-5-yl)-3-fluorophenyl)-2-(3-ethylphenyl)-2-hydroxyacetamide | 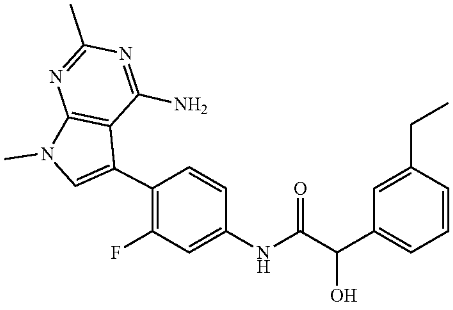 Isomer 2 | ESI (m/z) 434 $[C_{24}H_{24}FN_5O_2 + H]^+$ | Scheme G |

TABLE 1-continued

| Compounds of Formula I: | | | | |
|---|---|---|---|---|
| Example | Name | Compounds I | MS | Synthetic Method |
| 77 | N-(4-(4-amino-2,7-dimethyl-7H-pyrrolo[2,3-d]pyrimidin-5-yl)-3-fluorophenyl)-2-hydroxy-2-(2-(trifluoromethyl)phenyl)acetamide | 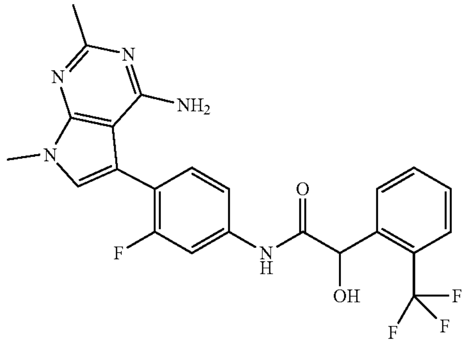 Racemate | ESI (m/z) 474 $[C_{23}H_{19}F_4N_5O_2 + H]^+$ | Scheme G |
| 78 | N-(4-(4-amino-2,7-dimethyl-7H-pyrrolo[2,3-d]pyrimidin-5-yl)-3-fluorophenyl)-2-hydroxy-2-(3-(trifluoromethyl)phenyl)acetamide | 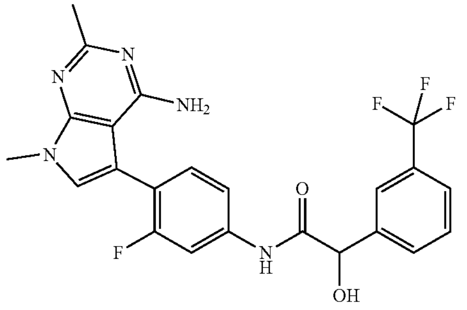 Racemate | ESI (m/z) 474 $[C_{23}H_{19}F_4N_5O_2 + H]^+$ | Scheme G |
| 79 | N-(4-(4-amino-2,7-dimethyl-7H-pyrrolo[2,3-d]pyrimidin-5-yl)-3-fluorophenyl)-2-(3-fluorophenyl)-2-hydroxyacetamide | 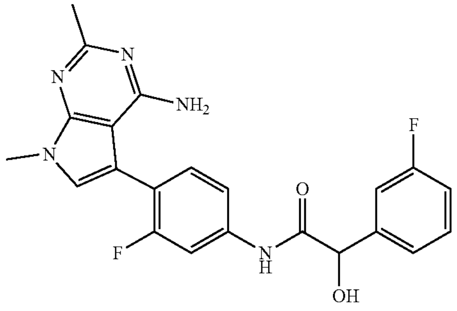 Isomer 1 | ESI (m/z) 424 $[C_{22}H_{19}F_2N_5O_2 + H]^+$ | Scheme G |
| 80 | N-(4-(4-amino-2,7-dimethyl-7H-pyrrolo[2,3-d]pyrimidin-5-yl)-3-fluorophenyl)-2-(3-fluorophenyl)-2-hydroxyacetamide | 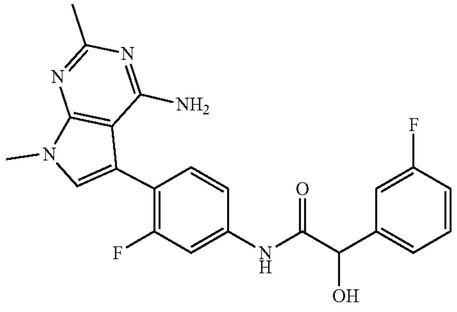 Isomer 2 | ESI (m/z) 424 $[C_{22}H_{19}F_2N_5O_2 + H]^+$ | Scheme G |

TABLE 1-continued

| Compounds of Formula I: | | | | |
|---|---|---|---|---|
| Example | Name | Compounds I | MS | Synthetic Method |
| 81 | N-(4-(4-amino-2,7-dimethyl-7H-pyrrolo[2,3-d]pyrimidin-5-yl)-3-fluorophenyl)-2-(3-chlorophenyl)-2-hydroxyacetamide | 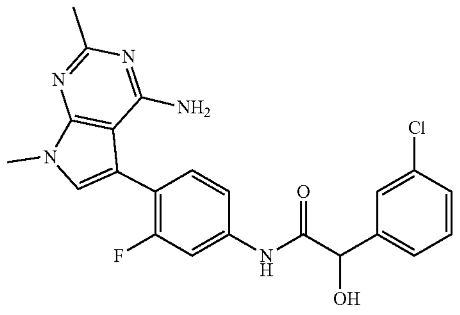 Isomer 1 | ESI (m/z) 440 [$C_{22}H_{19}ClFN_5O_2$ + H]$^+$ | Scheme G |
| 82 | N-(4-(4-amino-2,7-dimethyl-7H-pyrrolo[2,3-d]pyrimidin-5-yl)-3-fluorophenyl)-2-(3-chlorophenyl)-2-hydroxyacetamide | 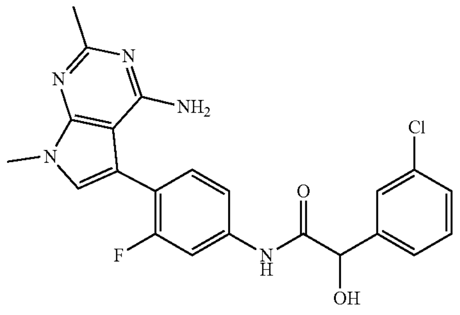 Isomer 2 | ESI (m/z) 440 [$C_{22}H_{19}ClFN_5O_2$ + H]$^+$ | Scheme G |
| 83 | N-(4-(4-amino-2,7-dimethyl-7H-pyrrolo[2,3-d]pyrimidin-5-yl)-3-fluorophenyl)-2-(3,5-difluorophenyl)-2-hydroxyacetamide | 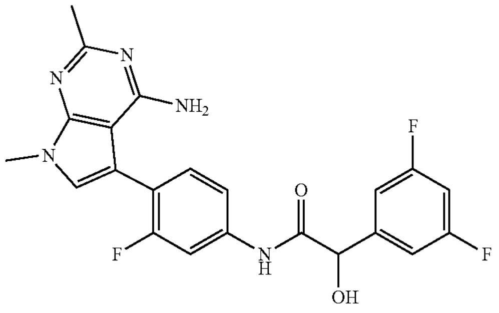 Isomer 1 | ESI (m/z) 442 [$C_{22}H_{18}F_3N_5O_2$ + H]$^+$ | Scheme G |
| 84 | N-(4-(4-amino-2,7-dimethyl-7H-pyrrolo[2,3-d]pyrimidin-5-yl)-3-fluorophenyl)-2-(3,5-difluorophenyl)-2-hydroxyacetamide | 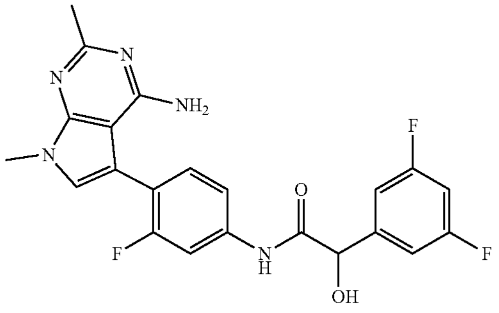 Isomer 2 | ESI (m/z) 442 [$C_{22}H_{18}F_3N_5O_2$ + H]$^+$ | Scheme G |

TABLE 1-continued

Compounds of Formula I:

| Example | Name | Compounds I | MS | Synthetic Method |
|---|---|---|---|---|
| 85 | N-(4-(4-amino-2,7-dimethyl-7H-pyrrolo[2,3-d]pyrimidin-5-yl)-3-fluorophenyl)-2-(3-fluoro-5-methylphenyl)-2-hydroxyacetamide | 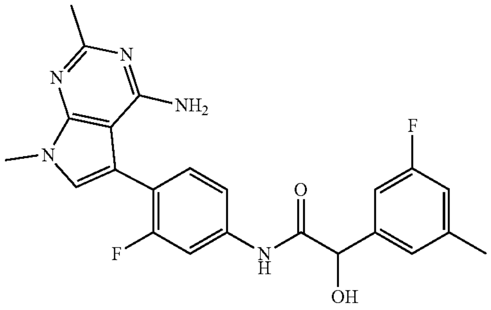 Isomer 1 | ESI (m/z) 438 $[C_{23}H_{21}F_2N_5O_2 + H]^+$ | Scheme G |
| 86 | N-(4-(4-amino-2,7-dimethyl-7H-pyrrolo[2,3-d]pyrimidin-5-yl)-3-fluorophenyl)-2-(3-fluoro-5-methylphenyl)-2-hydroxyacetamide | 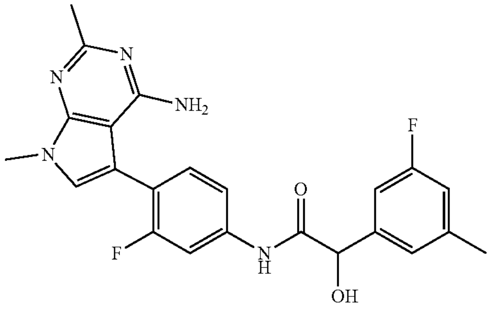 Isomer 2 | ESI (m/z) 438 $[C_{23}H_{21}F_2N_5O_2 + H]^+$ | Scheme G |
| 87 | N-(4-(4-amino-2,7-dimethyl-7H-pyrrolo[2,3-d]pyrimidin-5-yl)-3-fluorophenyl)-2-(3-fluoro-5-(trifluoromethyl)phenyl)-2-hydroxyacetamide | 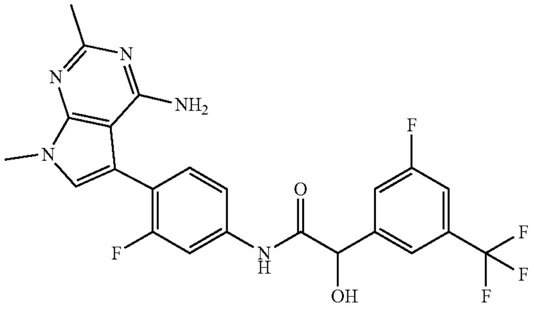 Isomer 1 | ESI (m/z) 492 $[C_{23}H_{18}F_5N_5O_2 + H]^+$ | Scheme G |
| 88 | N-(4-(4-amino-2,7-dimethyl-7H-pyrrolo[2,3-d]pyrimidin-5-yl)-3-fluorophenyl)-2-(3-fluoro-5-(trifluoromethyl)phenyl)-2-hydroxyacetamide | 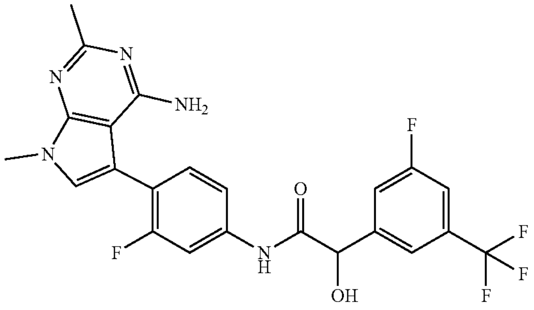 Isomer 2 | ESI (m/z) 492 $[C_{23}H_{18}F_5N_5O_2 + H]^+$ | Scheme G |

TABLE 1-continued

| Compounds of Formula I: | | | | |
|---|---|---|---|---|
| Example | Name | Compounds I | MS | Synthetic Method |
| 89 | N-(4-(4-amino-2,7-dimethyl-7H-pyrrolo[2,3-d]pyrimidin-5-yl)-2-fluorophenyl)-2-(3-fluorophenyl)-2-hydroxyacetamide | 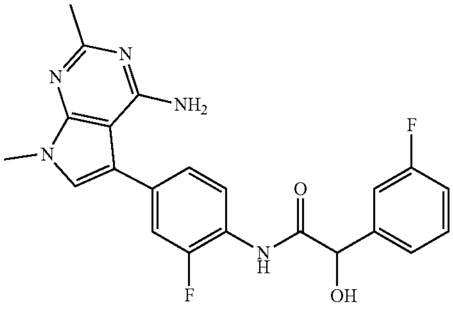 Isomer 1 | ESI (m/z) 424 [$C_{22}H_{19}F_2N_5O_2$ + H]$^+$ | Scheme G |
| 90 | N-(4-(4-amino-2,7-dimethyl-7H-pyrrolo[2,3-d]pyrimidin-5-yl)-2-fluorophenyl)-2-(3-fluorophenyl)-2-hydroxyacetamide | 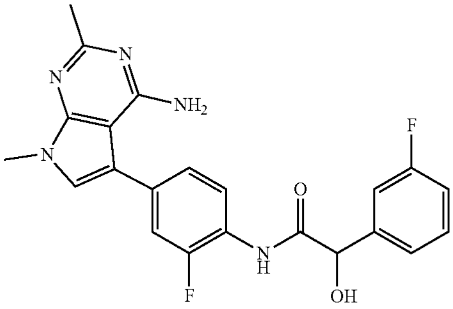 Isomer 2 | ESI (m/z) 424 [$C_{22}H_{19}F_2N_5O_2$ + H]$^+$ | Scheme G |
| 91 | N-(4-(4-amino-2,7-dimethyl-7H-pyrrolo[2,3-d]pyrimidin-5-yl)-3-chlorophenyl)-2-(3-fluorophenyl)-2-hydroxyacetamide | 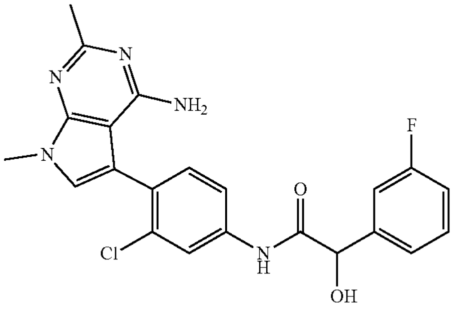 Isomer 1 | ESI (m/z) 440 [$C_{22}H_{19}ClFN_5O_2$ + H]$^+$ | Scheme G |
| 92 | N-(4-(4-amino-2,7-dimethyl-7H-pyrrolo[2,3-d]pyrimidin-5-yl)-3-chlorophenyl)-2-(3-fluorophenyl)-2-hydroxyacetamide | 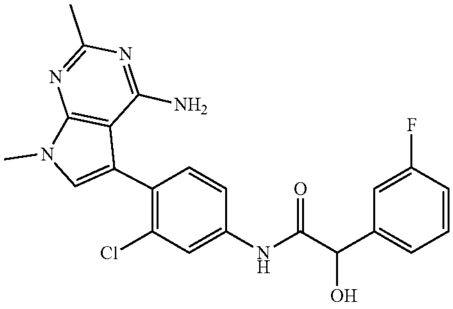 Isomer 2 | ESI (m/z) 440 [$C_{22}H_{19}ClFN_5O_2$ + H]$^+$ | Scheme G |

TABLE 1-continued

| Compounds of Formula I: | | | | |
|---|---|---|---|---|
| Example | Name | Compounds I | MS | Synthetic Method |
| 93 | N-(4-(4-amino-2,7-dimethyl-7H-pyrrolo[2,3-d]pyrimidin-5-yl)-3-chlorophenyl)-2-hydroxy-2-(o-tolyl)acetamide | 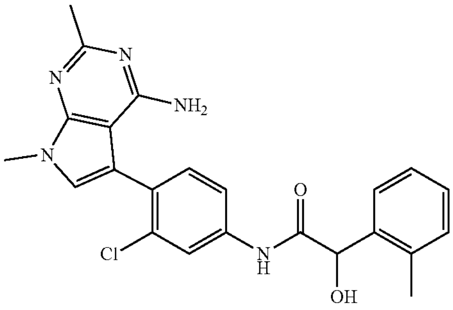 Isomer 1 | ESI (m/z) 436 $[C_{23}H_{22}ClN_5O_2 + H]^+$ | Scheme G |
| 94 | N-(4-(4-amino-2,7-dimethyl-7H-pyrrolo[2,3-d]pyrimidin-5-yl)-3-chlorophenyl)-2-hydroxy-2-(o-tolyl)acetamide | 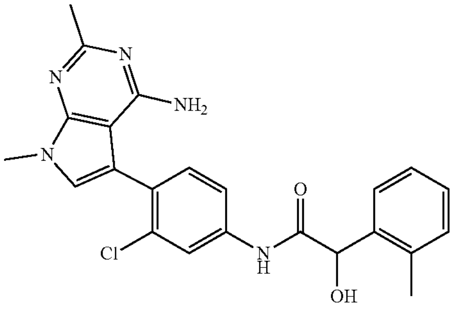 Isomer 2 | ESI (m/z) 436 $[C_{23}H_{22}ClN_5O_2 + H]^+$ | Scheme G |
| 95 | N-(4-(4-amino-2,7-dimethyl-7H-pyrrolo[2,3-d]pyrimidin-5-yl)-3-chlorophenyl)-2-hydroxy-2-(m-tolyl)acetamide | 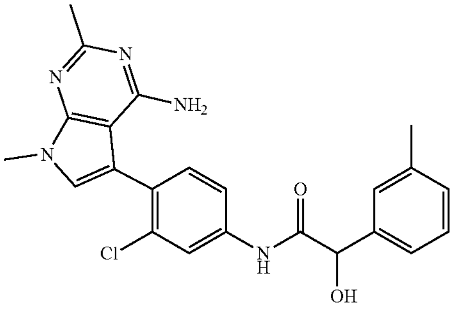 Isomer 1 | ESI (m/z) 436 $[C_{23}H_{22}ClN_5O_2 + H]^+$ | Scheme G |
| 96 | N-(4-(4-amino-2,7-dimethyl-7H-pyrrolo[2,3-d]pyrimidin-5-yl)-3-chlorophenyl)-2-hydroxy-2-(m-tolyl)acetamide | 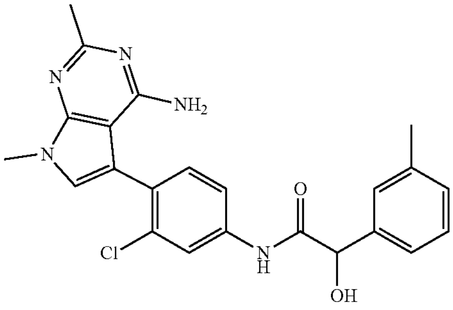 Isomer 2 | ESI (m/z) 436 $[C_{23}H_{22}ClN_5O_2 + H]^+$ | Scheme G |

TABLE 1-continued

Compounds of Formula I:

| Example | Name | Compounds I | MS | Synthetic Method |
|---|---|---|---|---|
| 97 | N-(4-(4-amino-2,7-dimethyl-7H-pyrrolo[2,3-d]pyrimidin-5-yl)-3-chlorophenyl)-2-(3-ethylphenyl)-2-hydroxyacetamide | 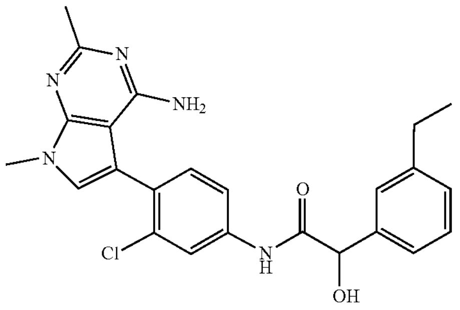 Isomer 1 | ESI (m/z) 450 [$C_{24}H_{24}ClN_5O_2$ + H]$^+$ | Scheme G |
| 98 | N-(4-(4-amino-2,7-dimethyl-7H-pyrrolo[2,3-d]pyrimidin-5-yl)-3-chlorophenyl)-2-(3-ethylphenyl)-2-hydroxyacetamide | 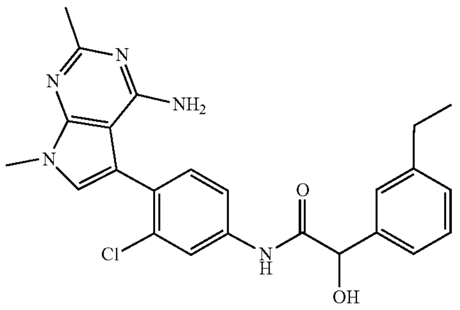 Isomer 2 | ESI (m/z) 450 [$C_{24}H_{24}ClN_5O_2$ + H]$^+$ | Scheme G |
| 99 | N-(4-(4-amino-2,7-dimethyl-7H-pyrrolo[2,3-d]pyrimidin-5-yl)-3-chlorophenyl)-2-(3-chlorophenyl)-2-hydroxyacetamide | 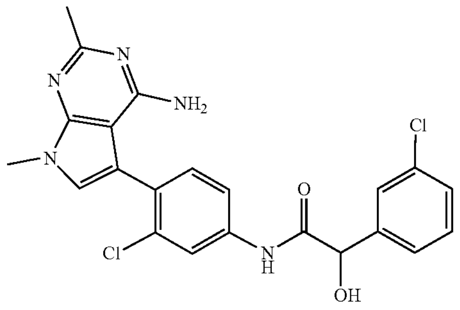 Isomer 1 | ESI (m/z) 456 [$C_{22}H_{19}Cl_2N_5O_2$ + H]$^+$ | Scheme G |
| 100 | N-(4-(4-amino-2,7-dimethyl-7H-pyrrolo[2,3-d]pyrimidin-5-yl)-3-chlorophenyl)-2-(3-chlorophenyl)-2-hydroxyacetamide | 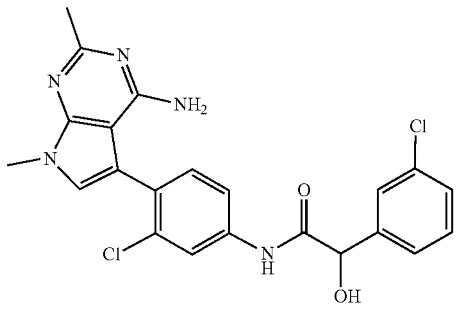 Isomer 2 | ESI (m/z) 456 [$C_{22}H_{19}Cl_2N_5O_2$ + H]$^+$ | Scheme G |

TABLE 1-continued

| Example | Name | Compounds I | MS | Synthetic Method |
|---|---|---|---|---|
| | | Compounds of Formula I: | | |
| 101 | N-(4-(4-amino-2,7-dimethyl-7H-pyrrolo[2,3-d]pyrimidin-5-yl)-3-chlorophenyl)-2-hydroxy-2-(3-(trifluoromethyl)phenyl)acetamide | 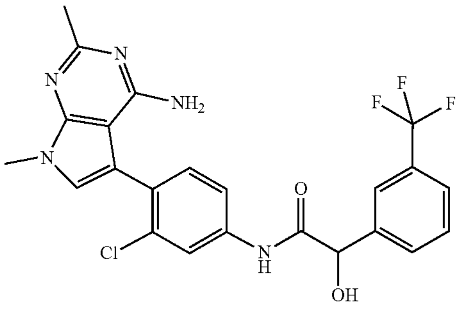 Isomer 1 | ESI (m/z) 490 $[C_{23}H_{19}ClF_3N_5O_2 + H]^+$ | Scheme G |
| 102 | N-(4-(4-amino-2,7-dimethyl-7H-pyrrolo[2,3-d]pyrimidin-5-yl)-3-chlorophenyl)-2-hydroxy-2-(3-(trifluoromethyl)phenyl)acetamide | 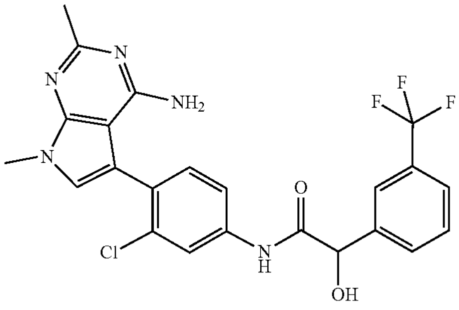 Isomer 2 | ESI (m/z) 490 $[C_{23}H_{19}ClF_3N_5O_2 + H]^+$ | Scheme G |
| 103 | N-(4-(4-amino-7-methyl-7H-pyrrolo[2,3-d]pyrimidin-5-yl)-3-methoxyphenyl)-2-(3-fluorophenyl)-2-hydroxyacetamide | 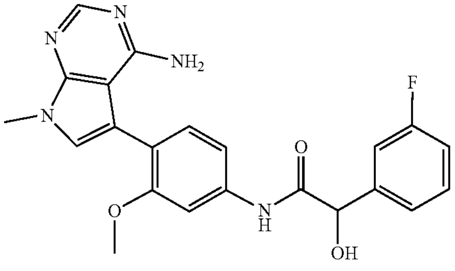 Isomer 1 | ESI (m/z) 422 $[C_{22}H_{20}FN_5O_3 + H]^+$ | Scheme G |
| 104 | N-(4-(4-amino-7-methyl-7H-pyrrolo[2,3-d]pyrimidin-5-yl)-3-methoxyphenyl)-2-(3-fluorophenyl)-2-hydroxyacetamide | 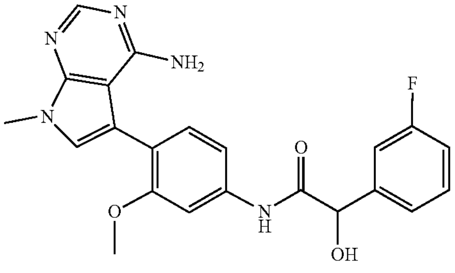 Isomer 2 | ESI (m/z) 422 $[C_{22}H_{20}FN_5O_3 + H]^+$ | Scheme G |

TABLE 1-continued

| Compounds of Formula I: | | | | |
|---|---|---|---|---|
| Example | Name | Compounds I | MS | Synthetic Method |
| 105 | N-(4-(4-amino-2,7-dimethyl-7H-pyrrolo[2,3-d]pyrimidin-5-yl)-3-methoxyphenyl)-2-(3-fluorophenyl)-2-hydroxyacetamide | 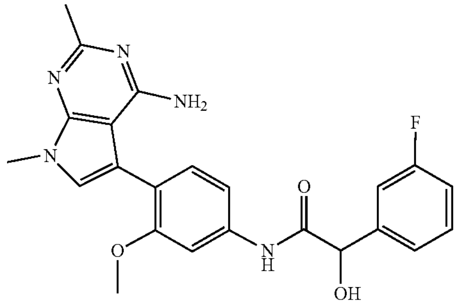 Isomer 1 | ESI (m/z) 436 $[C_{23}H_{22}FN_5O_3 + H]^+$ | Scheme G |
| 106 | N-(4-(4-amino-2,7-dimethyl-7H-pyrrolo[2,3-d]pyrimidin-5-yl)-3-methoxyphenyl)-2-(3-fluorophenyl)-2-hydroxyacetamide | 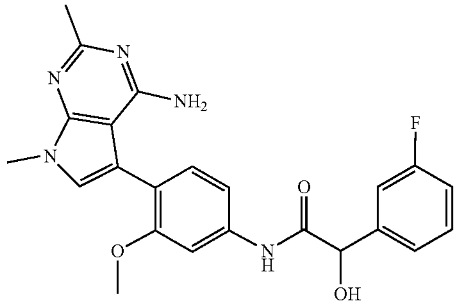 Isomer 2 | ESI (m/z) 436 $[C_{23}H_{22}FN_5O_3 + H]^+$ | Scheme G |
| 107 | N-(4-(4-amino-2,7-dimethyl-7H-pyrrolo[2,3-d]pyrimidin-5-yl)-2,3-difluorophenyl)-2-hydroxy-2-(3-(trifluoromethyl)phenyl)acetamide | 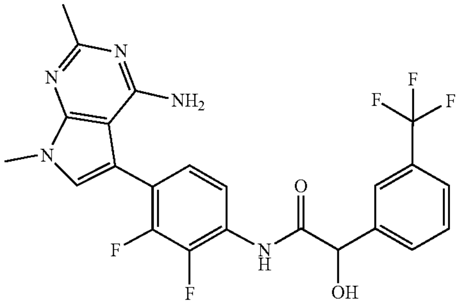 Isomer 1 | ESI (m/z) 492 $[C_{23}H_{18}F_5N_5O_2 + H]^+$ | Scheme G |
| 108 | N-(4-(4-amino-2,7-dimethyl-7H-pyrrolo[2,3-d]pyrimidin-5-yl)-2,3-difluorophenyl)-2-hydroxy-2-(3-(trifluoromethyl)phenyl)acetamide | 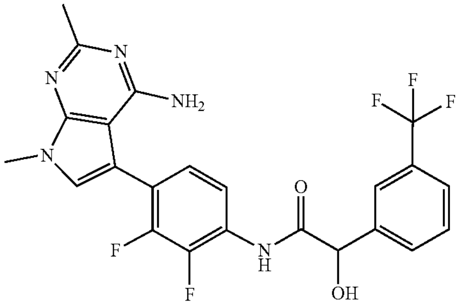 Isomer 2 | ESI (m/z) 492 $[C_{23}H_{18}F_5N_5O_2 + H]^+$ | Scheme G |

TABLE 1-continued

| Compounds of Formula I: | | | | |
|---|---|---|---|---|
| Example | Name | Compounds I | MS | Synthetic Method |
| 109 | N-(4-(4-amino-2,7-dimethyl-7H-pyrrolo[2,3-d]pyrimidin-5-yl)-2,3-difluorophenyl)-2-(3-fluorophenyl)-2-hydroxyacetamide | 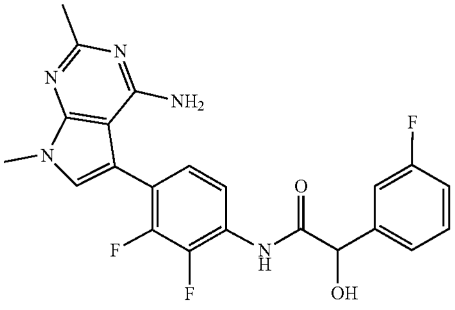 Isomer 1 | ESI (m/z) 442 $[C_{22}H_{18}F_3N_5O_2 + H]^+$ | Scheme G |
| 110 | N-(4-(4-amino-2,7-dimethyl-7H-pyrrolo[2,3-d]pyrimidin-5-yl)-2,3-difluorophenyl)-2-(3-fluorophenyl)-2-hydroxyacetamide | 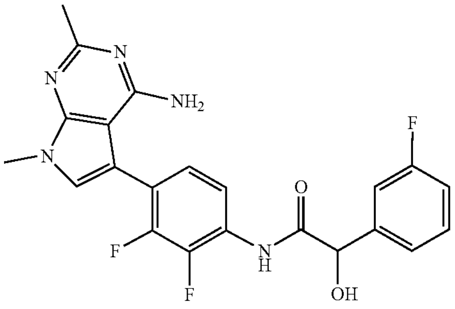 Isomer 2 | ESI (m/z) 442 $[C_{22}H_{18}F_3N_5O_2 + H]^+$ | Scheme G |
| 111 | N-(4-(4-amino-2,7-dimethyl-7H-pyrrolo[2,3-d]pyrimidin-5-yl)-2,3-difluorophenyl)-2-(3-chlorophenyl)-2-hydroxyacetamide | 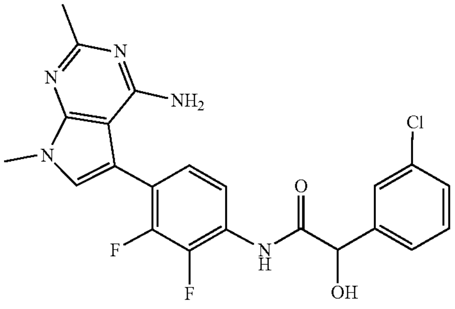 Isomer 1 | ESI (m/z) 458 $[C_{22}H_{18}ClF_2N_5O_2 + H]^+$ | Scheme G |
| 112 | N-(4-(4-amino-2,7-dimethyl-7H-pyrrolo[2,3-d]pyrimidin-5-yl)-2,3-difluorophenyl)-2-(3-chlorophenyl)-2-hydroxyacetamide | 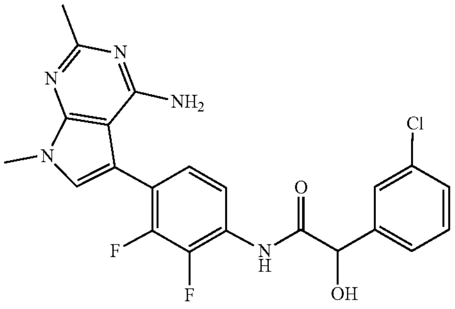 Isomer 2 | ESI (m/z) 458 $[C_{22}H_{18}ClF_2N_5O_2 + H]^+$ | Scheme G |

TABLE 1-continued

Compounds of Formula I:

| Example | Name | Compounds I | MS | Synthetic Method |
|---|---|---|---|---|
| 113 | N-(4-(4-amino-2,7-dimethyl-7H-pyrrolo[2,3-d]pyrimidin-5-yl)-2,3-difluorophenyl)-2-(3,5-difluorophenyl)-2-hydroxyacetamide | 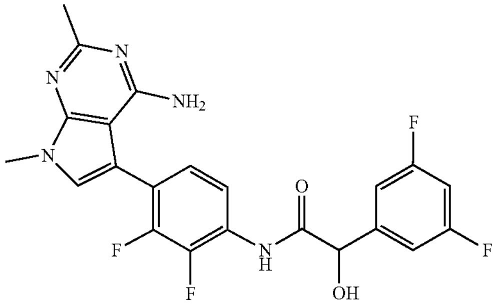 Isomer 1 | ESI (m/z) 460 [$C_{22}H_{17}F_4N_5O_2$ + H]$^+$ | Scheme G |
| 114 | N-(4-(4-amino-2,7-dimethyl-7H-pyrrolo[2,3-d]pyrimidin-5-yl)-2,3-difluorophenyl)-2-(3,5-difluorophenyl)-2-hydroxyacetamide | 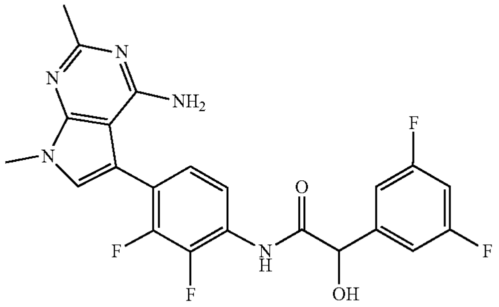 Isomer 2 | ESI (m/z) 460 [$C_{22}H_{17}F_4N_5O_2$ + H]$^+$ | Scheme G |
| 115 | N-(4-(4-amino-2,7-dimethyl-7H-pyrrolo[2,3-d]pyrimidin-5-yl)-2,3-difluorophenyl)-2-(3-fluoro-5-(trifluoromethyl) phenyl)-2-hydroxyacetamide | 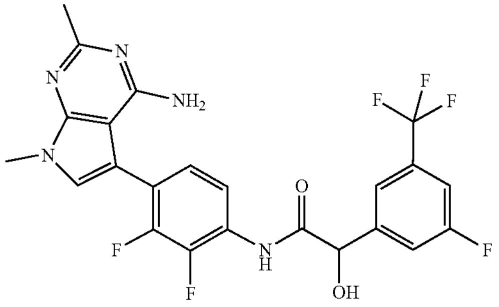 Isomer 1 | ESI (m/z) 510 [$C_{23}H_{17}F_6N_5O_2$ + H]$^+$ | Scheme G |
| 116 | N-(4-(4-amino-2,7-dimethyl-7H-pyrrolo[2,3-d]pyrimidin-5-yl)-2,3-difluorophenyl)-2-(3-fluoro-5-(trifluoromethyl) phenyl)-2-hydroxyacetamide | 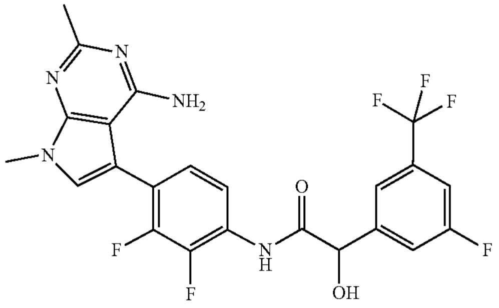 Isomer 2 | ESI (m/z) 510 [$C_{23}H_{17}F_6N_5O_2$ + H]$^+$ | Scheme G |

TABLE 1-continued

| Compounds of Formula I: | | | | |
|---|---|---|---|---|
| Example | Name | Compounds I | MS | Synthetic Method |
| 117 | N-(4-(4-amino-7-methyl-7H-pyrrolo[2,3-d]pyrimidin-5-yl)-2-fluoro-3-methylphenyl)-2-(3-fluorophenyl)-2-hydroxyacetamide | 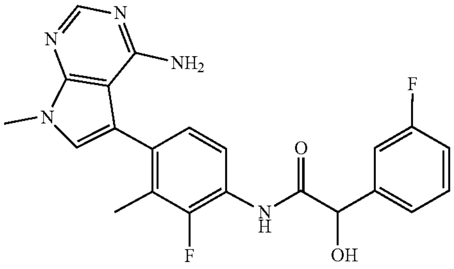 Isomer 1 | ESI (m/z) 424 $[C_{22}H_{19}F_2N_5O_2 + H]^+$ | Scheme H |
| 118 | N-(4-(4-amino-7-methyl-7H-pyrrolo[2,3-d]pyrimidin-5-yl)-2-fluoro-3-methylphenyl)-2-(3-fluorophenyl)-2-hydroxyacetamide | 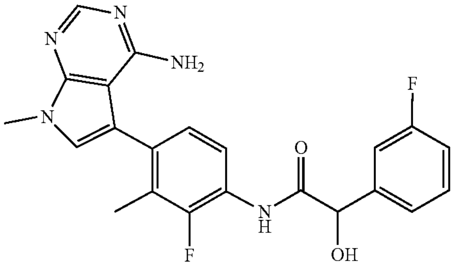 Isomer 2 | ESI (m/z) 424 $[C_{22}H_{19}F_2N_5O_2 + H]^+$ | Scheme H |
| 119 | N-(4-(4-amino-7-methyl-7H-pyrrolo[2,3-d]pyrimidin-5-yl)-2-fluoro-5-methylphenyl)-2-(3-fluorophenyl)-2-hydroxyacetamide | 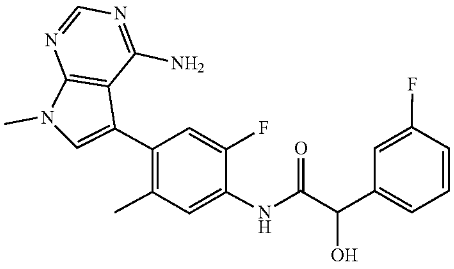 Isomer 1 | ESI (m/z) 424 $[C_{22}H_{19}F_2N_5O_2 + H]^+$ | Scheme H |
| 120 | N-(4-(4-amino-7-methyl-7H-pyrrolo[2,3-d]pyrimidin-5-yl)-2-fluoro-5-methylphenyl)-2-(3-fluorophenyl)-2-hydroxyacetamide | 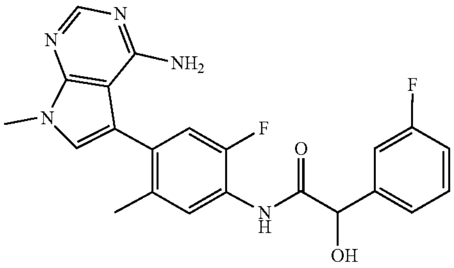 Isomer 2 | ESI (m/z) 424 $[C_{22}H_{19}F_2N_5O_2 + H]^+$ | Scheme H |

TABLE 1-continued

| Compounds of Formula I: | | | | |
|---|---|---|---|---|
| Example | Name | Compounds I | MS | Synthetic Method |
| 121 | N-(4-(4-amino-2,7-dimethyl-7H-pyrrolo[2,3-d]pyrimidin-5-yl)-2-fluoro-5-methylphenyl)-2-(3-fluorophenyl)-2-hydroxyacetamide | 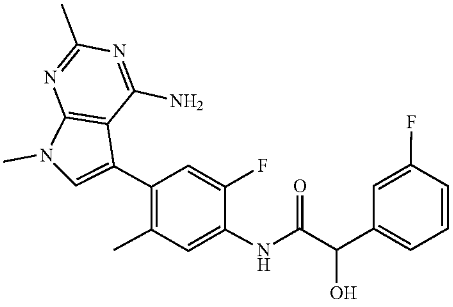 Isomer 1 | ESI (m/z) 438 $[C_{23}H_{21}F_2N_5O_2 + H]^+$ | Scheme H |
| 122 | N-(4-(4-amino-2,7-dimethyl-7H-pyrrolo[2,3-d]pyrimidin-5-yl)-2-fluoro-5-methylphenyl)-2-(3-fluorophenyl)-2-hydroxyacetamide | 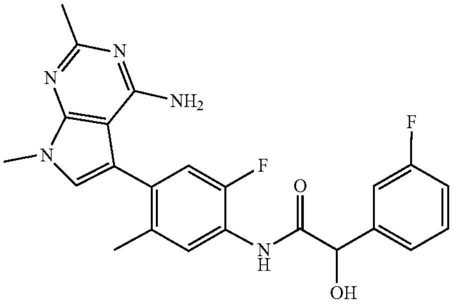 Isomer 2 | ESI (m/z) 438 $[C_{23}H_{21}F_2N_5O_2 + H]^+$ | Scheme H |
| 123 | N-(4-(4-amino-2,7-dimethyl-7H-pyrrolo[2,3-d]pyrimidin-5-yl)-2,5-difluorophenyl)-2-(3-fluorophenyl)-2-hydroxyacetamide | 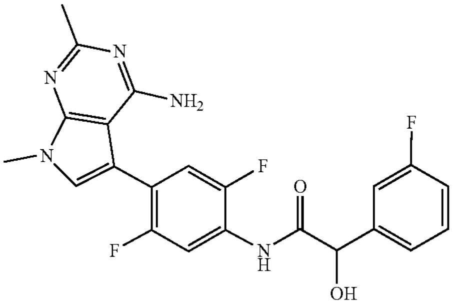 Racemate | ESI (m/z) 442 $[C_{22}H_{18}F_3N_5O_2 + H]^+$ | Scheme H |
| 124 | N-(4-(4-amino-7-methyl-7H-pyrrolo[2,3-d]pyrimidin-5-yl)-3-fluoro-5-methylphenyl)-2-(3-fluorophenyl)-2-hydroxyacetamide | 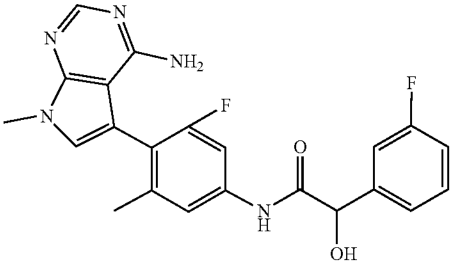 Racemate | ESI (m/z) 424 $[C_{22}H_{19}F_2N_5O_2 + H]^+$ | Scheme H |

TABLE 1-continued

| Compounds of Formula I: | | | | |
|---|---|---|---|---|
| Example | Name | Compounds I | MS | Synthetic Method |
| 125 | N-(4-(4-amino-2,7-dimethyl-7H-pyrrolo[2,3-d]pyrimidin-5-yl)-3-fluoro-5-methylphenyl)-2-(3-fluorophenyl)-2-hydroxyacetamide | 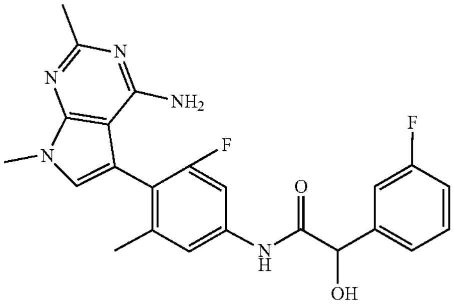 Racemate | ESI (m/z) 438 $[C_{23}H_{21}F_2N_5O_2 + H]^+$ | Scheme H |
| 126 | N-(4-(4-amino-2,7-dimethyl-7H-pyrrolo[2,3-d]pyrimidin-5-yl)-3,5-dimethylphenyl)-2-(3-fluorophenyl)-2-hydroxyacetamide | 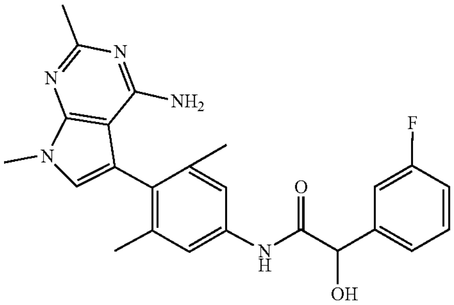 Racemate | ESI (m/z) 434 $[C_{24}H_{24}FN_5O_2 + H]^+$ | Scheme H |
| 127 | N-(5-(4-amino-2,7-dimethyl-7H-pyrrolo[2,3-d]pyrimidin-5-yl)-6-methylpyridin-2-yl)-2-(3-fluorophenyl)-2-hydroxyacetamide | 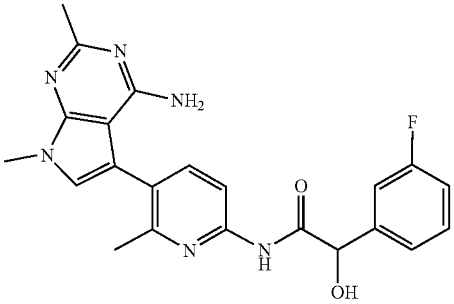 Isomer 1 | ESI (m/z) 421 $[C_{22}H_{21}FN_6O_2 + H]^+$ | Scheme H |
| 128 | N-(5-(4-amino-2,7-dimethyl-7H-pyrrolo[2,3-d]pyrimidin-5-yl)-6-methylpyridin-2-yl)-2-(3-fluorophenyl)-2-hydroxyacetamide | 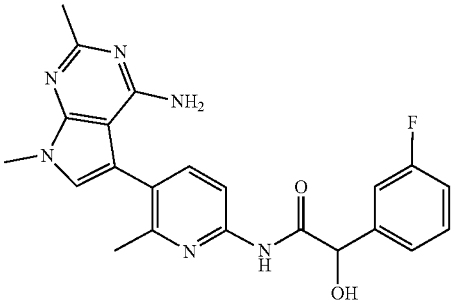 Isomer 2 | ESI (m/z) 421 $[C_{22}H_{21}FN_6O_2 + H]^+$ | Scheme H |

TABLE 1-continued

Compounds of Formula I:

| Example | Name | Compounds I | MS | Synthetic Method |
|---|---|---|---|---|
| 129 | N-(5-(4-amino-2,7-dimethyl-7H-pyrrolo[2,3-d]pyrimidin-5-yl)-6-methylpyridin-2-yl)-2-hydroxy-2-(3-(trifluoromethyl)phenyl)acetamide | 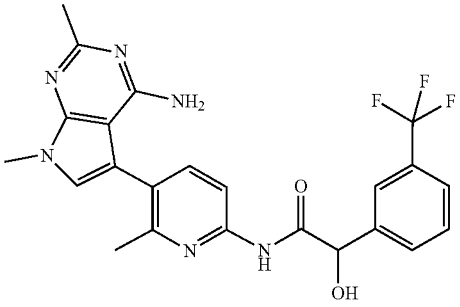 Isomer 1 | ESI (m/z) 471 $[C_{23}H_{21}F_3N_6O_2 + H]^+$ | Scheme H |
| 130 | N-(5-(4-amino-2,7-dimethyl-7H-pyrrolo[2,3-d]pyrimidin-5-yl)-6-methylpyridin-2-yl)-2-hydroxy-2-(3-(trifluoromethyl)phenyl)acetamide | 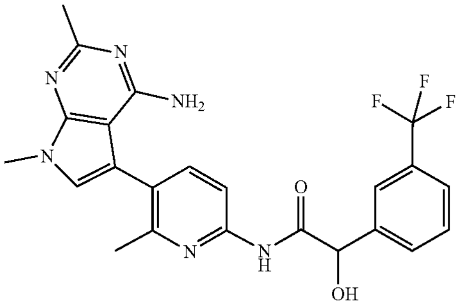 Isomer 2 | ESI (m/z) 471 $[C_{23}H_{21}F_3N_6O_2 + H]^+$ | Scheme H |
| 131 | N-(5-(4-amino-2,7-dimethyl-7H-pyrrolo[2,3-d]pyrimidin-5-yl)-4-methylpyridin-2-yl)-2-hydroxy-2-(3-(trifluoromethyl)phenyl)acetamide | 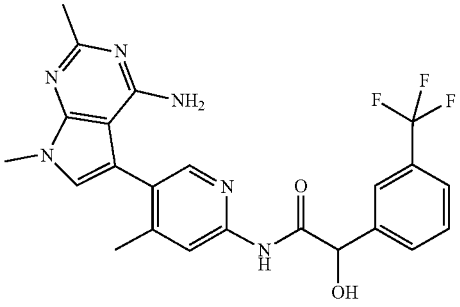 Isomer 1 | ESI (m/z) 471 $[C_{23}H_{21}F_3N_6O_2 + H]^+$ | Scheme H |
| 132 | N-(5-(4-amino-2,7-dimethyl-7H-pyrrolo[2,3-d]pyrimidin-5-yl)-4-methylpyriidn-2-yl)-2-hydroxy-2-(3-(trifluoromethyl)phenyl)acetamide | 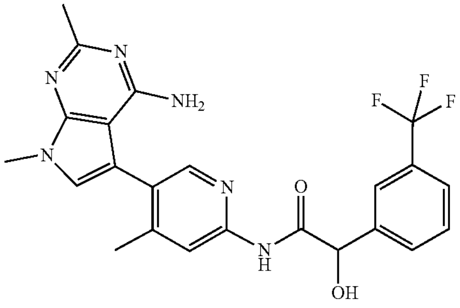 Isomer 2 | ESI (m/z) 471 $[C_{23}H_{21}F_3N_6O_2 + H]^+$ | Scheme H |

TABLE 1-continued

| Compounds of Formula I: | | | | |
|---|---|---|---|---|
| Example | Name | Compounds I | MS | Synthetic Method |
| 133 | N-(5-(4-amino-2,7-dimethyl-7H-pyrrolo[2,3-d]pyrimidin-5-yl)-4-methylpyridin-2-yl)-2-(3-fluorophenyl)-2-hydroxyacetamide | 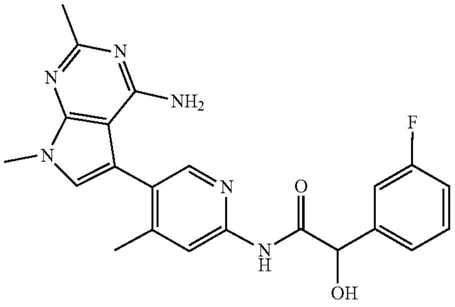 Isomer 1 | ESI (m/z) 421 $[C_{22}H_{21}FN_6O_2 + H]^+$ | Scheme H |
| 134 | N-(5-(4-amino-2,7-dimethyl-7H-pyrrolo[2,3-d]pyrimidin-5-yl)-4-methylpyridin-2-yl)-2-(3-fluorophenyl)-2-hydroxyacetamide | 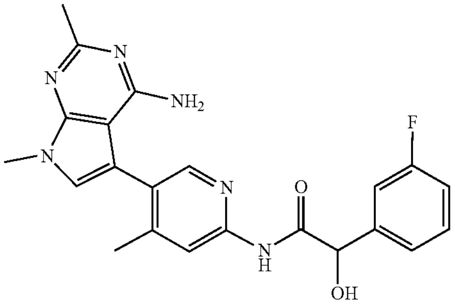 Isomer 2 | ESI (m/z) 421 $[C_{22}H_{21}FN_6O_2 + H]^+$ | Scheme H |
| 135 | N-(4-(4-amino-2,7-dimethyl-7H-pyrrolo[2,3-d]pyrimidin-5-yl)-3-methylphenyl)-2-(6-methylpyridin-2-yl)acetamide | 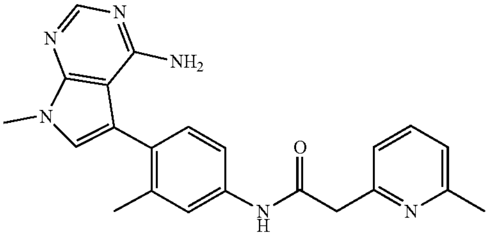 | ESI (m/z) 401 $[C_{23}H_{24}N_6O + H]^+$ | Scheme J |
| 136 | N-(4-(4-amino-7-methyl-7H-pyrrolo[2,3-d]pyrimidin-5-yl)-3-methylphenyl)-2-(6-methylpyridin-2-yl)acetamide | 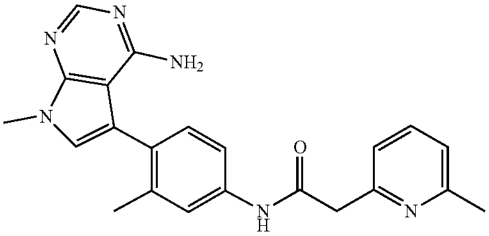 | ESI (m/z) 387 $[C_{22}H_{22}N_6O + H]^+$ | Scheme J |
| 137 | N-(4-(4-amino-7-methyl-7H-pyrrolo[2,3-d]pyrimidin-5-yl)-3-methylphenyl)-2-phenylacetamide | 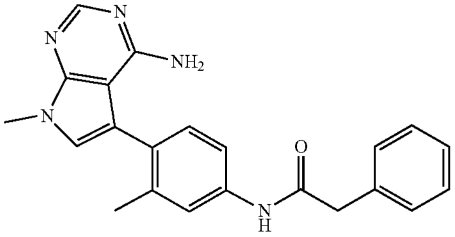 [SMILES: Cc1cc(NC(=O)Cc2ccccc2)ccc1-c1cn(C)c2ncnc(N)c12] | ESI (m/z) 372 $[C_{22}H_{21}N_5O + H]^+$ | Scheme J |

TABLE 1-continued

| Compounds of Formula I: | | | | |
|---|---|---|---|---|
| Example | Name | Compounds I | MS | Synthetic Method |
| 138 | N-(4-(4-amino-7-methyl-7H-pyrrolo[2,3-d]pyrimidin-5-yl)-3-methylphenyl)-2-(2-methoxyphenyl) acetamide | 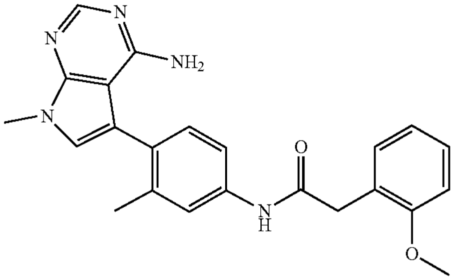 | ESI (m/z) 402 [$C_{23}H_{23}N_5O_2$ + H]$^+$ | Scheme J |
| 139 | N-(4-(4-amino-7-methyl-7H-pyrrolo[2,3-d]pyrimidin-5-yl)-3-methylphenyl)-2-(3-methoxyphenyl) acetamide | 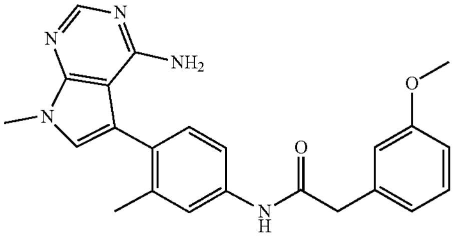 | ESI (m/z) 402 [$C_{23}H_{23}N_5O_2$ + H]$^+$ | Scheme J |
| 140 | N-(4-(4-amino-7-methyl-7H-pyrrolo[2,3-d]pyrimidin-5-yl)-3-methylphenyl)-2-(4-fluorophenyl) acetamide | 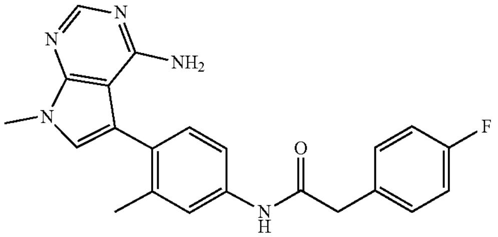 [SMILES: Cc1cc(NC(=O)Cc2ccc(F)cc2)ccc1-c1cn(C)c2ncnc(N)c12] | ESI (m/z) 390 [$C_{22}H_{20}FN_5O$ + H]$^+$ | Scheme J |
| 141 | N-(4-(4-amino-7-methyl-7H-pyrrolo[2,3-d]pyrimidin-5-yl)-3-methylphenyl)-2-(4-methoxyphenyl) acetamide | 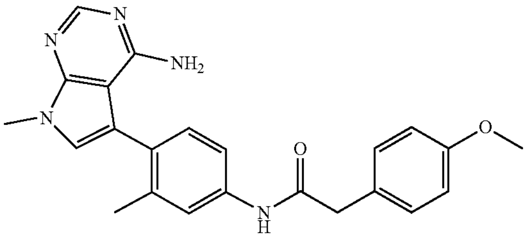 | ESI (m/z) 402 [$C_{23}H_{23}N_5O_2$ + H]$^+$ | Scheme J |
| 142 | N-(4-(4-amino-7-methyl-7H-pyrrolo[2,3-d]pyrimidin-5-yl)-3-methylphenyl)-2-(o-tolyl)acetamide | 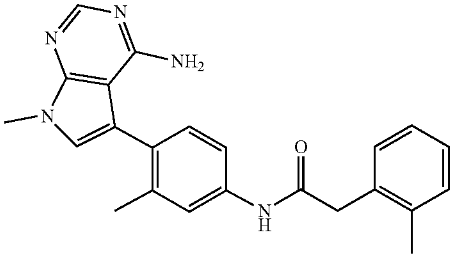 [SMILES: Cc1ccccc1CC(=O)Nc1ccc(-c2cn(C)c3ncnc(N)c23)c(C)c1] | ESI (m/z) 386 [$C_{23}H_{23}N_5O$ + H]$^+$ | Scheme J |
| 143 | N-(4-(4-amino-7-methyl-7H-pyrrolo[2,3-d]pyrimidin-5-yl)-3-methylphenyl)-2-(m-tolyl)acetamide | 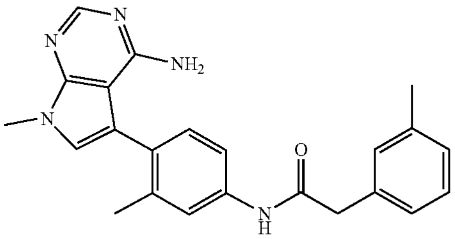 [SMILES: Cc1cccc(CC(=O)Nc2ccc(-c3cn(C)c4ncnc(N)c34)c(C)c2)c1] | ESI (m/z) 386 [$C_{23}H_{23}N_5O$ + H]$^+$ | Scheme J |

TABLE 1-continued

Compounds of Formula I:

| Example | Name | Compounds I | MS | Synthetic Method |
|---|---|---|---|---|
| 144 | N-(4-(4-amino-7-methyl-7H-pyrrolo[2,3-d]pyrimidin-5-yl)-3-methylphenyl)-2-(p-tolyl)acetamide | 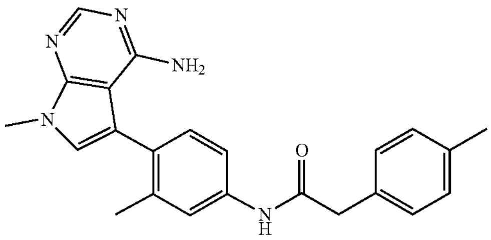 | ESI (m/z) 386 [$C_{23}H_{23}N_5O$ + H]$^+$ | Scheme J |
| 145 | N-(4-(4-amino-7-methyl-7H-pyrrolo[2,3-d]pyrimidin-5-yl)-3-methylphenyl)-2-(2-ethylphenyl) acetamide | 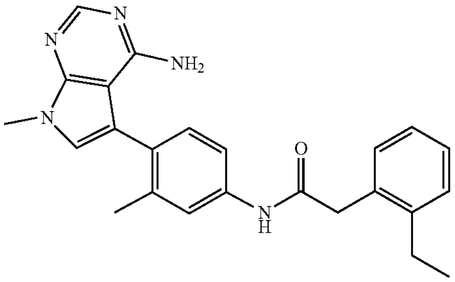 [SMILES: CCc1ccccc1CC(=O)Nc1ccc(-c2cn(C)c3ncnc(N)c23)c(C)c1] | ESI (m/z) 400 [$C_{24}H_{25}N_5O$ + H]$^+$ | Scheme J |
| 146 | N-(4-(4-amino-7-methyl-7H-pyrrolo[2,3-d]pyrimidin-5-yl)-3-methylphenyl)-2-(3-ethylphenyl) acetamide | 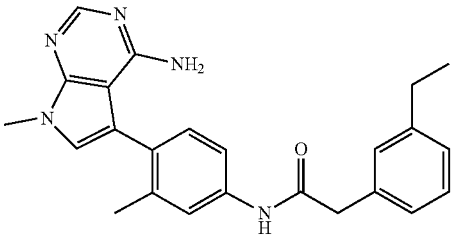 [SMILES: CCc1cccc(CC(=O)Nc2ccc(-c3cn(C)c4ncnc(N)c34)c(C)c2)c1] | ESI (m/z) 400 [$C_{24}H_{25}N_5O$ + H]$^+$ | Scheme J |
| 147 | N-(4-(4-amino-7-methyl-7H-pyrrolo[2,3-d]pyrimidin-5-yl)-3-methylphenyl)-2-(4-ethylphenyl) acetamide | 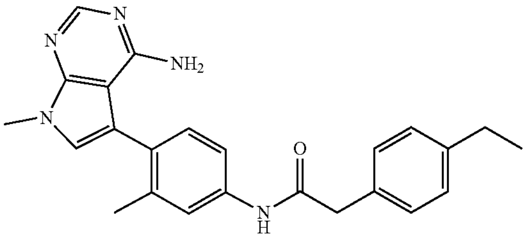 [SMILES: CCc1ccc(CC(=O)Nc2ccc(-c3cn(C)c4ncnc(N)c34)c(C)c2)cc1] | ESI (m/z) 400 [$C_{24}H_{25}N_5O$ + H]$^+$ | Scheme J |
| 148 | N-(4-(4-amino-7-methyl-7H-pyrrolo[2,3-d]pyrimidin-5-yl)-3-methylphenyl)-2-(3-isopropylphenyl) acetamide | 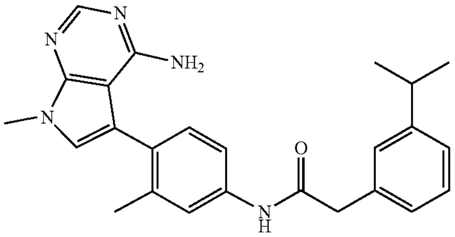 [SMILES: Cc1cc(NC(=O)Cc2cccc(C(C)C)c2)ccc1-c1cn(C)c2ncnc(N)c12] | ESI (m/z) 414 [$C_{25}H_{27}N_5O$ + H]$^+$ | Scheme J |
| 149 | N-(4-(4-amino-7-methyl-7H-pyrrolo[2,3-d]pyrimidin-5-yl)-3-methylphenyl)-2-(2-chlorophenyl) acetamide | 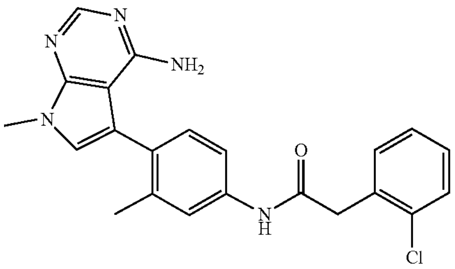 [SMILES: Cc1cc(NC(=O)Cc2ccccc2Cl)ccc1-c1cn(C)c2ncnc(N)c12] | ESI (m/z) 406 [$C_{22}H_{20}ClN_5O$ + H]$^+$ | Scheme J |

TABLE 1-continued

| Compounds of Formula I: | | | | |
|---|---|---|---|---|
| Example | Name | Compounds I | MS | Synthetic Method |
| 150 | N-(4-(4-amino-7-methyl-7H-pyrrolo[2,3-d]pyrimidin-5-yl)-3-methylphenyl)-2-(3-chlorophenyl) acetamide | 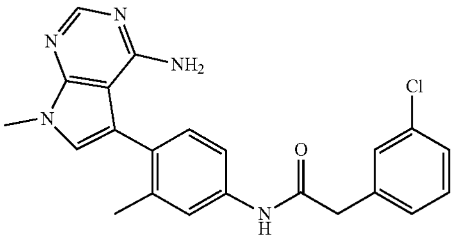 [SMILES: Cc1cc(NC(=O)Cc2cccc(Cl)c2)ccc1-c1cn(C)c2ncnc(N)c12] | ESI (m/z) 406 $[C_{22}H_{20}ClN_5O + H]^+$ | Scheme J |
| 151 | N-(4-(4-amino-7-methyl-7H-pyrrolo[2,3-d]pyrimidin-5-yl)-3-methylphenyl)-2-(4-chlorophenyl) acetamide | 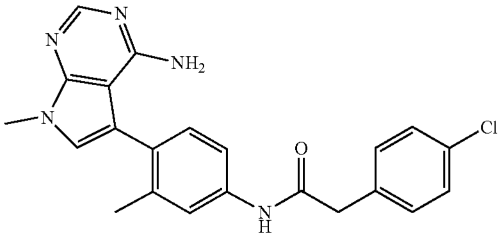 [SMILES: Cc1cc(NC(=O)Cc2ccc(Cl)cc2)ccc1-c1cn(C)c2ncnc(N)c12] | ESI (m/z) 406 $[C_{22}H_{20}ClN_5O + H]^+$ | Scheme J |
| 152 | N-(4-(4-amino-7-methyl-7H-pyrrolo[2,3-d]pyrimidin-5-yl)-3-methylphenyl)-2-(naphthalen-2-yl)acetamide | 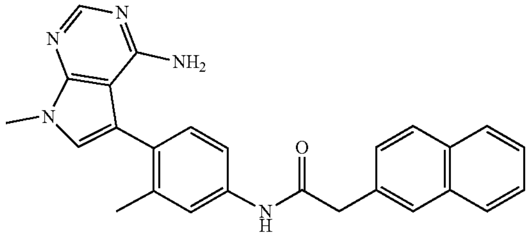 [SMILES: Cc1cc(NC(=O)Cc2ccc3ccccc3c2)ccc1-c1cn(C)c2ncnc(N)c12] | ESI (m/z) 422 $[C_{26}H_{23}N_5O + H]^+$ | Scheme J |
| 153 | N-(4-(4-amino-7-methyl-7H-pyrrolo[2,3-d]pyrimidin-5-yl)-3-methylphenyl)-2-(naphthalen-1-yl)acetamide | 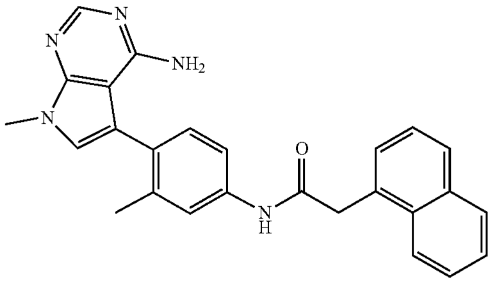 [SMILES: Cc1cc(NC(=O)Cc2cccc3ccccc23)ccc1-c1cn(C)c2ncnc(N)c12] | ESI (m/z) 422 $[C_{26}H_{23}N_5O + H]^+$ | Scheme J |
| 154 | N-(4-(4-amino-7-methyl-7H-pyrrolo[2,3-d]pyrimidin-5-yl)-3-methylphenyl)-2-(quinolin-5-yl)acetamide | 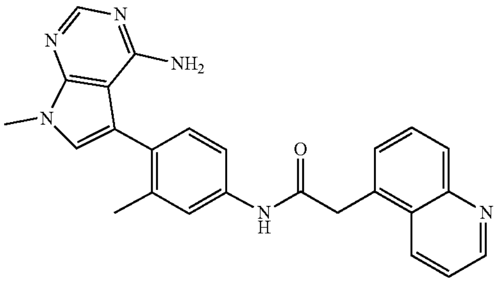 [SMILES: Cc1cc(NC(=O)Cc2cccc3ncccc23)ccc1-c1cn(C)c2ncnc(N)c12] | ESI (m/z) 423 $[C_{25}H_{22}N_6O + H]^+$ | Scheme J |

TABLE 1-continued

| Compounds of Formula I: | | | | |
|---|---|---|---|---|
| Example | Name | Compounds I | MS | Synthetic Method |
| 155 | N-(4-(4-amino-7-methyl-7H-pyrrolo[2,3-d]pyrimidin-5-yl)-3-methylphenyl)-2-(isoquinolin-4-yl)acetamide | 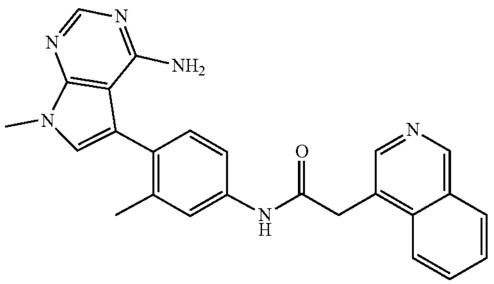 [SMILES: Cc1cc(NC(=O)Cc2cncc3ccccc23)ccc1-c1cn(C)c2ncnc(N)c12] | ESI (m/z) 423 [$C_{25}H_{22}N_6O$ + H]$^+$ | Scheme J |
| 156 | N-(4-(4-amino-7-methyl-7H-pyrrolo[2,3-d]pyrimidin-5-yl)-3-methylphenyl)-2-(isoquinolin-5-yl)acetamide | 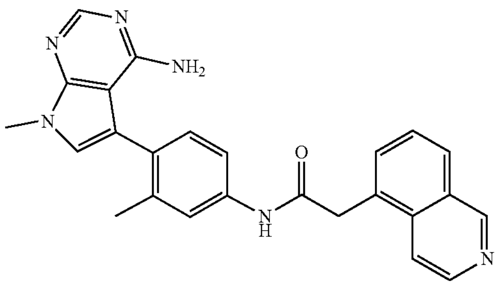 [SMILES: Cc1cc(NC(=O)Cc2cccc3cnccc23)ccc1-c1cn(C)c2ncnc(N)c12] | ESI (m/z) 423 [$C_{25}H_{22}N_6O$ + H]$^+$ | Scheme J |
| 157 | N-(4-(4-amino-7-methyl-7H-pyrrolo[2,3-d]pyrimidin-5-yl)-3-methylphenyl)-2-(2-(trifluoromethyl) phenyl)acetamide | 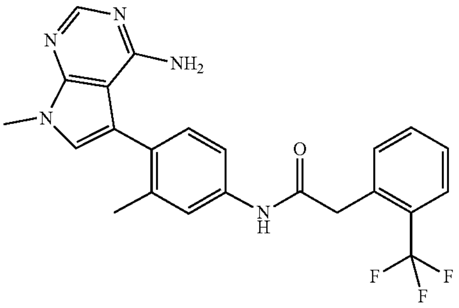 [SMILES: Cc1cc(NC(=O)Cc2ccccc2C(F)(F)F)ccc1-c1cn(C)c2ncnc(N)c12] | ESI (m/z) 440 [$C_{23}H_{20}F_3N_5O$ + H]$^+$ | Scheme J |
| 158 | N-(4-(4-amino-7-methyl-7H-pyrrolo[2,3-d]pyrimidin-5-yl)-3-methylphenyl)-2-(3-(trifluoromethyl) phenyl)acetamide | 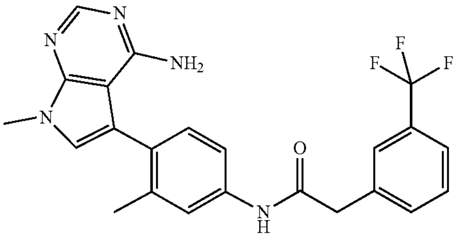 [SMILES: Cc1cc(NC(=O)Cc2cccc(C(F)(F)F)c2)ccc1-c1cn(C)c2ncnc(N)c12] | ESI (m/z) 440 [$C_{23}H_{20}F_3N_5O$ + H]$^+$ | Scheme J |
| 159 | N-(4-(4-amino-7-methyl-7H-pyrrolo[2,3-d]pyrimidin-5-yl)-3-methylphenyl)-2-(4-(trifluoromethyl) phenyl)acetamide | 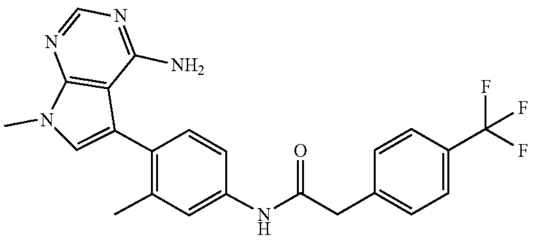 [SMILES: Cc1cc(NC(=O)Cc2ccc(C(F)(F)F)cc2)ccc1-c1cn(C)c2ncnc(N)c12] | ESI (m/z) 440 [$C_{23}H_{20}F_3N_5O$ + H]$^+$ | Scheme J |

TABLE 1-continued

| Compounds of Formula I: | | | | |
|---|---|---|---|---|
| Example | Name | Compounds I | MS | Synthetic Method |
| 160 | N-(4-(4-amino-7-methyl-7H-pyrrolo[2,3-d]pyrimidin-5-yl)-3-methylphenyl)-2-(2-fluorophenyl) acetamide | 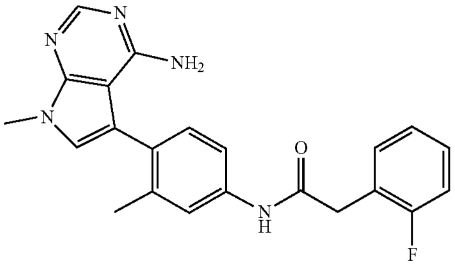 [SMILES: Cc1cc(NC(=O)Cc2ccccc2F)ccc1-c1cn(C)c2ncnc(N)c12] | ESI (m/z) 390 [$C_{22}H_{20}FN_5O$ + H]$^+$ | Scheme J |
| 161 | N-(4-(4-amino-7-methyl-7H-pyrrolo[2,3-d]pyrimidin-5-yl)-3-methylphenyl)-fluorophenyl) acetamide | 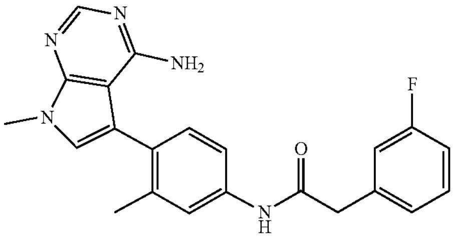 | ESI (m/z) 390 [$C_{22}H_{19}F_4N_5O_3$ + H]$^+$ | Scheme J |
| 162 | N-(4-(4-amino-7-methyl-7H-pyrrolo[2,3-d]pyrimidin-5-yl)-3-methylphenyl)-2-(2,3-dimethylphenyl) acetamide | 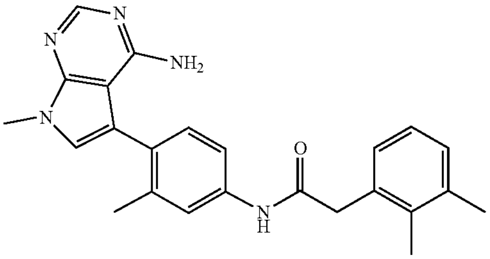 | ESI (m/z) 400 [$C_{24}H_{25}N_5O$ + H]$^+$ | Scheme J |
| 163 | N-(4-(4-amino-7-methyl-7H-pyrrolo[2,3-d]pyrimidin-5-yl)-3-methylphenyl)-2-cyclopropyl-acetamide | 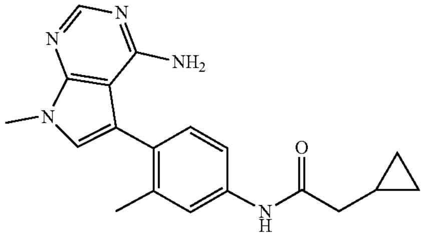 [SMILES: Cc1cc(NC(=O)CC2CC2)ccc1-c1cn(C)c2ncnc(N)c12] | ESI (m/z) 336 [$C_{19}H_{21}N_5O$ + H]$^+$ | Scheme J |
| 164 | N-(4-(4-amino-7-methyl-7H-pyrrolo[2,3-d]pyrimidin-5-yl)-3-methylphenyl)-2-cyclobutyl-acetamide | 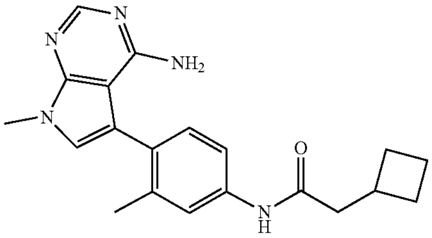 [SMILES: Cc1cc(NC(=O)CC2CCC2)ccc1-c1cn(C)c2ncnc(N)c12] | ESI (m/z) 350 [$C_{20}H_{23}N_5O$ + H]$^+$ | Scheme J |
| 165 | N-(4-(4-amino-7-methyl-7H-pyrrolo[2,3-d]pyrimidin-5-yl)-3-methylphenyl)-2-cyclopentyl-acetamide | 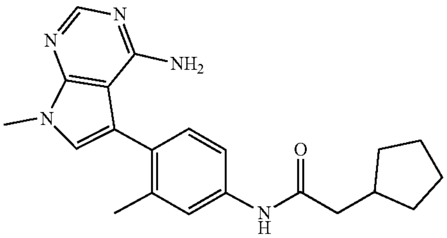 [SMILES: Cc1cc(NC(=O)CC2CCCC2)ccc1-c1cn(C)c2ncnc(N)c12] | ESI (m/z) 364 [$C_{21}H_{25}N_5O$ + H]$^+$ | Scheme J |

TABLE 1-continued

Compounds of Formula I:

| Example | Name | Compounds I | MS | Synthetic Method |
|---|---|---|---|---|
| 166 | N-(4-(4-amino-7-methyl-7H-pyrrolo[2,3-d]pyrimidin-5-yl)-3-methylphenyl)-2-cyclohexyl-acetamide | 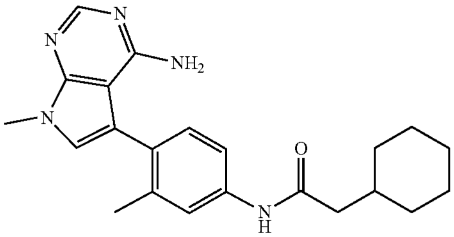 [SMILES: Cc1cc(NC(=O)CC2CCCCC2)ccc1-c1cn(C)c2ncnc(N)c12] | ESI (m/z) 378 $[C_{22}H_{27}N_5O + H]^+$ | Scheme J |
| 167 | N-(4-(4-amino-7-methyl-7H-pyrrolo[2,3-d]pyrimidin-5-yl)-3-methylphenyl) benzamide | 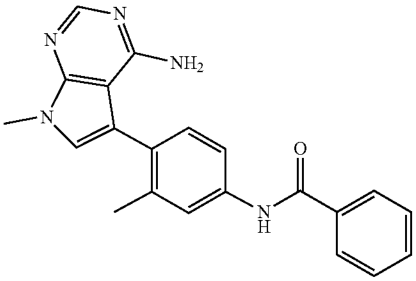 [SMILES: Cc1cc(NC(=O)c2ccccc2)ccc1-c1cn(C)c2ncnc(N)c12] | ESI (m/z) 358 $[C_{21}H_{19}N_5O + H]^+$ | Scheme J |
| 168 | N-(4-(4-amino-7-methyl-7H-pyrrolo[2,3-d]pyrimidin-5-yl)-3-methylphenyl)-3-phenylpropanamide | 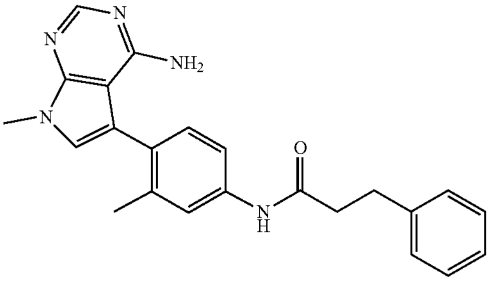 [SMILES: Cc1cc(NC(=O)CCc2ccccc2)ccc1-c1cn(C)c2ncnc(N)c12] | ESI (m/z) 387 $[C_{22}H_{22}N_6O + H]^+$ | Scheme J |
| 169 | phenyl (4-(4-amino-7-methyl-7H-pyrrolo[2,3-d]pyrimidin-5-yl)-3-methylphenyl) carbamate | 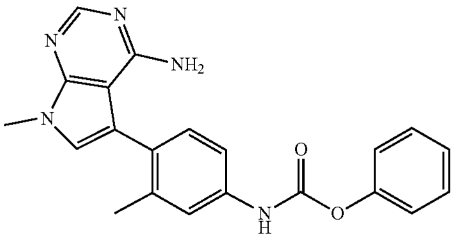 [SMILES: Cc1cc(NC(=O)Oc2ccccc2)ccc1-c1cn(C)c2ncnc(N)c12] | ESI (m/z) 374 $[C_{21}H_{19}N_5O_2 + H]^+$ | Scheme K |
| 170 | 1-(4-(4-amino-7-methyl-7H-pyrrolo[2,3-d]pyrimidin-5-yl)-3-methylphenyl)-3-phenylurea | 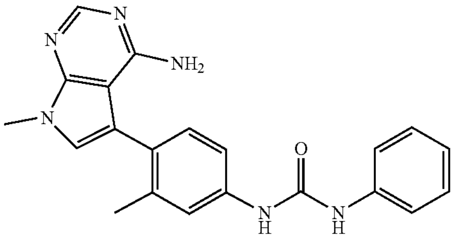 [SMILES: Cc1cc(NC(=O)Nc2ccccc2)ccc1-c1cn(C)c2ncnc(N)c12] | ESI (m/z) 373 $[C_{21}H_{20}N_6O + H]^+$ | Scheme L |

TABLE 1-continued

| Compounds of Formula I: | | | | |
|---|---|---|---|---|
| Example | Name | Compounds I | MS | Synthetic Method |
| 171 | 3-(4-(4-amino-7-methyl-7H-pyrrolo[2,3-d]pyrimidin-5-yl)-3-methylphenyl)-1-methyl-1-phenylurea | 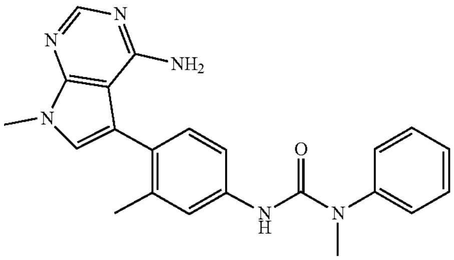 [SMILES: Cc1cc(NC(=O)N(C)c2ccccc2)ccc1-c1cn(C)c2ncnc(N)c12] | ESI (m/z) 387 $[C_{22}H_{22}N_6O + H]^+$ | Scheme M |

Solubility

Compound of Formula Ic when $R^{3b}$=OH (Example 6) has the benefit of additional PERK inhibitory effects (biochemical and cellular potency) and increased solubility versus compound of Formula Ic where $R^{3b}$=H, Compound A (synthesized according to Scheme G where B-1 is replaced with phenylacetic acid) as noted in Table 2, below.

TABLE 2

Biochemical potency, cellular potency and solubility comparison of Compound A versus Example 6

| | $R^1$ | $R^2$ | $R^{3b}$ | $R^5$ | $R^6$ | PERK $IC_{50}$ (μM) | P-EIF2α $IC_{50}$ (μM) | Aq Sol (μM) |
|---|---|---|---|---|---|---|---|---|
| Compound A | H | 3-Me | H | Me | H | 0.006 | 0.041 | 14 |
| Example 6 | H | 3-Me | OH | Me | H | 0.002 | 0.023 | 57 |

Kinase Selectivity

Figure 2:
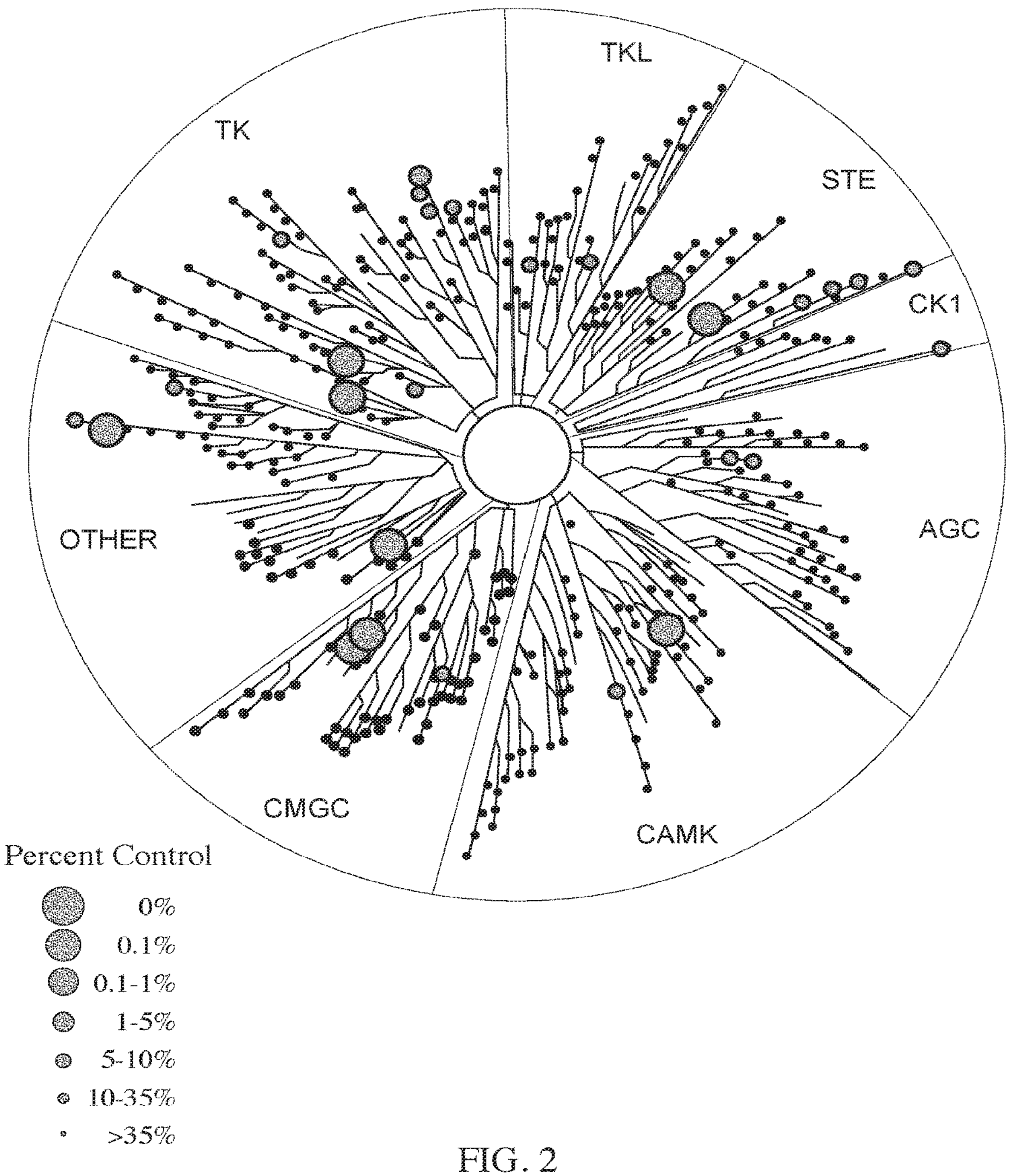
FIG. 2 illustrates a kinase selectivity interaction map for Example 9.
Figure 3:
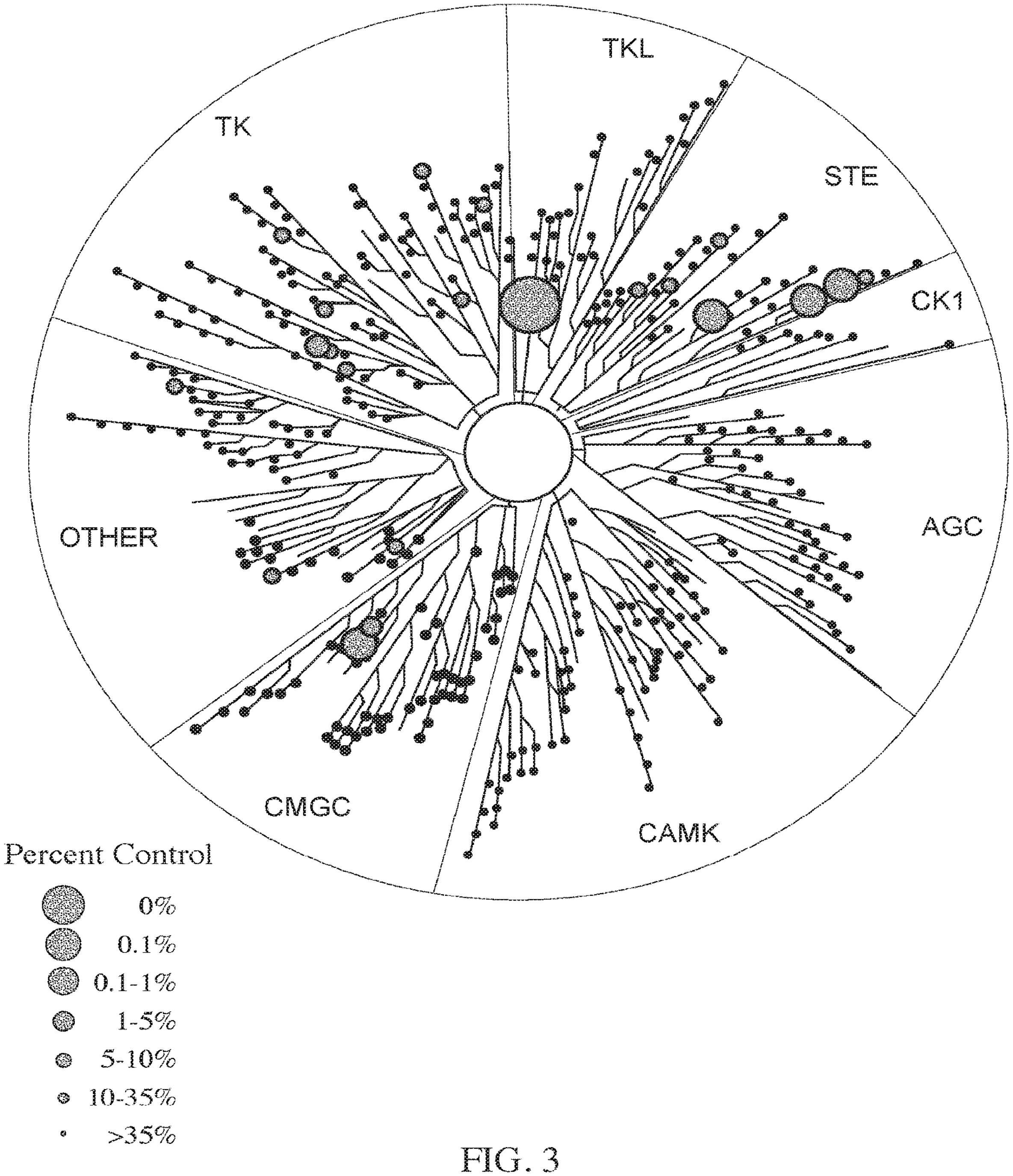
FIG. 3 illustrates a kinase selectivity interaction map for GSK2656157.

Compound of Formula Id when $R^6$=Me (Example 1) is more selective than compound of Formula (Id) where $R^6$=H (Example 9) and multi-kinase inhibitor GSK2656157 as noted in Table 3, Treespot™ analysis in FIGS. 1-3 (experiments performed by KINOMEscan®, San Diego, CA), and Table 4 (experiments performed by KINOMEscan®, San Diego, CA).

TABLE 3

Structures of Examples 1 and 9 where R variables refer to Formula (Id)

| | $R^1$ | $R^2$ | $R^5$ | $R^6$ |
|---|---|---|---|---|
| Example 1 | 3-F | 3-Me | Me | Me |
| Example 9 | 3-F | 3-Me | Me | H |

Structure of GSK2656157:

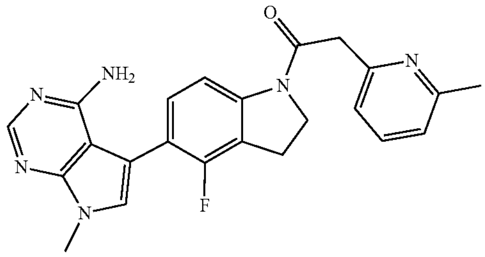

GSK2656157

TABLE 4

KINOMEscan ® in vitro competition binding assay for select kinases for Examples 1, 9 and GSK2656157 where "Inhibition" refers to greater than 50% inhibition and "No Inhibition" refers to less than 50% inhibition.

| Kinase | Example 9 | Example 1 | GSK2656157 * |
|---|---|---|---|
| AURKB | Inhibition | No Inhibition | Inhibition |
| AXL | No inhibition | No Inhibition | Inhibition |
| BLK | Inhibition | No Inhibition | Inhibition |
| CAMK4 | Inhibition | No Inhibition | No inhibition |
| CDK11 | Inhibition | No Inhibition | Inhibition |
| CDK8 | Inhibition | No Inhibition | Inhibition |
| CSF1R | Inhibition | No Inhibition | Inhibition |
| EIF2AK1 | Inhibition | No Inhibition | Inhibition |
| EPHB6 | Inhibition | No Inhibition | Inhibition |
| FLT3 | Inhibition | No Inhibition | No Inhibition |
| HIPK4 | Inhibition | No Inhibition | No Inhibition |
| LOK | Inhibition | No Inhibition | Inhibition |
| MAP3K15 | Inhibition | No Inhibition | No Inhibition |
| MAP3K2 | Inhibition | No Inhibition | Inhibition |
| MAP3K3 | Inhibition | No Inhibition | No Inhibition |
| MEK5 | Inhibition | No Inhibition | Inhibition |
| MKNK2 | Inhibition | No Inhibition | No Inhibition |
| NEK1 | Inhibition | No Inhibition | No Inhibition |
| NEK5 | Inhibition | No Inhibition | No Inhibition |
| PIK3C2B | Inhibition | No Inhibition | No Inhibition |
| RIOK2 | Inhibition | No Inhibition | Inhibition |
| RIPK1 | No Inhibition | No Inhibition | Inhibition |
| RIPK2 | Inhibition | No Inhibition | No Inhibition |
| RIPK5 | Inhibition | No Inhibition | No Inhibition |
| TESK1 | Inhibition | No Inhibition | No Inhibition |
| TIE2 | Inhibition | No Inhibition | No Inhibition |
| TRKA | Inhibition | No Inhibition | Inhibition |
| TRKB | Inhibition | No Inhibition | No Inhibition |
| TRKC | Inhibition | No Inhibition | Inhibition |
| VRK2 | Inhibition | No Inhibition | Inhibition |
| YANK1 | Inhibition | No Inhibition | No Inhibition |

TABLE 4-continued

| KINOMEscan ® in vitro competition binding assay for select kinases for Examples 1, 9 and GSK2656157 where "Inhibition" refers to greater than 50% inhibition and "No Inhibition" refers to less than 50% inhibition. | | | |
|---|---|---|---|
| Kinase | Example 9 | Example 1 | GSK2656157 * |
| YANK2 | Inhibition | No Inhibition | No Inhibition |
| YSK4 | Inhibition | No Inhibition | Inhibition |

* ACS Med Chem Lett. Aug. 12, 2013; 4(10): 964-8.

REFERENCES

Adrian L. Smith et al., Discovery of 1H-Pyrazol-3 (2H)-ones as Potent and Selective Inhibitors of Protein Kinase R-like Endoplasmic Reticulum Kinase (PERK), *J. Med. Chem.*, 2015, 58 (3), pp 1426-1441

Ron, D.; Walter, P. Signal integration in the endoplasmic reticulum unfolded protein response *Nat. Rev. Mol. Cell Biol.* 2007, 8, 519-529

Shore, G. C.; Papa, F. R.; Oakes, S. A. Signaling cell death from the endoplasmic reticulum stress response *Curr. Opin. Cell Biol.* 2011, 23, 143-149

Carrara, M.; Prischi, F.; Ali, M. M. U. UPR signal activation by luminal sensor domains *Int. J. Mol. Sci.* 2013, 14, 6454-6466

Ma, Y.; Hendershot, L. M. The role of the unfolded protein response in tumor development: friend or foe? *Nat. Rev. Cancer* 2004, 4, 966-977

Walter, P.; Ron, D. The unfolded protein response: from stress pathway to homeostatic regulation *Science* 2011, 334, 1081-1086

Vandewynckel, Y. P.; Laukens, D.; Geerts, A.; Bogaerts, E.; Paridaens, A.; Verhelst, X.; Jans sens, S.; Heindryckx, F.; van Vlierberghe, H. The paradox of the unfolded protein response in cancer *Anticancer Res.* 2013, 33, 4683-4694

Gao, Y.; Sartori, D. J.; Li, C.; Yu, Q.-C.; Kushner, J. A.; Simon, M. C.; Diehl, J. A. PERK is required in the adult pancreas and is essential for maintenance of glucose homeostasis *Mol. Cell. Biol.* 2012, 32, 5129-5139

Bi, M.; Naczki, C.; Koritzinsky, M.; Fels, D.; Blais, J.; Hu, N.; Harding, H.; Novoa, I.; Varia, M.; Raleigh, J.; Scheuner, D.; Kaufman, R. J.; Bell, J.; Ron, D.; Wouters, B. G.; Koumenis, C. ER stress-regulated translation increases tolerance to extreme hypoxia and promotes tumor growth *EMBO J.* 2005, 24, 3470-3481

Kim, I.; Xu, W.; Reed, J. C. Cell death and endoplasmic reticulum stress: disease relevance and therapeutic opportunities *Nat. Rev. Drug Discovery* 2008, 7, 1013-1030

Fels, D. R.; Koumenis, C. The PERK/eIF2α/ATF4 module of the UPR in hypoxia resistance and tumor growth *Cancer Biol. Ther.* 2006, 5, 723-728

Jeffrey M. Axten, Stuart P. Romeril, Arthur Shu, Jeffrey Ralph, Jesns R. Medina, Yanhong Feng, William Hoi Hong Li, Seth W. Grant, Dirk A. Heerding, Elisabeth Minthorn, Thomas Mencken, Nathan Gaul, Aaron Goetz, Thomas Stanley, Annie M. Hassell, Robert T. Gampe, Charity Atkins, and Rakesh Kumar. Discovery of GSK2656157: An Optimized PERK Inhibitor Selected for Preclinical Development. *ACS Medicinal Chemistry Letters* 2013 4 (10), 964-968.

Diego Rojas-Rivera1,2, Tinneke Delvaeye1,2,3, Ria Roelandt1,2, Wim Nerinckx4,5, Koen Augustyns6, Peter Vandenabeele1,2 and Mathieu J M Bertrand. When PERK inhibitors turn out to be new potent RIPK1 inhibitors: critical issues on the specificity and use of GSK2606414 and GSK2656157. Cell Death and Differentiation (2017) 24, 1100-1110.

WO2018/194885

U.S. Publication No. 2017/0165259

U.S. Pat. No. 8,598,156

What is claimed is:

1. A compound of the formula (Ia):

(Ia)

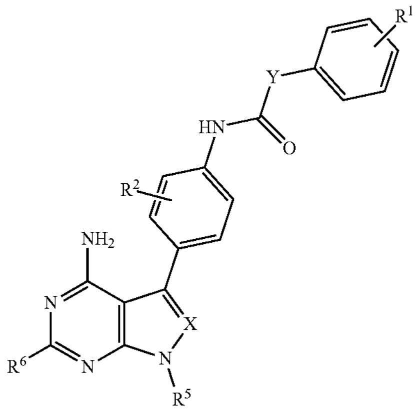

wherein:

Y is $CR^{3a}R^{3b}$;

$R^{3a}$ is H or alkyl;

$R^{3b}$ is $OR^{3c}$ or $NR_{3d}R^{3e}$;

Each $R^1$ is independently H, deuterium, halo, alkyl, cycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^1$ substituents;

Each $R^2$ is independently H, deuterium, halo, alkyl, $C_{0-6}$alkylcycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^2$ substituents;

$R^{3c}$, $R^{3d}$ and $R^{3e}$ are each independently H or alkyl, optionally substituted by one or more independent G3 substituents;

X is $CR^7$ or N;

$R^5$ is H, alkyl, cycloalkyl, or heterocycloalkyl, optionally substituted by one or more independent $G^4$ substituents;

$R^6$ is alkyl, $CD_3$, or $CF_3$;

$R^7$ is H, CN, or alkyl, optionally substituted by one or more independent deuterium or halo;

$G^1$, $G^2$, $G^3$, and $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, $C(O)R^8$, $C(O)OR^8$, $C(O)NR^8R^9$, $OC(O)R^8$, $OC(O)OR^8$, $OC(O)NR^8R^9$, $N(R^{10})C(O)R^8$, $N(R^{10})C(O)OR^8$, $N(R^{10})C(O)NR^8R^9$, $S(O)_nR^8$, $S(O)_nOR^8$, $S(O)_nNR^8R^9$, $N(R^{10})$ $S(O)R^8$, $N(R^{10})S(O)_nOR^8$, or $N(R^{10})$ $S(O)_nNR^8R^9$, optionally substituted by one or more independent H, deuterium, halo, OH, CN, or $NO_2$;

$R^8$, $R^9$, or and $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;

n is 0, 1, or 2;

or a pharmaceutically acceptable salt thereof.

2. The compound of claim 1 of the formula (Ib):

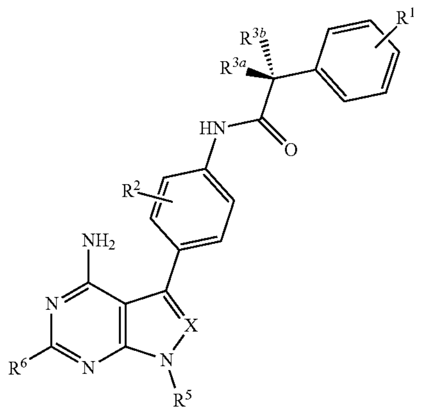

(Ib)

wherein:

X is CH or N;

Each $R^1$ is independently H, deuterium, halo, alkyl, cycloalkyl, $C_{0-6}$alkyl-O-C1-12alkyl, $C_{0-6}$alkyl-OH, or $C_{0-6}$alkyl-O-C3-12cycloalkyl, optionally substituted by one or more independent $G^1$ substituents;

Each $R^2$ is independently H, deuterium, halo, alkyl, cycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^2$ substituents;

$R^{3a}$ is H or alkyl;

$R^{3b}$ is $OR^{3c}$ or $NR^{3d}R^{3e}$;

$R^{3c}$, $R^{3d}$ and $R^{3e}$ are each independently H or alkyl, optionally substituted by one or more independent $G^3$ substituents;

$R^5$ is H, alkyl, cycloalkyl, or heterocycloalkyl, optionally substituted by one or more independent $G^4$ substituents;

$R^6$ is alkyl, $CD_3$, or $CF_3$;

$G^1$, $G^2$, $G^3$, and $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, C(O)$R^8$, C(O)$OR^8$, C(O)$NR^8R^9$, OC(O)$R^8$, OC(O)$OR^8$, OC(O)$NR^8R^9$, $N(R^{10})C(O)R^8$, $N(R^{10})C(O)OR^8$, $N(R^{10})C(O)NR^8R^9$, $S(O)_nR8$, $S(O)_nOR^8$, $S(O)_nNR^8R^9$, $N(R^{10})$ $S(O)R^8$, $N(R^{10})S(O)_nOR^8$, or $N(R^{10})S(O)_nNR^8R^9$, optionally substituted by one or more independent H, deuterium, halo, OH, CN, or $NO_2$;

$R^8$, $R^9$, and $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;

n is 0, 1, or 2;

or a pharmaceutically acceptable salt thereof.

3. The compound of claim 1 of the formula (Ic):

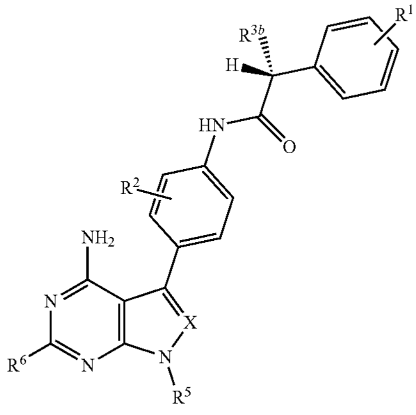

(Ic)

wherein:

X is CH or N;

Each $R^1$ is independently H, deuterium, halo, alkyl, $C_{0-6}$alkyl-OH, or $C_{0-6}$alkyl-O—$C_{1-12}$alkyl, optionally substituted by one or more independent $G^1$ substituents;

Each $R^2$ is independently H, deuterium, halo, alkyl, $C_{0-6}$alkyl-OH, or $C_{0-6}$alkyl-O—$C_{1-12}$alkyl, optionally substituted by one or more independent $G^2$ substituents;

$R^{3b}$ is $OR^{3c}$;

$R^{3c}$ is H or alkyl, optionally substituted by one or more independent $G^3$ substituents;

$R^5$ is H, alkyl, cycloalkyl, or heterocycloalkyl, optionally substituted by one or more independent $G^4$ substituents;

$R^6$ is alkyl, $CD_3$, or $CF_3$;

$G^1$, $G^2$, $G^3$, and $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, C(O)$R^8$, C(O)$OR^8$, C(O)$NR^8R^9$, OC(O)$R^8$, OC(O)$OR^8$, OC(O)$NR^8R^9$, $N(R^{10})$ C(O)$R^8$, $N(R^{10})$ C(O)$OR^8$, $N(R^{10})$ C(O)$NR^8R^9$, $S(O)_nR^8$, $S(O)_nOR^8$, $S(O)_nNR^8R^9$, $N(R^{10})S(O)_nR^8$, $N(R^{10})S(O)_nOR^8$, or $N(R^{10})S(O)_nNR^8R^9$, optionally substituted by one or more independent H, deuterium, halo, OH, CN, or $NO_2$;

$R^8$, $R^9$, and $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;

n is 0, 1, or 2;

or a pharmaceutically acceptable salt thereof.

4. The compound of claim 1 of the formula (Id):

(Id)

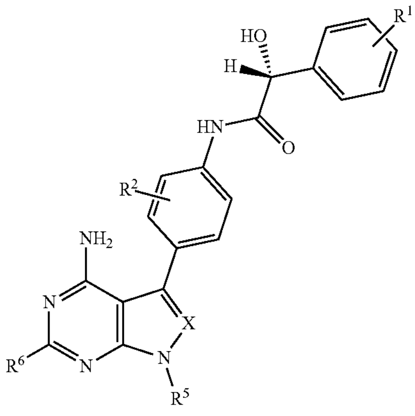

wherein:
X is CH or N;
Each $R^1$ is independently H, deuterium, halo, alkyl, $C_{0-6}$alkyl-OH, or $C_{0-6}$alkyl-O—$C_{1-12}$alkyl, optionally substituted by one or more independent H, deuterium, or halo;
Each $R^2$ is independently H, deuterium, halo, alkyl, $C_{0-6}$alkyl-OH, or $C_{0-6}$alkyl-O—$C_{1-12}$alkyl, optionally substituted by one or more independent H, deuterium or halo;
$R^5$ is H, alkyl, cycloalkyl, or heterocycloalkyl, optionally substituted by one or more independent H, deuterium, $C_{1-6}$alkyl, halo, OH, or CN;
Rois alkyl, $CD_3$, or $CF_3$;
or a pharmaceutically acceptable salt thereof.

5. The compound of claim 1 of the formula (Ie):

(Ie)

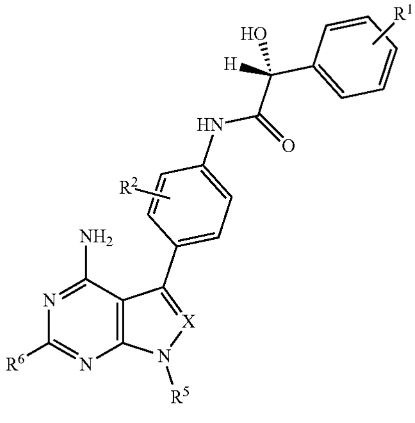

wherein:
X is CH or N;
Each $R^1$ is independently H, deuterium, halo, alkyl, $C_{0-6}$alkyl-OH, or $C_{0-6}$alkyl-O—$C_{1-12}$alkyl, optionally substituted by one or more independent H, deuterium, or halo;
Each $R^2$ is independently H, deuterium, halo, alkyl, $C_{0-6}$alkyl-OH, or $C_{0-6}$alkyl-O—$C_{1-12}$alkyl, optionally substituted by one or more independent H, deuterium or halo;
substituted by one or more independent H, deuterium, halo, OH, or CN;
or a pharmaceutically acceptable salt thereof.

6. The compound of claim 1, wherein X is CH.

7. The compound of claim 1, wherein $R^1$ is H, methyl, ethyl, isopropyl, methoxy, ethoxy, propoxy, isopropoxy, deuterium, $CF_3$, $OCF_3$, fluoro, or chloro.

8. The compound of claim 1, wherein $R^2$ is H, methyl, ethyl, propyl, isopropyl, methoxy, ethoxy, propoxy, isopropoxy, fluoro, chloro, $CF_3$ or $OCF_3$.

9. The compound of claim 1, wherein $R^5$ is H, $CH_3$, or $CD_3$.

10. The compound of claim 1, wherein $R^6$ is H, methyl, ethyl, isopropyl, $CD_3$, or $CF_3$.

11. The compound of claim 1, wherein $G^1$, $G^2$, $G^3$, and $G^4$ are each independently H, deuterium, halo, CN, $NO_2$, $C_{1-6}$alkyl, $C_{3-8}$cycloalkyl, $C_{3-8}$heterocycloalkyl, $OR^8$, $NR^8R^9$, $C(O)R^8$, $C(O)OR^8$, $C(O)NR^8R^9$, $OC(O)R^8$, $OC(O)OR^8$, $OC(O)NR^8R^9$, $N(R^{10})C(O)R^8$, $N(R^{10})C(O)OR^8$, $N(R^{10})C(O)NR^8R^9$, $S(O)_nR^8$, $S(O)_nOR^8$, $S(O)_nNR^8R^9$, $N(R^{10})S(O)_nR^8$, $N(R^{10})S(O)_nOR^8$, or $N(R^{10})S(O)_nNR^8R^9$, optionally substituted by one or more independent H, deuterium, halo, OH, CN, or $NO_2$.

12. The compound of claim 1, wherein $G^1$, $G^2$, $G^3$, and $G^4$ are each independently H, deuterium, halo, CN, $NO_2$, $C_{1-3}$alkyl, $C_{3-6}$cycloalkyl, $C_{3-6}$heterocycloalkyl, $OR^8$, $NR^8R^9$, $C(O)R^8$, $C(O)OR^8$, $C(O)NR^8R^9$, $OC(O)R^8$, $OC(O)OR^8$, $OC(O)NR^8R^9$, $N(R^{10})$ $C(O)R^8$, $N(R^{10})$ $C(O)OR^8$, $N(R^{10})$ $C(O)NR^8R^9$, $S(O)_nR^8$, $S(O)_nOR^8$, $S(O)_nNR^8R^9$, $N(R^{10})S(O)_nR^8$, $N(R^{10})S(O)_nOR^8$, or $N(R^{10})S(O)_nNR^8R^9$, optionally substituted by one or more independent H, deuterium, halo, OH, CN, or $NO_2$.

13. The compound of claim 1, wherein $R^1$ is chloro, fluoro, ethyl, isopropyl, methyl, methoxy, or $CF_3$.

14. The compound of claim 1, wherein $R^2$ is chloro, fluoro, ethyl, methyl, methoxy, $CF_3$, or —O—$CF_3$.

15. The compound of claim 1, wherein $R^5$ is methyl.

16. The compound of claim 1, wherein $R^6$ is H, ethyl, methyl, isopropyl or $CF_3$.

17. A pharmaceutical composition comprising the compound or the pharmaceutically acceptable salt thereof according to claim 1 with one or more pharmaceutically acceptable carriers, diluents, or excipients.

18. The compound according to claim 1 which is

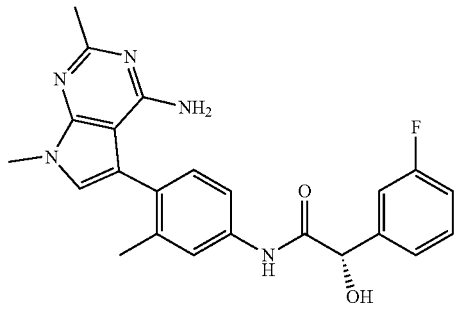 [SMILES: Cc1nc(N)c2c(-c3ccc(NC(=O)[C@@H](O)c4cccc(F)c4)cc3C)cn(C)c2n1]

or a pharmaceutically acceptable salt thereof.

19. A pharmaceutical composition, comprising the compound or the pharmaceutically acceptable salt thereof according to claim 18 with one or more pharmaceutically acceptable carriers, diluents, or excipients.

20. A compound selected from the group consisting of:
N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;

(R)—N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;

(S)—N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;

N-(4-(4-amino-2,7-dimethyl-7H-pyrrolo[2,3-d]pyrimidin-5-yl)-3-methylphenyl)-2-(3-fluorophenyl)-2-hydroxyacetamide;

(R)—N-(4-(4-amino-2,7-dimethyl-7H-pyrrolo[2,3-d]pyrimidin-5-yl)-3-methylphenyl)-2-(3-fluorophenyl)-2-hydroxyacetamide;

(S)—N-(4-(4-amino-2,7-dimethyl-7H-pyrrolo[2,3-d]pyrimidin-5-yl)-3-methylphenyl)-2-(3-fluorophenyl)-2-hydroxyacetamide;

N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;

(R)—N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;

(S)—N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;

N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;

(R)—N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;

(S)—N-(4-(4-amino-2,7-dimethyl-7H-pyrrolo[2,3-d]pyrimidin-5-yl)-2-fluoro-3-methylphenyl)-2-(3-fluorophenyl)-2-hydroxyacetamide;

N-(4-(4-amino-2,7-dimethyl-7H-pyrrolo[2,3-d]pyrimidin-5-yl)-3-(trifluoromethyl)phenyl)-2-(3-fluorophenyl)-2-hydroxyacetamide;

(R)—N-(4-(4-amino-2,7-dimethyl-7H-pyrrolo[2,3-d]pyrimidin-5-yl)-3-(trifluoromethyl)phenyl)-2-(3-fluorophenyl)-2-hydroxyacetamide;

(S)—N-(4-(4-amino-2,7-dimethyl-7H-pyrrolo[2,3-d]pyrimidin-5-yl)-3-(trifluoromethyl)phenyl)-2-(3-fluorophenyl)-2-hydroxyacetamide;

N-(4-(4-amino-2,7-dimethyl-7H-pyrrolo[2,3-d]pyrimidin-5-yl)-3-(trifluoromethoxy)phenyl)-2-(3-fluorophenyl)-2-hydroxyacetamide;

(R)—N-(4-(4-amino-2,7-dimethyl-7H-pyrrolo[2,3-d]pyrimidin-5-yl)-3-(trifluoromethoxy)phenyl)-2-(3-fluorophenyl)-2-hydroxyacetamide;

(S)—N-(4-(4-amino-2,7-dimethyl-7H-pyrrolo[2,3-d]pyrimidin-5-yl)-3-(trifluoromethoxy)phenyl)-2-(3-fluorophenyl)-2-hydroxyacetamide;

N-(4-(4-amino-2,7-dimethyl-7H-pyrrolo[2,3-d]pyrimidin-5-yl) phenyl)-2-(3-fluorophenyl)-2-hydroxyacetamide;

(R)—N-(4-(4-amino-2,7-dimethyl-7H-pyrrolo[2,3-d]pyrimidin-5-yl) phenyl)-2-(3-fluorophenyl)-2-hydroxyacetamide;

(S)—N-(4-(4-amino-2,7-dimethyl-7H-pyrrolo[2,3-d]pyrimidin-5-yl) phenyl)-2-(3-fluorophenyl)-2-hydroxyacetamide;

N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;

(R)—N-(4-(4-amino-2-isopropyl-7-methyl-7H-pyrrolo[2,3-d]pyrimidin-5-yl)-3-methylphenyl)-2-(3-fluorophenyl)-2-hydroxyacetamide; and (S)—N-(4-(4-amino-2-isopropyl-7-methyl-7H-pyrrolo[2,3-d]pyrimidin-5-yl)-3-methylphenyl)-2-(3-fluorophenyl)-2-hydroxyacetamide;

or a pharmaceutically acceptable salt thereof.

* * * * *